(12) United States Patent
Kliger et al.

(10) Patent No.: US 8,512,708 B2
(45) Date of Patent: Aug. 20, 2013

(54) GP96 DERIVED PEPTIDES

(75) Inventors: Yossef Kliger, Rishon Le Zion (IL); Ofer Levy, D.N Shimshon Moshav Mesilat Zion (IL); Itamar Borukhov, Ramat Hasharon (IL); Anat Amir, D.N. Negev (IL); Anat Oren, Tel Aviv (IL)

(73) Assignee: Compugen Ltd., Tel Aviv (IL)

( * ) Notice: Subject to any disclaimer, the term of this patent is extended or adjusted under 35 U.S.C. 154(b) by 7 days.

(21) Appl. No.: 12/921,920

(22) PCT Filed: Mar. 12, 2009

(86) PCT No.: PCT/IL2009/000286
§ 371 (c)(1),
(2), (4) Date: Oct. 22, 2010

(87) PCT Pub. No.: WO2009/113074
PCT Pub. Date: Sep. 17, 2009

(65) Prior Publication Data
US 2011/0189188 A1 Aug. 4, 2011

Related U.S. Application Data

(60) Provisional application No. 61/064,585, filed on Mar. 13, 2008, provisional application No. 61/136,288, filed on Aug. 25, 2008.

(51) Int. Cl.
*A61K 39/00* (2006.01)

(52) U.S. Cl.
USPC .................. 424/185.1; 424/192.1; 424/193.1; 424/278.1; 530/324

(58) Field of Classification Search
None
See application file for complete search history.

(56) References Cited

U.S. PATENT DOCUMENTS

| | | | |
|---|---|---|---|
| 2007/0003519 A1* | 1/2007 | Lu et al. | 424/93.2 |
| 2007/0154478 A1* | 7/2007 | Burnie et al. | 424/145.1 |

FOREIGN PATENT DOCUMENTS

| | | |
|---|---|---|
| WO | WO 9526365 A1 * | 10/1995 |
| WO | 03/029419 A2 | 4/2003 |
| WO | 2004/101766 A2 | 11/2004 |
| WO | 2005/012482 A2 | 2/2005 |
| WO | WO 2008133359 A1 * | 11/2008 |

OTHER PUBLICATIONS

Khachigian et al., J Immunol Methods. Jul. 5, 1991;140(2):249-58.*
PCT/IB/373 International Preliminary Report on Patentability of International Application No. PCT/IL2009/000286, issued Sep. 14, 2010, 7 pages.
The International Search Report of International Application No. PCT/IL2009/000286, mailed Aug. 28, 2009, 2 pages.
Abdollahi-Roodsaz, et al., "Inhibition of Toll-like Receptor 4 Breaks the Inflammatory Loop in Autoimmune Destructive Arthritis", Arthritis & Rheumatism, vol. 56, No. 9, pp. 2957-2967, (2007).
Bauer, et al., "Immunobiology of toll-like receptors in allergic disease", Immunobiology, vol. 212, pp. 521-533, (2007).
Binder, et al., "CD91: a receptor for heat shock protein gp96", Nature Immunology, vol. 1, No. 2, pp. 151-155, (2000).
Deng, et al., "The Role of Toll-Like Receptors 2 and 4 in Acute Allograft Rejection After Liver Transplantation", Transplantation Proceedings, vol. 39, pp. 3222-3224, (2007).
Fort, et al., "A Synthetic TLR4 Antagonist Has Anti-Inflammatory Effects in Two Murine Models of Inflammatory Bowel Disease", The Journal of Immunology, vol. 174, pp. 6416-6423, (2005).
Frantz, et al., "Mechanisms of Disease: Toll-like receptors in cardiovascular disease", Nature Clinical Practice Cardiovascular Medicine, vol. 4, No. 8, pp. 444-454, (2007).
Gearing, "Targeting toll-like receptors for drug development: a summary of commercial approaches", Immunology and Cell Biology, vol. 85, pp. 490-494, (2007).
Han, et al., "Aminoacyl-tRNA Synthetase-Interacting Multifunctional Protein 1/p43 Controls Endoplasmic Reticulum Retention of Heat Shock Protein gp96: Its Pathological Implications in Lupus-Like Autoimmune Diseases", Am J Pathol, vol. 170, pp. 2042-2054, (2007).
Hilf, et al., "The heat shock protein Gp96 links innate and specific immunity", Int. J. Hyperthermia, vol. 18, No. 6, pp. 521-533, (2002).
Huang, et al., "TLR signaling by tumor and immune cells: a double-edged sword", Oncogene, vol. 27, pp. 218-224, (2008).
Iwasaki, et al., "Toll-like receptor control of the adaptive immune responses", Nature Immunology, vol. 5, No. 10, pp. 987-995, (2004).
Janetzki, et al., "Generation of Tumor-Specific Cytotoxic T Lymphocytes and Memory T Cells by Immunization with Tumor-Derived Heat Shock Protein gp96", Journal of Immunology, vol. 21, No. 4, pp. 269-276, (1998).
Kliger, et al., "Conformational change blockers", FEBS Journal, vol. 275, Suppl. 1, p. 170, Abstract pp. 3A-54, (2008).
Li, et al. "Roles of heat-shock proteins in antigen presentation and cross-presentation", Current Opinion in Immunology, vol. 14, pp. 45-51, (2002).
Li, et al., "An Integrated View of the Roles and Mechanisms of Heat Shock Protein GP96-Peptide Complex in Eliciting Immune Response", Frontiers in Bioscience, vol. 7, pp. 731-751, (2002).
Liu, et al., "Cell surface expression of an endoplasmic reticulum resident heat shock protein gp96 triggers MyD88—dependent systemic autoimmune diseases", PNAS, vol. 100, No. 26, pp. 15824-15829, (2003).
Liu, et al., "TLR4 Up-Regulation at Protein or Gene Level Is Pathogenic for Lupus-Like Autoimmune Disease", The Journal of Immunology, vol. 177, pp. 6880-6888, (2006).
Morimoto, "Regulation of the heat shock transcriptional response: cross talk between a family of heat shock factors, molecular chaperones, and negative regulators", Genes & Development, vol. 12, pp. 3788-3796, (1998).
Papadimitraki, et al., "Toll like receptors and autoimmunity: A critical appraisal", Journal of Autoimmunity, vol. 29, pp. 310-318, (2007).
Quintana, et al., "Heat Shock Proteins as Endogenous Adjuvants in Sterile and Septic Inflammation", The Journal of Immunology, vol. 175, pp. 2777-2782, (2005).
Reed, et al., "GRP94/gp96 Elicits ERK Activation in Murine Macrophages", The Journal of Biological Chemistry, vol. 278, No. 34, pp. 31853-31860, (2003).

(Continued)

*Primary Examiner* — Michael Szperka
(74) *Attorney, Agent, or Firm* — Vorys, Sater, Seymour and Pease LLP; Susanne M. Hopkins

(57) ABSTRACT

Provided is a gp96-derived peptides or homologs or derivatives thereof, pharmaceutical composition including them, a use thereof for therapy and for the manufacture of a medicament, a method of treating a wide range of conditions, disorders and diseases therewith, nucleotide sequences encoding them, antibodies directed to epitopes thereof and fusion proteins including them.

4 Claims, 21 Drawing Sheets

(56) References Cited

OTHER PUBLICATIONS

Srivastava, "Roles of Heat-Shock Proteins in Innate and Adaptive Immunity", Nature Reviews Immunology, vol. 2, pp. 185-194, (2002).

Suto, et al., "A Mechanism for the Specific Immunogenicity of Heat Shock Protein-Chaperoned Peptides", Science, vol. 269, pp. 1585-1588, (1995).

Triantafilou, et al., "Heat-shock protein 70 and heat-shock protein 90 associate with Toll-like receptor 4 in response to bacterial lipopolysaccharide", Biochemical Society Transactions, vol. 32, Part 4, pp. 636-639, (2004).

Tse, et al., "Update on toll-like receptor-directed therapies for human disease", Ann Rheum Dis, vol. 66, Suppl. III, pp. iii77-iii80, (2007).

Tsujimoto, et al., "Role of Toll-Like Receptors in the Development of Sepsis", Shock, vol. 29, No. 3, pp. 315-321, (2008).

Waldorf, et al., "Pretreatment with Toll-like Receptor 4 Antagonist Inhibits Lipopolysaccharide-Induced Preterm Uterine Contractility, Cytokines, and Prostaglandins in Rhesus Monkeys", Reproductive Sciences, vol. 15, No. 2, pp. 121-127, (2008).

Warger, et al., "Interaction of TLR2 and TLR4 Ligands with the N-terminal Domain of Gp96 Amplifies Innate and Adaptive Immune Responses", The Journal of Biological Chemistry, vol. 281, No. 32, pp. 22545-22553, (2006).

Yang, et al., "Heat Shock Protein gp96 Is a Master Chaperone for Toll-like Receptors and Is Important in the Innate Function of Macrophages", Immunity, vol. 26, pp. 215-226, (2007).

Yin, et al., "Computational Design of Peptides That Target Transmembrane Helices", Science, vol. 315, pp. 1817-1822, (2007).

Schild, et al., "gp96—The immune system's Swiss army knife", Nature Immunology, vol. 1, pp. 100-101, (2000).

\* cited by examiner

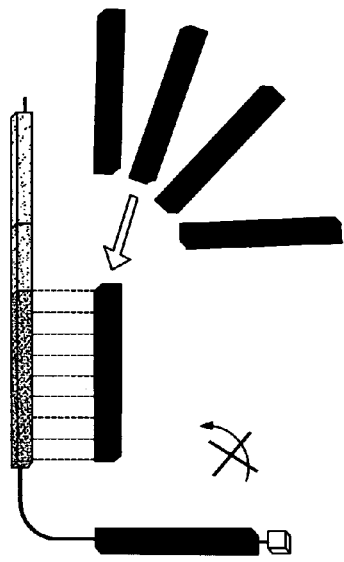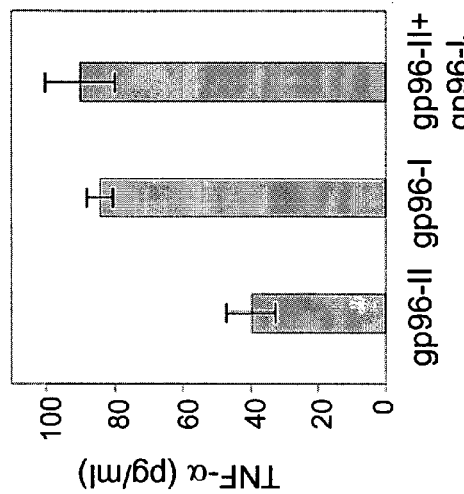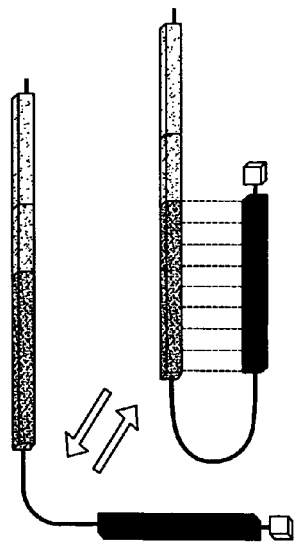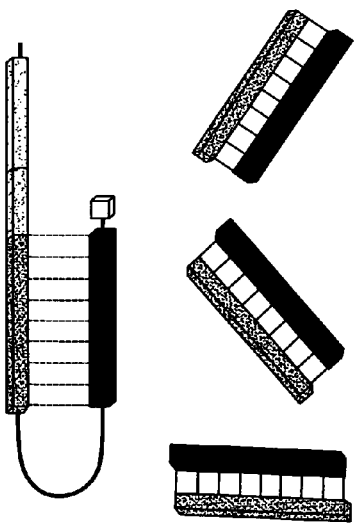
Figure 20A
Figure 20B
Figure 20C
Figure 20D

| | |
|---|---|
| gi\|4507677_0\|[Homo Sapience] | LNVSRETLQQHKLLKVIRKKLVRKTLDMIKKIADDKY |
| gi\|27807263_0\|[Bos taurus] | LNVSRETLQQHKLLKVIRKKLVRKTLDMIKKIADEKY |
| gi\|50979166_0\|[Canis familiaris] | LNVSRETLQQHKLLKVIRKKLVRKTLDMIKKIADEKY |
| gi\|109098491_0\|[Macaca fascicularis] | LNVSRETLQQHKLLKVIRKKLVRKTLDMIKKIADDKY |
| gi\|75070529_0\|[Pongo pygmaeus] | LNVSRETLQQHKLLKVIRKKLVRKTLDMIKKIADDKY |
| gi\|6755863_0\|[Mus musculus] | LNVSRETLQQHKLLKVIRKKLVRKTLDMIKKIADEKY |
| gi\|17865698_0\|[Sus scrofa] | LNVSRETLQQHKLLKVIRKKLVRKTLDMIKKIADEKY |
| gi\|45383562_0\|[Gallus gallus] | LNVSRETLQQHKLLKVIRKKLVRKTLDMIKKIAEEKY |
| gi\|6015101_0\|[Oryctolagus cuniculus] | LNVSRETLQQHKLLKVIRKKLVRKTLDMIKKIADEKY |
| gi\|544242_0\|[Hordeum vulgare] | LNVSREMLQQHSSLKTIKKKLIRKALDMIRKLAEEDP |
| gi\|15233740_0\|[Arabidopsis thaliana] | LNVSREMLQQHSSLKTIKKKLIRKALDMIRKLAEEDP |
| gi\|462013_0\|[Catharanthus roseus] | LNVSREMLQQHSSLKTIKKKLIRKALDMIRKIADEDP |

Figure 22

| | |
|---|---|
| gi_62088647_Homo sapiens | TLQQHKLLKVIRKKLVRKTLDMIKKIADDKY |
| gi_90076963_Macaca fascicularis | TLQQHKLLKVIRKKLVRKTLDMIKKIADDKY |
| gi_37805386_Xenopus laevis | TLQQHKLLKVIRKKLVRKTLDMIKKIAEDKY |
| gi_210032364_Rattus norvegicus | TLQQHKLLKVIRKKLVRKTLDMIKKIADEKY |
| gi_75775555_Bos Taurus | TLQQHKLLKVIRKKLVRKTLDMIKKIADEKY |
| gi_74190331_Mus musculus | TLQQHKLLKVIRKKLVRKTLDMIKKIADEKY |
| gi_403496_Canis familiaris | TLQQHKLLKVIRKKLVRKTLDMIKKIADEKY |
| gi_39645914_Danio rerio | TLQQHKLLKVIRKKLVRKTLDMIKKIAEEQY |

Figure 23

| | |
|---|---|
| gi_403496_Canis familiaris | HKLLKVIRKKLVRKTLDMIKKIADEKYNDTFWKEF |
| gi_194220333_Gallus gallus | HKLLKVIRKKLVRKTLDMIKKIAEEKYNDTFWKEF |
| gi_44890630_Homo sapiens | HKLLKVIRKKLVRKTLDMIKKIADDKYNDTFWKEF |
| gi_114646591_Pan troglodytes | HKLLKVIRKKLVRKTLDMIKKIADDKYNDTFWKEF |
| gi_109098490_Macaca mulatta | HKLLKVIRKKLVRKTLDMIKKIADDKYNDTFWKEF |
| gi_679970925_Macaca fascicularis | HKLLKVIRKKLVRKTLDMIKKIADDKYNDTFWKEF |
| gi_557731899_Pongo abelii | HKLLKVIRKKLVRKTLDMIKKIADDKYNDTFWKEF |
| gi_74190331_Mus musculus | HKLLKVIRKKLVRKTLDMIKKIADEKYNDTFWKEF |
| gi_210032364_Rattus norvegicus | HKLLKVIRKKLVRKTLDMIKKIADEKYNDTFWKEF |
| gi_75775555_Bos Taurus | HKLLKVIRKKLVRKTLDMIKKIADEKYNDTFWKEF |
| gi_2239252_Sus scrofa | HKLLKVIRKKLVRKTLDMIKKIADEKYNDTFWKEF |
| gi_149742973_Equus caballus | HKLLKVIRKKLVRKTLDMIKKIADEKYNDTFWKEF |

Figure 24

GP96 DERIVED PEPTIDES

This is a National Phase Application filed under 35 U.S.C. 371 as a national stage of PCT/IL2009/000286, filed on Mar. 12, 2009, an application claiming the benefit under 35 USC 119(e) U.S. Provisional Application No. 61/064,585, filed on Mar. 13, 2008, and an application claiming the benefit under 35 USC 119(e) U.S. Provisional Application No. 61/136,288, filed on Aug. 25, 2008,the content of each of which is hereby incorporated by reference in its entirety.

FIELD OF THE INVENTION

This invention relates to the field of gp96 derived peptides.

The Sequence Listing submitted in text format (.txt) on Apr. 7, 2011, named "sequencelisting2.txt, (created on Thur., Apr. 7, 2011, 27.1 KB), is incorporated herein by reference.

BACKGROUND OF THE INVENTION

Heat shock proteins (HSPs) are known conventionally as stress proteins or protein chaperones which play fundamental housekeeping roles in all cellular events involving protein folding and unfolding (Morimoto R. I., 1998 *Genes Dev* 12:3788-3796). HSPs are multifunctional proteins and facilitate various processes including vesicular transport, signaling, and so forth. The HSP gp96 (which stands for glycoprotein of 96 kDa) also known as grp94, endoplasmin or ERp99, belongs to the HSP90 family of heat shock proteins. It is constitutively expressed and normally resides in the lumen of the endoplasmic reticulum (ER), where its chaperone function is vital for the proper folding of many substrates. In humans, only one gene locus has been mapped on chromosome 12 and was named tra-1. It encodes a protein of 803 amino acids, which contains an ER-retention sequence, KDEL, at its C-terminus. Like other HSPs, gp96 is induced by the accumulation of misfolded proteins, it binds and hydrolyzes ATP and chaperones multiple protein substrates. The crucial role of gp96 as a housekeeping gene is emphasized by the fact that gp96-gene knockout mice are embryonic lethal (Li Z. et al., 2002 *Frontiers in Bioscience* 7:731-751).

Gp96 plays a critical role in presentation of exogenous antigens by MHC class I, by acting as a chaperone to such antigens, which then enter the cells through endocytosis. Subsequently, the antigenic peptide is transported into the endoplasmic reticulum where it is charged onto a cognate MHC class I molecule. That process, which is referred to as cross-presentation, leads to the presentation of MHC I-peptide complexes on the cell surface leading to stimulation of CD8+ T cells (Suto R. & P. K. Srivastava 1995 *Science* 269: 1585-1588). Thus, gp96 purified from cells chaperones antigenic peptides generated in that cell. Immunization with gp96-peptide complexes purified from tumors or pathogen-infected cells elicits specific immunity directed against the tumor or pathogen, respectively (Janetzki, S. et al., 1998 *J. Immunother.* 21:269-276).

Gp96 is the most intensely studied HSP from the immunological point of view, and has been shown to carry out many functions such as activating both innate and adaptive immunity, peptide antigen presentation, transfer of such peptides to MHC molecules, activation of antigen-presenting cells (APCs), and playing an important role in tumor immunity. gp96 also has several peptide-independent activities, including a critical role in the assembly of functional Toll-like receptors (TLRs), and acting as a danger signal by activating dendritic cells (DCs) to secrete proinflammatory cytokines and chemokines (Li Z. et al., 2002 *Curr Opin Immunol* 14:45-51; Srivastava, P. 2002 *Nat Rev Immunol* 2:185-194; Hilf N. et al 2002 *Int. J. Hyperthermia* 18:521-533). These combined features and multifunctional characteristics make gp96 a powerful weapon, and accordingly it has also been labeled "the Swiss Army Knife of the Immune System" (Schild and Rammensee 2000 *Nat. Immunol.* 1:100-101).

HSPs perform diverse functions in two alternative modes of inflammation: sterile inflammation, which results from endogenous stimuli and is necessary for body maintenance, and septic inflammation, which protects us from environmental pathogens. Endogenous HSPs, such as gp96, are key players in the modulation of these two modes of inflammation, and as such, they are potential targets for novel therapies for cancer, infections and autoimmunity (Quintana and Cohen, 2005 *J. Immunol.* 175: 2777-2782)

Recent studies provide new insights into the role of gp96 in the assembly of functional Toll-like receptors (TLRs). TLRs are an important family of receptors that contribute to innate immunity and regulate adaptive immunity. These pattern-recognition receptors are able to recognize unique structural entities such as bacterial lipoproteins (TLR2 in heterodimers with TLR1 or TLR6), double-stranded RNA (TLR3), lipopolysaccharide (LPS) (TLR4), bacterial flagellin (TLR5), certain pathogen-associated RNA sequences (TLR7), and pathogen-associated unmethylated CpG motifs in DNA (TLR9) (Iwasaki, A. & Medzhitov, R. 2004 *Nat Immunol.* 5:987-995). Defects in TLR expression or function can lead to increased susceptibility to infection with various pathogens. In contrast, excessive or inappropriate TLR signaling is associated with pathological processes, like LPS-induced endotoxin shock in sepsis, certain autoimmune and inflammatory conditions and cancer. Thus, mechanisms that regulate TLR expression and function may be critical for shaping both immunity to pathogens and pathologic immune reactions.

New evidence reveals that gp96 is the unique and obligatory master chaperone for TLRs. Intact gp96 is essential for signaling by TLR1, TLR2, TLR3, TLR4, TLR5, TLR7 and TLR9. In the absence of gp96, TLRs are not functional, are largely retained in the endoplasmic reticulum, and cannot mediate responses such as TLR4-induced endotoxin shock or induction of cytokines and host resistance by *Listeria monocytogenes* (Yang Y., et al. 2007 *Immunity* 26:215-226). In addition to its role as a chaperone for TLRs, gp96 has a role in the amplification of dendritic cell activation by bacterial products (Warger T. et al 2006 *J. Biol. Chem.* 281:22545-22553).

Enforcing cell surface expression of gp96 in a transgenic mouse model induced significant activation of dendritic cells and spontaneous lupus-like autoimmune disease. The development of such autoimmunity is dependent on MyD88, an important downstream adaptor protein for signaling by TLRs (Liu B. et al., 2003 *Proc Natl Acad Sci USA* 100:15824-15829). Similarly, disturbing ER retention of gp96 showed dendritic cell activation attributable to increased gp96 surface presentation and lupus-like autoimmune phenotypes (Han J. M. et al, 2007 *Am. J. Pathol.* 170:2042-2054). Hence, chronic activation of dendritic cells by gp96 may cause breakdown of peripheral tolerance, resulting in autoimmune disease. Indistinguishable results were obtained by over-expressing the tlr4 gene alone using gene amplification in transgenic mice. TLR4 increased expression, without any exogenous insult and induced a similar lupus-like autoimmune disease (Liu B., et al 2006 *J. of Immunol* 177:6880-6888). The dependence of TLRs' activity on gp96 function may explain these corresponding results which suggest that chronic stimulation by gp96 or by TLRs may contribute to the development of autoimmune disorders. Indeed, data originating predominantly from animal models of autoimmune disease and circumstantial data from human patients suggest that inappropriate activation of TLR pathways by endogenous or exogenous ligands may lead to the initiation and/or maintenance of autoimmune responses and tissue injury (Papadimitraki, E. V. et al. 2007 *J. of autoimmunity* 29:310-318). Furthermore, agents that are currently used to treat autoimmune diseases, such as chloroquine and hydroxychloroquine, were demonstrated to block TLR signaling, which may explain their efficacy.

The involvement of TLRs in the pathogenesis of autoimmune disorders prompted their development as promising targets for therapeutic agents. Specific TLR antagonists are in preclinical and clinical development as therapeutics for various inflammatory disorders and autoimmune diseases (Gearing A. J. H, 2007 *Immunology and Cell Biol.* 85:490-494; Tse K & Horner A. 2007 *Ann Rheum Dis.* 66(Suppl III):iii77-80). Inhibition of gp96 activity may also be used as a therapeutic target to lessen TLRs malfunctioning in various disease states. Specific examples of specific autoimmune diseases or animal models that have been targeted by inhibitors of TLRs as promising therapeutic agents include: Systemic Lupus Erythematosus (SLE)—a dual inhibitor of TLR7 and TLR9 prevented the progression of a lupus-like disease when injected to lupus prone mice. Inflammatory bowel diseases (IBD) and other chronic gastrointestinal inflammation conditions where TLR4 plays a role—an antagonist of TLR4 inhibited the development of moderate-to-severe disease in two mouse models of colonic inflammation (Fort et al, 2005 *J. Immunology* 174:6416-6423). TLR4 might also serve as a target in the treatment of rheumatoid arthritis as inhibition of TLR4 suppressed the severity of experimental arthritis (Abdollahi-Roodsaz et al, 2007 *Arthritis & Rheumatism* 56:2957-2967).

TLRs are present on a number of cell types believed to be involved in the development of allergic sensitization and the early asthmatic reaction. Indeed, experimental studies have largely demonstrated the implication of TLRs in both development and control of the allergic reaction. These results have demonstrated the clinical potential of pharmacologic interventions that target TLRs for the prevention and treatment of allergic diseases (Bauer S. et al. 2007 *Immunobiology* 212: 521-33).

TLRs activation also contributes to the development and progression of atherosclerosis, cardiac dysfunction in sepsis, congestive heart failure and ischemic injury. The involvement of TLRs in these conditions indicates that TLR inhibition could have protective effects in cardiovascular diseases as well as systemic and intragraft inflammatory responses that occur after cold ischemia-reperfusion in the setting of organ transplantation (Frantz S. et al. 2007 *Nature Clinical Practice* 4:444-454). Furthermore, high correlation was found between high TLR2 and TLR4 expression on circulating monocytes and liver transplantation recipients with acute rejection compared with those in clinically stable, normal liver function. These results suggested that activation of innate immunity in liver transplant recipients through TLR2 and TLR4 contributes to the development of acute allograft rejection after liver transplantation (Deng J. F. et al. 2007 *Transplant Proc.* 39:3222-3224).

Toll-like receptor antagonists, together with antibiotics, may delay or prevent infection-associated preterm birth. Pretreatment with TLR4 antagonist inhibited LPS-induced preterm uterine contractility, cytokines, and prostaglandins in rhesus monkeys (Waldorf K. M. et al. 2008 *Reprod Sci.* 15:121-127).

Recent studies show that TLRs are also expressed on a wide variety of tumors suggesting that TLRs may play important role in tumor progression. Activation of tumor cell TLRs not only promotes tumor cell proliferation and resistance to apoptosis, but also enhances tumor cell invasion and metastasis by regulating metalloproteinases and integrins. Moreover, the activation of TLR signaling in tumor cells induces the synthesis of proinflammatory factors and immunosuppressive molecules, which enhance the resistance of tumor cells to cytotoxic lymphocyte attack, leading to tumor evasion from immune surveillance. Thus, the neoplastic process seems to exploit TLR signaling pathways to advance cancer progression as well as immune evasion, suggesting that targeting tumor TLR signaling pathways may open novel therapeutic avenues (Huang B. et al., 2008 *Oncogene* 27:218-224).

Sepsis and septic shock, its more severe form, have shown alarming increases in incidence and a persistently high mortality rate, despite technological advancement allowing adequate support of vital functions in intensive care units. There is increasing evidence that TLRs play a key role in the mediation of systemic responses to invading pathogens during sepsis. Blockade of TLRs signaling suggests new potential therapeutic strategies for treating sepsis (Tsujimoto H. et al. 2008 *Shock* 29:315-321). Furthermore, HSPs, including gp96, can bind LPS directly, and are involved in the amplification of the immune response to endotoxin which takes place during sepsis (Triantafilou and Triantafilou 2004 *Biochem. Soc. Trans.* 32:636-639; Reed et al 2003 *J. Biol. Chem.* 278: 31853-31860).

To date, there are no known therapeutic agents which inhibit gp96. However, as demonstrated above, most investigative strategies are currently aimed at developing TLRs antagonists capable of inhibiting innate immune responses for the potential treatment of a vast array of immuno-regulated disorders. Another strategy is targeting CD91, the receptor for gp96. Small molecule inhibitors of CD91 or HSPs binding fragments of CD91 are being developed for the potential treatment of autoimmune disorders like multiple sclerosis, SLE and insulin dependent diabetes. Based on its critical role in the expression and function of various TLRs, antagonizing gp96 may be a more effective approach for the treatment of these disease conditions.

SUMMARY OF THE INVENTION

The subject invention now provides novel peptides corresponding to segments of gp96, homologs thereof, orthologs thereof, derivatives thereof, antibodies directed thereto, and fusion proteins comprising them, all of which have a therapeutic value for a wide range of conditions, disorders and diseases.

In one aspect of this invention the conditions, disorders and diseases are conditions, disorders and diseases selected from the group consisting of autoimmune diseases, sepsis, chronic and acute inflammatory diseases, gastrointestinal inflammatory diseases, gastrointestinal malignancies, diseases involving inflammation of the respiratory tract, auto-inflammatory diseases, ischemia-reperfusion injury related disorders, cardiovascular diseases, heavy metal induced diseases, kidney diseases, infectious diseases, cancer, preterm birth, complications of surgery and surgical interventions related to presence of endotoxin and bacterial infections, and acute allograft rejection after organ transplantation.

The subject invention thus provides a peptide consisting essentially of an amino acid sequence LNVSRETLQQH-KLLKVIRKKLVRKTLDMIKKIADDKY (CGEN-GP1 [SEQ ID NO: 1]) or a homolog or a derivative thereof.

The subject invention further provides a peptide consisting essentially of an amino acid sequence MMKLIIN-SLYKNKEIFLRELISNASDALDKIRLIS (CGEN-GP2 [SEQ ID NO: 2]) or a homolog or a derivative thereof.

The subject invention further provides a peptide consisting essentially of an amino acid sequence IYVWSSKTETVEEP-MEEEEAAKEEKEESDDEA (CGEN-GP3 [SEQ ID NO: 3]) or a homolog or a derivative thereof.

The subject invention further provides an isolated peptide consisting essentially of an amino acid sequence TLQQH-KLLKVIRKKLVRKTLDMIKKIADDKY (CGEN-GP4, SEQ ID NO: 27) or a derivative thereof.

The subject invention further provides an isolated peptide consisting essentially of an amino acid sequence HKLLKVIRKKLVRKTLDMIKKIADDKYNDTFWKEF (CGEN-GP5, SEQ ID NO: 29) or a derivative thereof.

The subject invention further provides an isolated peptide consisting essentially of an amino acid sequence KGVVDS-DDLPLNVSRETLQQHKLLKVIRKKLVRK-TLDMIKKIADDKYNDTFWKEFGT (SEQ ID NO: 4) or a derivative thereof.

The subject invention further provides an isolated peptide consisting essentially of an amino acid sequence KFAFQAE-VNRMMKLIINSLYKNKEIFLRELISNAS-DALDKIRLISLTDENALSGN (SEQ ID NO: 5) or a derivative thereof.

The subject invention further provides an isolated peptide consisting essentially of an amino acid sequence KKYSQFINFPIYVWSSKTETVEEP-MEEEEAAKEEKEESDDEAAVEEEEEEKK (SEQ ID NO: 6) or a derivative thereof.

The subject invention further provides an isolated peptide consisting essentially of an amino acid sequence DDLPLN-VSRETLQQHKLLKVIRKKLVRKTLDMIK-KIADDKYNDTFWKEFGT (SEQ ID NO: 31) or a derivative thereof.

The subject invention further provides an isolated peptide consisting essentially of an amino acid sequence LNVS-RETLQQHKLLKVIRKKLVRKTLDMIKKI-ADDKYNDTFWKEFGTNIKLGVIE (SEQ ID NO: 32) or a derivative thereof.

The subject invention further provides an isolated peptide consisting essentially of an amino acid sequence corresponding to a homolog of a peptide of the invention, consisting essentially of an amino acid sequence as set forth in any one of SEQ ID NOs: 14-24, 35-52.

The subject invention further provides a peptide consisting essentially of an amino acid sequence corresponding to a partner helix of a peptide of the invention.

The subject invention further provides a partner helix peptide consisting essentially of an amino acid sequence FLRELISNASDALDKIRLISLTDENALSGNEELTVKIK (SEQ ID NO: 25) or a homolog or a derivative thereof.

The subject invention further provides a partner helix peptide consisting essentially of an amino acid sequence INSLYKNKEIFLRELISNASDALDKIRL-ISLTDENALSGNEELTVKIKCDKEKNLLH V (SEQ ID NO: 26) or a homolog or a derivative thereof.

The subject invention also provides an antibody that selectively binds to an epitope in a peptide as set forth in any one of SEQ ID NOs: 1-6, 14-27, 29, 31 and 32.

The subject invention further provides a conjugate or fusion protein comprising a peptide of the invention as set forth in any one of SEQ ID NOs: 1-6, 14-27, 29, 31 and 32. The subject invention further provides a pharmaceutical composition comprising a peptide of the invention or a homolog thereof or a derivative thereof, an antibody of the invention or a fusion protein of the invention and a pharmaceutically acceptable carrier.

The subject invention further envisages a peptide of the invention or a homolog or a derivative thereof, an antibody of the invention or a fusion protein of the invention for use in therapy and further envisages a use of the peptide of the invention or a homolog or a derivative thereof, an antibody of the invention or a fusion protein of the invention for the manufacture of a medicament.

The subject invention further provides a method of treating sepsis, septic shock, endotoxin shock, endotoxinaemia, and/or systemic inflammatory response syndrome (SIRS) comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating an autoimmune disease comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating a gastrointestinal inflammatory disease comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating a gastrointestinal malignancy comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating a disease involving inflammation of the respiratory tract comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating an auto-inflammatory disease comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating an ischemia-reperfusion injury related disorder associated with ischemic and post-ischemic events in organs and tissues comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating a cardiovascular disease comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating a heavy metal induced disease comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating a kidney disease comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating an inflammatory disease comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method of treating an infectious disease caused by an intracellular pathogen comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method for treating cancer comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method for treating preterm birth and uterine contractility comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method for treating complications of surgery and surgical interventions related to presence of endotoxin and bacterial infections comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention further provides a method for treating acute allograft rejection after organ transplantation comprising administering a pharmaceutically effective amount of a peptide of the invention or a homolog thereof or a derivative thereof, an antibody of the invention, or a fusion protein of the invention and a pharmaceutically acceptable carrier to a subject in need thereof.

The subject invention also provides a nucleotide sequence encoding a peptide of the invention or a homolog thereof.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 17: demonstrates identification of helix-helix interactions using a unique computerized method. FIG. 17A presents the residue-residue contact map, corresponding to the two anti-parallel helices taken from BAG-1; FIG. 17B demonstrates a schematic view of two helices interacting through their adjacent faces.

FIG. 18: presents In Silico detection of a helix-helix interaction in gp96.

FIG. 20 presents, without being bound by theory, a potential mechanism of action of CGEN-GP1. FIG. 20A presents schematic diagram of a conformational change in a protein, and FIG. 20B shows the blockage of the conformational change in a protein by a peptide corresponding to one of the helices. FIG. 20C demonstrates that according to this potential mechanism of action, pre-incubation of the blocking peptide CGEN-GP1 (SEQ ID NO:1) with a peptide corresponding to its partner helix (SEQ ID NO:25) abolishes the inhibitory effect of CGEN-GP1 (SEQ ID NO:1). FIG. 20D presents the results of pre-incubation of 666 nM CGEN-GP1 peptide (SEQ ID NO:1) with an equimolar concentration of a peptide corresponding to a counterpart helix (SEQ ID NO:25).

FIG. 22: shows a multiple alignment comparison of the sequence of CGEN-GP1 (SEQ ID NO:1) and the orthologous sequences derived from >gi|15233740_0|[Arabidopsis thaliana], >gi|27807263_0|[Bos taurus], >gi|544242_0| [Hordeum vulgare], >gi|462013_0|[Catharanthus roseus], >gi|7865698_0|[Sus scrofa], >gi|45383562_0|[Gallus gallus], >gi|6015101_0|[Oryctolagus cuniculus], >gi|109098491_0|[Macaca fascicularis], >gi|6755863_0| [Mus musculus], >gi|75070529_0|[Pongo pygmaeus], >gi|50979166_0|[Canis familiaris], corresponding to SEQ ID NOs: 14-24.

FIG. 23 shows a multiple alignment comparison of the sequence of CGEN-GP4 (SEQ ID NO:27) and the orthologous sequences derived >gi:90076963 (Macaca fascicularis), >gi:37805386 (Xenopus laevis), >gi:403496 (Canis familiaris), >gi:74190331 (Mus musculus), >gi:39645914 (Danio rerio), >gi:210032364 (Rattus norvegicus) and >gi: 75775555 (Bos Taurus), corresponding to SEQ ID NOs: 35-41.

FIG. 24 shows a multiple alignment comparison of the sequence of CGEN-GP5 (SEQ ID NO:29) and the orthologous sequences derived from >gi:114646591_Pan troglodytes, >gi:109098490_Macaca mulatta, >gi:67970925_ Macaca fascicularis, >gi:55731899_Pongo abelii, >gi: 74190331_Mus musculus, >gi:210032364_Rattus norvegicus, >gi:75775555_Bos taurus, >gi:2239252_Sus scrofa, >gi:149742973_Equus caballus, >gi:403496_Canis familiaris and >gi:194220333_Gallus gallus, corresponding to SEQ ID NOs: 42-52.

DETAILED DESCRIPTION OF THE INVENTION

Figure 1:
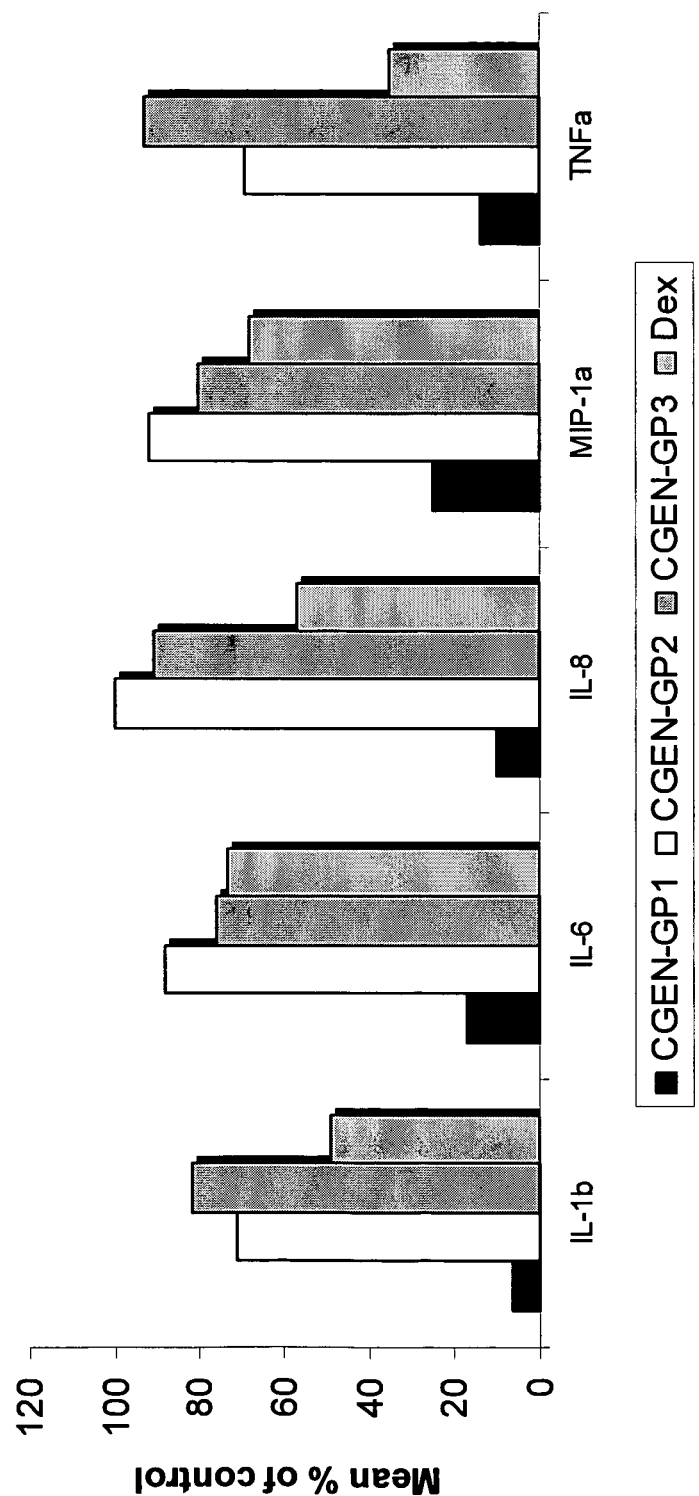
FIG. 1: presents the effect of CGEN-GP1 (SEQ ID NO:1), CGEN-GP2 (SEQ ID NO:2) and CGEN-GP3 (SEQ ID NO:3) (30 µg/ml=6 µM) on the release of anti CD3-induced cytokines IL-1b, IL6, IL-8, MIP-1α and TNFα from peripheral blood mononuclear cells (PBMCs). The concentration of the cytokines was measured using a Luminex analyzer (Luminex Corporation) and bead-based reagents (Upstate Biotechnology).

The subject invention provides a peptide consisting essentially of an amino acid sequence LNVSRETLQQH-KLLKVIRKKLVRKTLDMIKKIADDKY (CGEN-GP1 [SEQ ID NO: 1]) or a homolog or a derivative thereof. CGEN-GP1 corresponds to amino acid residues 444-480 of the gp96 protein sequence (GenBank Accession number: gi|4507677).

The subject invention further provides a peptide consisting essentially of an amino acid sequence MMKLIIN-SLYKNKEIFLRELISNASDALDKIRLIS (CGEN-GP2 [SEQ ID NO: 2]) or a homolog or a derivative thereof. CGEN-GP2 corresponds to amino acid residues 85-119 of the gp96 protein sequence (GenBank Accession number: gi|4507677).

The subject invention further provides a peptide consisting essentially of an amino acid sequence IYVWSSKTETVEEP-MEEEEAAKEEKEESDDEA (CGEN-GP3 [SEQ ID NO: 3]) or a homolog or a derivative thereof. CGEN-GP3 corresponds to amino acid residues 279-310 of the gp96 protein sequence (GenBank Accession number: gi|4507677).

The subject invention further provides a peptide consisting essentially of an amino acid sequence TLQQH-KLLKVIRKKLVRKTLDMIKKIADDKY (CGEN-GP4 [SEQ ID NO: 27]) or a homolog or a derivative thereof. CGEN-GP4 corresponds to amino acid residues 450-480 of the gp96 protein sequence (GenBank Accession number: gi|4507677).

The subject invention further provides a peptide consisting essentially of an amino acid sequence HKLLKVIRKKLVRKTLDMIKKIADDKYNDTFWKEF (CGEN-GP5 [SEQ ID NO: 29]) or a homolog or a derivative thereof. CGEN-GP5 corresponds to amino acid residues 454-488 of the gp96 protein sequence (GenBank Accession number: gi|4507677).

The term "homolog" relating to a peptide of the invention as used herein should be understood to encompass a peptide which has substantially the same amino acid sequence and substantially the same biological activity as CGEN-GP1, CGEN-GP2, CGEN-GP3, CGEN-GP4, or CGEN-GP5, respectively. Thus, a homolog may differ from the CGEN-GP1, CGEN-GP2, CGEN-GP3, CGEN-GP4, or CGEN-GP5 peptides by the addition, deletion or substitution of one or more amino acid residues, provided that the resulting peptide retains the biological activity of CGEN-GP1, CGEN-GP2, CGEN-GP3, CGEN-GP4, or CGEN-GP5, respectively. Persons skilled in the art can readily determine which amino acid residues may be added, deleted or substituted (including with which amino acids such substitutions may be made) using established well known procedures. Examples of homologs of CGEN-GP1, CGEN-GP2, CGEN-GP3, CGEN-GP4, or CGEN-GP5 are deletion homologs containing less than all the amino acid residues of CGEN-GP1, CGEN-GP2, CGEN-GP3, CGEN-GP4, or CGEN-GP5, substitution homologs wherein one or more amino acid residues specified are replaced by other amino acid residues (eg. amino acid with similar properties or by D-amino acids, or by non-natural amino acids) and addition homologs wherein one or more amino acid residues are added to a terminal or medial portion of CGEN-GP1, CGEN-GP2, CGEN-GP3, CGEN-GP4, or CGEN-GP5, all of which share the biological activity of CGEN-GP1, CGEN-GP2, CGEN-GP3, CGEN-GP4, or CGEN-GP5.

In one embodiment, a homolog of a CGEN-GP1 peptide of the invention is KGVVDSDDLPLNVSRETLQQH-KLLKVIRKKLVRKTLDMIKKIADDKYNDTFWK EFGT [SEQ ID NO: 4] which corresponds to amino acid residues 434-490 of gp96 protein sequence (GenBank Accession number: gi|4507677, SEQ ID NO:13).

In another embodiment, a homolog of a CGEN-GP2 peptide of the invention is KFAFQAEVNRMMKLIIN-SLYKNKEIFLRELISNASDALDKIRLISLTDENALSGN [SEQ ID NO: 5] which corresponds to amino acid residues 75-129 of gp96 protein sequence (GenBank Accession number: gi|4507677, SEQ ID NO:13).

In another embodiment, a homolog of a CGEN-GP3 peptide of the invention is KKYSQFINFPIYVWSSK-TETVEEPMEEEEAAKEEKEESDDEAAVEEEEEEKK [SEQ ID NO: 6] which corresponds to amino acid residues 269-320 of gp96 protein sequence (GenBank Accession number: gi|4507677, SEQ ID NO:13).

In another embodiment, a homolog of a CGEN-GP4 peptide of the invention is DDLPLNVSRETLQQH-KLLKVIRKKLVRKTLDMIKKIADDKYNDTFWKEFGT [SEQ ID NO: 31] which corresponds to amino acid residues 440-490 of gp96 protein sequence (GenBank Accession number: gi|4507677, SEQ ID NO:13).

In another embodiment, a homolog of a CGEN-GP5 peptide of the invention is LNVSRETLQQH-KLLKVIRKKLVRKTLDMIKKIAD-DKYNDTFWKEFGTNIKLGVIE [SEQ ID NO: 32] which corresponds to amino acid residues 444-498 of gp96 protein sequence (GenBank Accession number: gi|4507677, SEQ ID NO:13).

The term "homolog" relating to a peptide of the invention as used herein should also be understood to encompass an ortholog. The term "ortholog" should be understood to encompass a peptide derived from a non-human origin which has substantially the same amino acid sequence and substantially the same biological activity as CGEN-GP1, CGEN-GP2, CGEN-GP3, CGEN-GP4, or CGEN-GP5.

The subject invention further provides an isolated peptide being an ortholog of CGEN-GP1 [SEQ ID NO: 1], consisting essentially of an amino acid sequence as depicted in any one of SEQ ID NOs:14-24, or a derivative thereof.

The subject invention further provides an isolated peptide being an ortholog of CGEN-GP1 [SEQ ID NO: 4], consisting essentially of an amino acid sequence as depicted in any one of SEQ ID NOs: 35-41, or a derivative thereof.

The subject invention further provides an isolated peptide being an ortholog of CGEN-GP1 [SEQ ID NO: 5], consisting essentially of an amino acid sequence as depicted in any one of SEQ ID NOs: 42-52, or a derivative thereof.

The term "partner helix (peptide)" as used herein should be understood to encompass a peptide corresponding to an alpha helix within the parent gp96 protein, which physically interacts with a peptide of the invention.

The subject invention thus further provides a peptide consisting essentially of an amino acid sequence corresponding to a partner helix of a peptide of the invention or a homolog or a derivative thereof.

The subject invention provides a peptide consisting essentially of an amino acid sequence corresponding to a partner helix of a peptide having an amino acid sequence as depicted in SEQ ID NO: 1.

The subject invention further provides a peptide consisting essentially of an amino acid sequence FLRELISNASDALD-KIRLISLTDENALSGNEELTVKIK (SEQ ID NO:25), corresponding to a partner helix of CGEN-GP1 (SEQ ID NO: 1). This peptide SEQ ID NO:25 corresponds to amino acid residues 100-137 of the gp96 protein sequence (GenBank Accession number: gi|4507677_0|[Homo sapiens]|ENPL_HUMAN, SEQ ID NO: 13).

The subject invention further provides a peptide consisting essentially of an amino acid sequence INSLYKNKEIFL-RELISNASDALDKIRLISLTDENALS-GNEELTVKIKCDKEKNLLH V (SEQ ID NO:26), corresponding to an elongated partner helix of CGEN-GP1 (SEQ ID NO: 1). This peptide SEQ ID NO:26 corresponds to amino acid residues 90-147 of the gp96 protein sequence (GenBank Accession number: gi|4507677_0|[Homo sapiens]|ENPL_HUMAN, SEQ ID NO: 13).

The subject invention further provides an antibody that selectively binds to an epitope within a peptide of the invention. In one embodiment, said epitope is located in a peptide of the invention as depicted in any one of SEQ ID NOs: 1-3, 27, or 29. In another embodiment, said epitope is located in a peptide of the invention as depicted in any one of SEQ ID NOs: 4-6, 31 or 32. In another embodiment, said epitope is located in a peptide of the invention, as depicted in any one of SEQ ID NOs:14-24 or 35-52. In yet another embodiment, said epitope is located in a peptide of the invention as depicted in any one of SEQ ID NOs: 25-26.

The subject invention further provides an antibody that selectively binds to an epitope in a helix-helix structure derived from the interaction of a peptide of the invention with a corresponding partner helix.

The subject invention further provides a conjugate or fusion protein comprising a peptide of the invention as set forth in any one of SEQ ID NOs: 1-6, 14-27, 29, 31-32, 35-52.

All amino acid sequences and nucleic acid sequences shown herein as embodiments of the present invention relate to their isolated form.

Non-natural amino acids are known to those skilled in the art of chemical synthesis and peptide chemistry. Non-limiting examples of non-natural amino acids (each one in L- or D-configuration) are azidoalanine, azidohomoalanine, 2-amino-5-hexynoic acid, norleucine, azidonorleucine, L-a-aminobutyric acid, 3-(1-naphthyl)-alanine, 3-(2-naphthyl)-alanine, p-ethynyl-phenylalanine, m-ethynyl-phenylalanine, p-ethynyl-phenylalanine, p-bromophenylalanine, p-idiophenylalanine, p-azidophenylalanine, 3-(6-chloroindolyl)alanin and those listed in Table 1 below.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |

TABLE 1-continued

| Non-conventional amino acid | Code | Non-conventional amino acid | Code |
|---|---|---|---|
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The term "derivative" relating to a peptide of the invention should be understood to encompass a peptide which has substantially the same amino acid sequence and substantially the same biological activity as CGEN-GP1, CGEN-GP2, CGEN-GP3, CGEN-GP4, or CGEN-GP5. Thus, a derivative may differ from the CGEN-GP1, CGEN-GP2, CGEN-GP3, CGEN-GP4, or CGEN-GP5 peptide by a modification, such as but not limited to glycosylation, amidation, acetylation, alkylation, alkenylation, alkynylation, phosphorylation, sulphorization, hydroxylation, hydrogenation, cyclization and so forth. Thus, a derivative of a peptide of the invention may differ from the CGEN-GP1, CGEN-GP2, CGEN-GP3, CGEN-GP4, or CGEN-GP5 peptide by a modification on one or more amino acid residues, provided that the resulting peptide retains the biological activity of CGEN-GP1, CGEN-GP2, CGEN-GP3, CGEN-GP4, or CGEN-GP5, respectively.

Persons skilled in the art can readily determine which amino acid residues may be modified using established well known procedures. In one embodiment, a peptide of the invention is amidated at its C-terminus and acetylated at its N-terminus.

"A peptide with substantially the same amino acid sequence as CGEN-GP1" as used herein should be understood to encompass a synthetic peptide which has at least 5, preferably at least 8 and at most 57 amino acids, which correspond to a sequential fragment of amino acids 434-490 of gp96 protein sequence (GenBank Accession number: gi|4507677, SEQ ID NO: 13).

"A peptide with substantially the same amino acid sequence as CGEN-GP2" as used herein should be understood to encompass a synthetic peptide which has at least 5, preferably at least 8 and at most 55 amino acids, which correspond to a sequential fragment of amino acids 75-129 of gp96 protein sequence (GenBank Accession number: gi|4507677, SEQ ID NO:13).

"A peptide with substantially the same amino acid sequence as CGEN-GP3" as used herein should be understood to encompass a synthetic peptide which has at least 5, preferably at least 8 and at most 52 amino acids, which correspond to a sequential fragment of amino acids 269-320 of gp96 protein sequence (GenBank Accession number: gi|4507677, SEQ ID NO:13)

"A peptide with substantially the same amino acid sequence as CGEN-GP4" as used herein should be understood to encompass a synthetic peptide which has at least 5, preferably at least 8 and at most 51 amino acids, which correspond to a sequential fragment of amino acids 440-490 of gp96 protein sequence (GenBank Accession number: gi|4507677, SEQ ID NO:13).

"A peptide with substantially the same amino acid sequence as CGEN-GP5" as used herein should be understood to encompass a synthetic peptide which has at least 5, preferably at least 8 and at most 55 amino acids, which correspond to a sequential fragment of amino acids 444-498 of gp96 protein sequence (GenBank Accession number: gi|4507677, SEQ ID NO:13).

"A peptide with substantially the same biological activity as CGEN-GP1, CGEN-GP2, CGEN-GP3, CGEN-GP4, or CGEN-GP5" as used herein should be understood to encompass a peptide which has at least 80% of the biological activity of CGEN-GP1, CGEN-GP2, CGEN-GP3, CGEN-GP4, or CGEN-GP5, respectively.

A peptide of the invention may be prepared synthetically (e.g. on a solid support by solid phase peptide synthesis or in solution) or by recombinant means (in bacteria, yeast, fungi, insect, vertebrate or mammalian cells) by methods well known to those skilled in the art.

In one embodiment, a peptide of the invention may be synthesized such that one or more of the bonds which link the amino acid residues of the peptide, are non-peptide bonds.

In another embodiment, a peptide of the invention may be synthesized with additional chemical groups, such that, for example, the stability, bioavailability, and/or inhibitory activity of the peptide is modified. For example, an acetyl group may be placed at the amino termini of a peptide of the invention. Additionally or alternatively, an amido group may be added to the carboxy termini of a peptide of the invention.

In yet another embodiment, a peptide of the invention may be synthesized with an altered steric configuration. For example, the D-isomer of one or more of the amino acid residues of a peptide of the invention may be used, rather than the usual L-isomer.

In yet a further embodiment, at least one of the amino acid residues of a peptide of the invention may be substituted by any one of the well known non-naturally occurring amino acid residues, selected from, but not limited to azidoalanine, azidohomoalanine, 2-amino-5-hexynoic acid, norleucine, azidonorleucine, L-a-aminobutyric acid, 3-(1-naphthyl)-alanine, 3-(2-naphthyl)-alanine, p-ethynyl-phenylalanine, m-ethynyl-phenylalanine, p-ethynyl-phenylalanine, p-bromophenylalanine, p-idiophenylalanine, p-azidophenylalanine, 3-(6-chloroindolyl)alanin and those from Table 1 herein.

In another embodiment, a peptide of the invention may have a non-peptide macromolecular carrier group covalently attached to its amino and/or carboxy terminus. Non-limiting examples of such macromolecular carrier groups are proteins, lipid-fatty acid conjugates, polyethylene glycol, and carbohydrates.

The subject invention further provides a pharmaceutical composition comprising a peptide of the invention or a homolog or a derivative thereof and a pharmaceutically acceptable carrier. The subject invention also provides a pharmaceutical composition comprising an antibody of the invention and a pharmaceutically acceptable carrier. The subject invention additionally provides a pharmaceutical composition comprising a fusion protein of the invention and a pharmaceutically acceptable carrier.

Suitable routes of administration of a peptide or pharmaceutical composition comprising a peptide of the subject invention are oral, rectal, pulmonary (e.g. inhalation), nasal, topical (including transdermal, buccal and sublingual), vaginal, brain delivery (e.g. intra-cerebroventricular, intra-cerebral, and convection enhanced diffusion), CNS delivery (e.g. intrathecal, perispinal, and intra-spinal) or parenteral (including subcutaneous, intramuscular, intravenous and intradermal) administration or administration via an implant. In a specific embodiment, a peptide or a pharmaceutical composition comprising a peptide of the invention can be administered intravenously.

The exact dose and regimen of administration of a peptide or pharmaceutical composition comprising a peptide of the invention will necessarily be dependent upon the therapeutic effect to be achieved (e.g. treatment of an auto-immune disease) and may vary with the particular compound, the route of administration, and the age and condition of the individual subject to whom the medicament is to be administered.

A dosage for humans is likely to contain 0.1-10 mg per kg body weight per day. The desired dose may be presented as one dose or as multiple sub-doses administered at appropriate intervals.

The present invention thus also relates to a pharmaceutical composition comprising a peptide of the subject invention or a homolog or derivative thereof (or comprising an antibody thereto or comprising a fusion protein comprising a peptide of the invention) in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal, parenteral (including subcutaneous, intramuscular, intravenous and intradermal), or pulmonary (inhalation) administration, brain delivery (including intra-cerebroventricular, intra-cerebral, and convection enhanced diffusion), CNS delivery (including intrathecal, perispinal, intra-spinal) or administration via an implant. The compositions may be prepared by any method well known in the art of pharmacy.

Such methods include the step of bringing in association a peptide of the invention with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The subject invention further provides a use of a peptide of the invention or a homolog or derivative thereof for the manufacture of a medicament. The subject invention also provides an antibody of the invention for the manufacture of a medicament. The subject invention additionally provides a fusion protein of the invention for the manufacture of a medicament. The subject invention also provides a peptide of the invention or a homolog or derivative thereof for use in therapy. The subject invention also provides an antibody of the invention for use in therapy. The subject invention additionally provides a fusion protein of the invention for use in therapy.

In one embodiment, the medicament or therapy is for the treatment of sepsis, septic shock, endotoxin shock, endotoxinaemia, and systemic inflammatory response syndrome (SIRS).

In another embodiment, the medicament or therapy is for the treatment of an autoimmune disease.

The term "autoimmune disease" as used herein should be understood to encompass any autoimmune disease. Non-limiting examples of autoimmune diseases which may be treated with a peptide of the invention are multiple sclerosis, psoriasis, rheumatoid arthritis, systemic lupus erythematosus (SLE), ulcerative colitis, Crohn's disease, immune disorders associated with graft transplantation rejection, benign lymphocytic angiitis, lupus erythematosus, Hashimoto's autoimmune thyroiditis, primary myxedema, Graves' disease, pernicious anemia, autoimmune atrophic gastritis, Addison's disease, insulin dependent diabetes, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myocarditis, myositis, myogelosis, chondrocalcinosis, inflammatory bowel disease (IBD), autoimmune hepatitis, autoimmune myocarditis, and type 1 diabetes.

In a specific embodiment, the autoimmune disease is selected from the group consisting of ankylosing spondylitis, psoriasis, inflammatory bowel disease (IBD), Crohn's disease, ulcerative colitis, systemic lupus erythematosus (SLE), Sjogren's syndrome, multiple sclerosis, rheumatoid arthritis, autoimmune hepatitis, autoimmune myocarditis, Hashimoto's autoimmune thyroiditis, and type 1 diabetes.

In yet another embodiment, the medicament or therapy is for the treatment of a gastrointestinal inflammatory disease.

The term "gastrointestinal inflammatory disease" as used herein should be understood to encompass any gastrointestinal inflammatory disease. Non-limiting examples of gastrointestinal inflammatory diseases which may be treated with a peptide of the invention are Barret's esophagus, chronic gastritis, gastric ulcers, gastroenteritis, ulcerative colitis, pancolitis, inflammatory bowel disease (IBD), and Crohn's disease.

In yet another embodiment, the medicament or therapy is for the treatment of a gastrointestinal malignancy.

The term "gastrointestinal malignancy" as used herein should be understood to encompass any gastrointestinal malignancy. Non-limiting examples of gastrointestinal malignancies which may be treated with a peptide according to the invention are gastric cancer, small intestinal cancer, colorectal carcinoma, and esophageal adenocarcinoma.

In yet another embodiment, the medicament or therapy is for the treatment of a disease involving inflammation of the respiratory tract.

The term "a disease involving inflammation of the respiratory tract" as used herein should be understood to encompass any disease involving inflammation of the respiratory tract. Non-limiting examples of a disease involving inflammation of the respiratory tract which may be treated with a peptide according to the invention are asthma, allergy, pulmonary emphysema, pulmonary inflammation, environmental airway disease, airway hyper-responsiveness, chronic bronchitis, acute lung injury, bronchial disease, lung diseases, cystic fibrosis, chronic obstructive pulmonary disease (COPD), acute respiratory distress syndrome (ARDS), and severe acute respiratory syndrome (SARS).

In yet another embodiment, the medicament or therapy is for the treatment of an autoinflammatory disease.

The term "autoinflammatory disease" as used herein should be understood to encompass any autoinflammatory disease. Non-limiting examples of an autoinflammatory disease which may be treated with a peptide of the invention are normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, and TNF receptor-associated periodic syndrome (TRAPS).

In yet another embodiment, the medicament or therapy is for the treatment of an ischemia-reperfusion injury related disorder associated with ischemic and post-ischemic events in organs and tissues.

The term "an ischemia-reperfusion injury related disorder associated with ischemic and post-ischemic events in organs and tissues" as used herein should be understood to encompass any an ischemia-reperfusion injury related disorder associated with ischemic and post-ischemic events in organs and tissues. Non-limiting examples of an ischemia-reperfusion injury related disorder associated with ischemic and post-ischemic events in organs and tissues which may be treated with a peptide of the invention are thrombotic stroke, myocardial infarction, angina pectoris, embolic vascular occlusions, peripheral vascular insufficiency, splanchnic artery occlusion, arterial occlusion by thrombi or embolisms, arterial occlusion by non-occlusive processes such as following low mesenteric flow or sepsis, mesenteric arterial occlusion, mesenteric vein occlusion, ischemia-reperfusion injury to the mesenteric microcirculation, ischemic acute renal failure, ischemia-reperfusion injury to the cerebral tissue, intestinal intussusception, hemodynamic shock, tissue dysfunction, organ failure, restenosis, atherosclerosis, thrombosis, platelet aggregation, or disorders resulting from procedures such as angiography, cardiopulmonary and cerebral resuscitation, cardiac surgery, organ surgery, organ transplantation, and systemic and intragraft inflammatory responses that occur after cold ischemia-reperfusion in the setting of organ transplantation.

In yet another embodiment, the medicament or therapy is for the treatment of a cardiovascular disease.

The term "cardiovascular disease" as used herein should be understood to encompass any cardiovascular disease. Non-limiting examples of cardiovascular diseases which may be treated with a peptide of the invention are peripheral vascular diseases and coronary artery diseases such as coronary heart disease, myocardial infarction, heart injury, congestive heart failure, cardiac dysfunction in sepsis, myocardial failure, myocardial hypertrophy, ischemic cardiomyopathy, stroke, thrombotic stroke, myocarditis, cardiomyopathy, myocarditis, decompensated heart failure, ischemic myocardial disease, congenital heart disease, angina pectoris, ischemia—reperfusion injury in ischemic and post-ischemic events, cerebrovascular accident, fibrosis, platelet aggregation, atherosclerosis, thrombosis, restenosis after coronary intervention, and intimal hyperplasia, arteriogenesis.

In yet another embodiment, the medicament or therapy is for the treatment of a heavy metal induced disease.

The term "a heavy metal induced disease" as used herein should be understood to encompass any heavy metal induced disease. Non-limiting examples of such diseases which may be treated by a peptide according to the invention are lead, zinc and cadmium poisoning.

In yet another embodiment, the medicament or therapy is for the treatment of a kidney disease.

The term "kidney disease" as used herein should be understood to encompass any kidney disease. Non-limiting examples of such diseases which may be treated by a peptide according to the invention are nephropathy, nephritis, bacterial pyelonephritis, glomerulonephritis, lupus nephritis, acute and chronic renal failure, and renal vascular disease.

In yet another embodiment, the medicament or therapy is for the treatment of an inflammatory disease.

The term "inflammatory disease" as used herein should be understood to encompass any inflammatory disease. Non-limiting examples of such diseases which may be treated by a peptide according to the invention are gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

Without being bound by theory, inflammatory disease refers to conditions mediated by cells of the lymphoid lineage, including but not limited to T cells, B cells, and natural killer (NK) cells, and cells of the myeloid lineage, including but not limited to dendritic cells and myeloid suppressor cells. Without being bound by theory, peptides of the invention inhibit the cytotoxic activity induced by NK cells, have an effect on the expression of costimulatory molecules on the surface of dendritic cells, inhibit the maturation of the dendritic cells and/or attenuate the inhibitory effect induced by myeloid suppressor cells. Peptides of the invention reduce the circulating levels of inflammatory cytokines such as, but not limited to, IL-1beta, TNFalpha, IL-6 and inflammatory chemokines such as, but not limited to, MIP2 and MIP1alpha secreted from these cells.

In yet another embodiment, the medicament or therapy is for the treatment of an infectious disease including those caused by intracellular pathogens such as viruses, bacteria, protozoans and intracellular parasites.

An infectious disease as used herein should be understood to encompass any infectious disease. Non-limiting examples of such diseases which may be treated with a peptide according to the invention are viral, bacterial and protozoal infectious diseases.

Non-limiting examples of viral diseases which may be treated by a peptide according to the invention are hepatitis type B virus, hepatitis type C virus, hepatitis type A virus, parvoviruses such as adeno-associated virus and cytomegalovirus, papovaviruses such as papilloma virus, polyoma viruses, SV40, adenoviruses, herpes viruses such as herpes simplex type I (HSV-I), herpes simplex type II (HSV-II), and Epstein-Barr virus (EBV), poxviruses such as variola (smallpox) and vaccinia virus, RNA viruses including but not limited to human immunodeficiency virus type I (HIV-I), human immunodeficiency virus type II (HIV-II), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus and Semliki forest virus, and arboviruses.

Non-limiting examples of bacterial infections which may be treated or prevented with a peptide of the invention are *Streptococcus pyogenes, Streptococcus pneumoniae, Neisseria gonorrhoea, Neisseria meningitides, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Vacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhiimurium, Salmonella typhii, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma spp., Rickettsia prowazeki, Rickettsia tsutsugumushi, Chlamydia spp.,* and *Helicobacter pylori.*

Non-limiting examples of protozoal infections which may be treated or prevented with a peptide of the invention are *Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum,* and *Plasmodium malaria.*

In yet another embodiment, the medicament or therapy is for the treatment of cancer.

The term "therapy for cancer" or "treating cancer" as used herein should be understood to encompass achieving: a decrease in tumor size; a decrease in rate of tumor growth; a decrease in tumor migration; a decrease in tumor epithelial-to-mesenchymal transition (EMT); stasis of tumor size; a decrease in invasiveness of the cancer; a decrease in the rate of progression of the tumor from one stage to the next; inhibition of tumor growth in a tissue of a mammal having a malignant cancer; a decrease in the number of metastasis; a decrease in the number of additional metastasis; control of establishment of metastases; inhibition of tumor metastases formation; regression of established tumors as well as decrease in the angiogenesis induced by the cancer. The term "therapy for cancer" and "treating cancer" as used herein should also be understood to encompass prophylaxis such as prevention as cancer reoccurs after previous treatment (including surgical removal) and prevention of cancer in an individual prone to develop cancer. Subjects may be prone to develop cancer genetically or due to life style, chronic inflammation, hepatitis C(HCV), inflammatory bowel disease (IBD) and so forth.

The term "cancer" as used herein should be understood to encompass any neoplastic disease (whether invasive or metastatic) which is characterized by abnormal and uncontrolled cell division causing malignant growth or tumor. Non-limiting examples of cancer which may be treated with a peptide of the invention are breast cancer (e.g. breast carcinoma), cervical cancer, ovary cancer (ovary carcinoma), endometrial cancer, melanoma, bladder cancer (bladder carcinoma), lung cancer (e.g. adenocarcinoma and including non-small cell lung cancer), pancreatic cancer (e.g. pancreatic carcinoma such as, for example exocrine pancreatic carcinoma), colon cancer (e.g. colorectal carcinoma, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemia (for example, acute myelogenous leukemia (AML)), thyroid follicular cancer, myelodysplastic syndrome (MDS), tumors of mesenchymal origin (e.g. fibrosarcomas and rhabdomyosarcomas), melanoma, teratocarcinoma, neuroblastoma, glioma, glioblastoma, benign tumor of the skin (e.g. keratoacanthomas), renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, and epidermal carcinoma.

In a specific embodiment, the cancer is selected from the group consisting of solid tumors, sarcomas, hematological malignancies including but not limited to leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate cancer, lung cancer, ovary cancer, colon cancer, spleen cancer, kidney cancer, bladder cancer, head and neck cancer, cervical cancer, testicle cancer, stomach cancer, liver cancer, bone cancer, skin cancer, melanoma, pancreatic cancer, and brain cancer.

In another embodiment, the cancer is inflammation-induced cancer.

One of the mechanisms for tumorigenesis (the process involved in the production of a new tumor or tumors) is induced by chronic inflammation (Pikarsky E, et al., Nature 2004 Sep. 23; 431(7007):461-6; Moss S F, Blaser M J. Nat Clin Pract Oncol. 2005 February; 2(2):90-7; Karin M, Greten F R. Nat Rev Immunol. 2005 October; 5(10):749-59.) Chronic inflammation is also a mechanism for tumor maintenance.

Without being bound by theory, when used against inflammatory diseases and inflammatory environments that support tumorigenesis and the various steps of tumor progression including invasiveness, migration, epithelial-to-mesenchymal transition (EMT), and metastasis, peptides of the invention reduce the circulating levels of inflammatory cytokines such as, but not limited to, IL-1beta, TNFalpha, IL-6 and inflammatory chemokines such as, but not limited to, MIP2 and MIP1alpha.

Peptides of the invention attenuate inflammation-induced tumorigenesis and tumor maintenance.

In one embodiment, the cancer is invasive. In another embodiment, the cancer is metastatic.

In another embodiment, the tumor metastasis originated from a melanoma, breast cancer, colorectal cancer, prostate cancer or lung cancer.

The treatment of metastatic cancer with a peptide of the invention is tested in model systems of melanoma, colorectal cancer, breast cancer, prostate cancer and/or lung cancer.

In yet another embodiment, the medicament or therapy is for the treatment of preterm birth, particularly infection-associated and uterine contractility.

In yet another embodiment, the medicament or therapy is for the treatment of complications of surgery and surgical interventions related to presence of endotoxin and bacterial infections.

In yet another embodiment, the medicament or therapy is for the treatment of acute allograft rejection after organ transplantation.

The subject invention further provides a method of treating sepsis, septic shock, endotoxin shock, endotoxinaemia, and/or systemic inflammatory response syndrome (SIRS) comprising administering a pharmaceutically effective amount of a peptide according to the invention or a homolog or a derivative thereof and a pharmaceutically acceptable carrier to a subject in need thereof. The subject invention further provides a method of treating sepsis, septic shock, endotoxin shock, endotoxinaemia, and/or systemic inflammatory response syndrome (SIRS) comprising administering a pharmaceutically effective amount of an antibody of the invention and a pharmaceutically acceptable carrier to a subject in need thereof. The subject invention also provides a method of treating sepsis, septic shock, endotoxin shock, endotoxinaemia, and/or systemic inflammatory response syndrome (SIRS) comprising administering a pharmaceutically effective amount of a fusion protein of the invention and a pharmaceutically acceptable carrier to a subject in need thereof.

The subject invention further provides a method of treating an autoimmune disease comprising administering a pharmaceutically effective amount of a peptide according to the invention or a homolog or a derivative thereof and a pharmaceutically acceptable carrier to a subject in need thereof. The subject invention further provides a method of treating an autoimmune disease comprising administering a pharmaceutically effective amount of an antibody of the invention and a pharmaceutically acceptable carrier to a subject in need thereof. The subject invention also provides a method of treating an autoimmune disease comprising administering a pharmaceutically effective amount of a fusion protein of the invention and a pharmaceutically acceptable carrier to a subject in need thereof.

In one embodiment, the autoimmune disease is selected from the group consisting of multiple sclerosis, psoriasis, rheumatoid arthritis, systemic lupus erythematosus (SLE), ulcerative colitis, Crohn's disease, immune disorders associated with graft transplantation rejection, benign lymphocytic angiitis, lupus erythematosus, Hashimoto's autoimmune thyroiditis, primary myxedema, Graves' disease, pernicious anemia, autoimmune atrophic gastritis, Addison's disease, insulin dependent diabetes, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myocarditis, myositis, myogelosis, chondrocalcinosis, inflammatory bowel disease (IBD), autoimmune hepatitis, autoimmune myocarditis and type 1 diabetes.

In another embodiment, the autoimmune disease is selected from the group consisting of ankylosing spondylitis, psoriasis, inflammatory bowel disease (IBD), Crohn's disease, ulcerative colitis, systemic lupus erythematosus (SLE), Sjogren's syndrome, multiple sclerosis, rheumatoid arthritis, autoimmune hepatitis, autoimmune myocarditis, Hashimoto's autoimmune thyroiditis, and type 1 diabetes.

The subject invention further provides a method of treating a gastrointestinal inflammatory disease comprising administering a pharmaceutically effective amount of a peptide according to the invention or a homolog or a derivative thereof and a pharmaceutically acceptable carrier to a subject in need thereof. The subject invention further provides a method of treating a gastrointestinal inflammatory disease comprising administering a pharmaceutically effective amount of an antibody of the invention and a pharmaceutically acceptable carrier to a subject in need thereof. The subject invention also provides a method of treating a gastrointestinal inflammatory disease comprising administering a pharmaceutically effective amount of a fusion protein of the invention and a pharmaceutically acceptable carrier to a subject in need thereof.

In one embodiment, the gastrointestinal inflammatory disease is selected from the group consisting of Barret's esophagus, chronic gastritis, gastric ulcers, gastroenteritis, ulcerative colitis, pancolitis, inflammatory bowel disease (IBD) and Crohn's disease.

The subject invention further provides a method of treating a gastrointestinal malignancy comprising administering a pharmaceutically effective amount of a peptide according to the invention or a homolog or a derivative thereof and a pharmaceutically acceptable carrier to a subject in need thereof. The subject invention further provides a method of treating a gastrointestinal malignancy comprising administering a pharmaceutically effective amount of an antibody of the invention and a pharmaceutically acceptable carrier to a subject in need thereof. The subject invention also provides a method of treating a gastrointestinal malignancy comprising administering a pharmaceutically effective amount of a fusion protein of the invention and a pharmaceutically acceptable carrier to a subject in need thereof.

In one embodiment, the gastrointestinal malignancy is selected from the group consisting of gastric cancer, small intestinal cancer, colorectal carcinoma and esophageal adenocarcinoma.

The subject invention further provides a method of treating a disease involving inflammation of the respiratory tract comprising administering a pharmaceutically effective amount of a peptide according to the invention or a homolog or a derivative thereof and a pharmaceutically acceptable carrier to a subject in need thereof. The subject invention further provides a method of treating a disease involving inflammation of the respiratory tract comprising administering a pharmaceutically effective amount of an antibody of the invention and a pharmaceutically acceptable carrier to a subject in need thereof. The subject invention also provides a method of treating a disease involving inflammation of the respiratory tract comprising administering a pharmaceutically effective amount of a fusion protein of the invention and a pharmaceutically acceptable carrier to a subject in need thereof.

In one embodiment, the disease involving inflammation of the respiratory tract is selected from the group consisting of asthma, allergy, pulmonary emphysema, pulmonary inflammation, environmental airway disease, airway hyper-responsiveness, chronic bronchitis, acute lung injury, bronchial disease, lung diseases, cystic fibrosis, chronic obstructive pulmonary disease (COPD), acute respiratory distress syndrome (ARDS) and severe acute respiratory syndrome (SARS).

The subject invention further provides a method of treating an autoinflammatory disease comprising administering a pharmaceutically effective amount of a peptide according to the invention or a homolog or a derivative thereof and a pharmaceutically acceptable carrier to a subject in need thereof. The subject invention further provides a method of treating an autoinflammatory disease comprising administering a pharmaceutically effective amount of an antibody of the invention and a pharmaceutically acceptable carrier to a subject in need thereof. The subject invention also provides a method of treating an autoinflammatory disease comprising administering a pharmaceutically effective amount of a fusion protein of the invention and a pharmaceutically acceptable carrier to a subject in need thereof.

In one embodiment, the auto-inflammatory disease is selected from the group consisting of normocomplementemic urticarial vasculitis, pericarditis, myositis, anti-synthetase syndrome, scleritis, macrophage activation syndrome, Bechet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, and TNF receptor-associated periodic syndrome (TRAPS).

The subject invention further provides a method of treating an ischemia-reperfusion injury related disorder associated with ischemic and post-ischemic events in organs and tissues comprising administering a pharmaceutically effective amount of a peptide according to the invention or a homolog or a derivative thereof and a pharmaceutically acceptable carrier to a subject in need thereof. The subject invention further provides a method of treating an ischemia-reperfusion injury related disorder associated with ischemic and post-ischemic events in organs and tissues comprising administering a pharmaceutically effective amount of an antibody of the invention and a pharmaceutically acceptable carrier to a subject in need thereof. The subject invention also provides a method of treating an ischemia-reperfusion injury related disorder associated with ischemic and post-ischemic events in organs and tissues comprising administering a pharmaceutically effective amount of a fusion protein of the invention and a pharmaceutically acceptable carrier to a subject in need thereof.

In one embodiment, the ischemia-reperfusion injury related disorder is selected from the group consisting of thrombotic stroke, myocardial infarction, angina pectoris, embolic vascular occlusions, peripheral vascular insufficiency, splanchnic artery occlusion, arterial occlusion by thrombi or embolisms, arterial occlusion by non-occlusive processes such as following low mesenteric flow or sepsis, mesenteric arterial occlusion, mesenteric vein occlusion, ischemia-reperfusion injury to the mesenteric microcirculation, ischemic acute renal failure, ischemia-reperfusion injury to the cerebral tissue, intestinal intussusception, hemodynamic shock, tissue dysfunction, organ failure, restenosis, atherosclerosis, thrombosis, platelet aggregation, conditions resulting from procedures such as angiography, cardiopulmonary and cerebral resuscitation, cardiac surgery, organ surgery, organ transplantation, and systemic and intragraft inflammatory responses that occur after cold ischemia-reperfusion in the setting of organ transplantation.

The subject invention further provides a method of treating a cardiovascular disease comprising administering a pharmaceutically effective amount of a peptide according to the invention or a homolog or a derivative thereof and a pharmaceutically acceptable carrier to a subject in need thereof. The subject invention further provides a method of treating a cardiovascular disease comprising administering a pharmaceutically effective amount of an antibody of the invention and a pharmaceutically acceptable carrier to a subject in need thereof. The subject invention also provides a method of treating a cardiovascular disease comprising administering a pharmaceutically effective amount of a fusion protein of the invention and a pharmaceutically acceptable carrier to a subject in need thereof.

In one embodiment, the cardiovascular disease is selected from the group consisting of a peripheral vascular disease and a coronary artery disease. In another embodiment, the coronary artery disease is selected from the group consisting of myocardial infarction, heart injury, congestive heart failure, cardiac dysfunction in sepsis, myocardial failure, myocardial hypertrophy, ischemic cardiomyopathy, stroke, thrombotic stroke, myocarditis, cardiomyopathy, myocarditis, decompensated heart failure, ischemic myocardial disease, congenital heart disease, angina pectoris, ischemia—reperfusion injury in ischemic and post-ischemic events, cerebrovascular accident, fibrosis, platelet aggregation, atherosclerosis, thrombosis, restenosis after coronary intervention, intimal hyperplasia and arteriogenesis.

The subject invention further provides a method of treating a heavy metal induced disease comprising administering a pharmaceutically effective amount of a peptide according to the invention or a homolog or a derivative thereof and a pharmaceutically acceptable carrier to a subject in need thereof. The subject invention further provides a method of treating a heavy metal induced disease comprising administering a pharmaceutically effective amount of an antibody of the invention and a pharmaceutically acceptable carrier to a subject in need thereof. The subject invention also provides a method of treating a heavy metal induced disease comprising administering a pharmaceutically effective amount of a fusion protein of the invention and a pharmaceutically acceptable carrier to a subject in need thereof.

In one embodiment, the heavy metal induced disease is selected from the group consisting of lead, zinc and cadmium poisoning.

The subject invention further provides a method of treating a kidney disease comprising administering a pharmaceutically effective amount of a peptide according to the invention or a homolog or a derivative thereof and a pharmaceutically acceptable carrier to a subject in need thereof. The subject invention further provides a method of treating a kidney disease comprising administering a pharmaceutically effective amount of an antibody of the invention and a pharmaceutically acceptable carrier to a subject in need thereof. The subject invention also provides a method of treating a kidney disease comprising administering a pharmaceutically effective amount of a fusion protein of the invention and a pharmaceutically acceptable carrier to a subject in need thereof.

In one embodiment, the kidney disease is selected from the group consisting of nephropathy, nephritis, bacterial pyelonephritis, glomerulonephritis, lupus nephritis, acute and chronic renal failure, and renal vascular disease.

The subject invention further provides a method of treating an inflammatory disease comprising administering a pharmaceutically effective amount of a peptide according to the invention or a homolog or a derivative thereof and a pharmaceutically acceptable carrier to a subject in need thereof. The subject invention further provides a method of treating an inflammatory disease comprising administering a pharmaceutically effective amount of an antibody of the invention and a pharmaceutically acceptable carrier to a subject in need thereof. The subject invention also provides a method of treating an inflammatory disease comprising administering a pharmaceutically effective amount of a fusion protein of the invention and a pharmaceutically acceptable carrier to a subject in need thereof.

In one embodiment, the inflammatory disease is selected from the group consisting of gingivitis, periodontitis, hepatitis, cirrhosis, pancreatitis, myocarditis, vasculitis, gastritis, gout, gouty arthritis, and inflammatory skin disorders, selected from the list comprising of psoriasis, atopic dermatitis, eczema, rosacea, urticaria, and acne.

The subject invention further provides a method of treating an infectious disease caused by an intracellular pathogen comprising administering a pharmaceutically effective amount of a peptide according to the invention or a homolog or a derivative thereof and a pharmaceutically acceptable carrier to a subject in need thereof. The subject invention further provides a method of treating an infectious disease comprising administering a pharmaceutically effective amount of an antibody of the invention and a pharmaceutically acceptable carrier to a subject in need thereof. The subject invention also provides a method of treating an infectious disease comprising administering a pharmaceutically effective amount of a fusion protein of the invention and a pharmaceutically acceptable to carrier to a subject in need thereof.

In one embodiment, the infectious disease is caused by an intracellular pathogen selected from the group consisting of a virus, a bacterium, a protozoa and an intracellular parasite.

The subject invention further provides a method for treating cancer comprising administering a pharmaceutically effective amount of a peptide according to the invention or a homolog or a derivative thereof and a pharmaceutically acceptable carrier to a subject in need thereof. The subject invention further provides a method of treating cancer comprising administering a pharmaceutically effective amount of an antibody of the invention and a pharmaceutically acceptable carrier to a subject in need thereof. The subject invention also provides a method of treating cancer comprising administering a pharmaceutically effective amount of a fusion protein of the invention and a pharmaceutically acceptable carrier to a subject in need thereof.

In a specific embodiment, the cancer is selected from the group consisting of solid tumors, sarcomas, hematological malignancies including but not limited to leukemia, chronic lymphocytic leukemia, acute myelogenous leukemia, chronic myelogenous leukemia, multiple myeloma, Hodgkin's lymphoma, Non-Hodgkin's lymphoma, cancer of the breast, prostate cancer, lung cancer, ovary cancer, colon cancer, spleen cancer, kidney cancer, bladder cancer, head and neck cancer, cervical cancer, testicle cancer, stomach cancer, liver cancer, bone cancer, skin cancer, melanoma, pancreatic cancer, and brain cancer.

In one embodiment, the cancer is invasive. In another embodiment, the cancer is metastatic.

The subject invention further provides a method for treating preterm birth, particularly infection-associated and/or uterine contractility comprising administering a pharmaceutically effective amount of a peptide according to the invention or a homolog or a derivative thereof and a pharmaceutically acceptable carrier to a subject in need thereof. The subject invention further provides a method of treating preterm birth, particularly infection-associated and/or uterine contractility comprising administering a pharmaceutically effective amount of an antibody of the invention and a pharmaceutically acceptable carrier to a subject in need thereof. The subject invention also provides a method of treating preterm birth, particularly infection-associated and/or uterine contractility comprising administering a pharmaceutically effective amount of a fusion protein of the invention and a pharmaceutically acceptable carrier to a subject in need thereof.

The subject invention further provides a method for treating complications of surgery and surgical interventions related to presence of endotoxin and bacterial infections comprising administering a pharmaceutically effective amount of a peptide according to the invention or a homolog or a derivative thereof and a pharmaceutically acceptable carrier to a subject in need thereof. The subject invention further provides a method of treating complications of surgery and surgical interventions related to presence of endotoxin and bacterial infections comprising administering a pharmaceutically effective amount of an antibody of the invention and a pharmaceutically acceptable carrier to a subject in need thereof. The subject invention also provides a method of treating complications of surgery and surgical interventions related to presence of endotoxin and bacterial infections comprising administering a pharmaceutically effective amount of a fusion protein of the invention and a pharmaceutically acceptable carrier to a subject in need thereof.

The subject invention further provides a method for treating acute allograft rejection after organ transplantation comprising administering a pharmaceutically effective amount of a peptide according to the invention or a homolog or a derivative thereof and a pharmaceutically acceptable carrier to a subject in need thereof. The subject invention further provides a method of treating acute allograft rejection after organ transplantation comprising administering a pharmaceutically effective amount of an antibody of the invention and a pharmaceutically acceptable carrier to a subject in need thereof. The subject invention also provides a method of treating acute allograft rejection after organ transplantation comprising administering a pharmaceutically effective amount of a fusion protein of the invention and a pharmaceutically acceptable carrier to a subject in need thereof.

As used herein the term "treating" should be understood to refer to preventing, curing, reversing, attenuating, alleviating, minimizing, suppressing or halting the deleterious effects of the above-described diseases, disorders or conditions.

Treating, according to the present invention, can be effected by specifically upregulating the expression of at least one of the peptides of the present invention in a subject.

Optionally, upregulation may be effected by administering to the subject at least one of the peptides of the present invention, as described herein.

Alternatively or additionally, an upregulating method may optionally be affected by specifically upregulating the amount (optionally expression) in the subject of at least one of the peptides of the present invention.

It will be appreciated that treatment of the above-described diseases according to the present invention may be combined with other treatment methods known in the art (i.e., combination therapy). Thus, treatment of diseases using the peptides, antibodies or fusion proteins of the present invention may be combined with, for example, radiation therapy, antibody therapy and/or chemotherapy, surgery or in combination therapy with conventional drugs, such as immunosuppressants or cytotoxic drugs.

A peptide, antibody, fusion protein or pharmaceutical composition of the invention may also be administered in conjunction with other compounds, including, but not limited to, estrogens, androgens, progestagens, tamoxifen, antiprogestagens, chemotherapeutic agents such as cytotoxic and cytostatic agents, immunological modifiers such as interferons and interleukins, growth hormones or other cytokines, folic acid, vitamins, minerals, aromatase inhibitors, RNAi, Histone Deacetylase Inhibitors proteasome inhibitors, and/or in combination with surgery and/or radiation therapy and so forth.

As used herein, a subject can be a male or a female subject; a subject can be a human subject or any other mammal.

Without being bound by theory, it is possible that a peptide of the invention interferes with internal segment-segment interactions of gp96 thereby preventing it from reaching its active state.

Without being bound by theory, the mechanism of action of the peptides of the invention may be by their binding to their parent gp96 protein to the segment corresponding to the partner helix of each bioactive peptide of the invention.

The subject invention further provides a (poly) nucleotide sequence encoding a peptide of the invention or a homolog thereof.

As used herein, "a (poly)nucleotide sequence encoding a peptide of the invention or a homolog thereof" should be understood to encompass any nucleotide sequence encoding a peptide of the invention or a homolog thereof. As known to a person skilled in the art, due to the known degeneracy of the genetic code (codon variability), amino acids can be coded for by more than one codon. Indeed, some amino acids have as many as six alternative codons (e.g. leucine) while some others have a single, required codon (e.g. methionine).

In one embodiment, a polynucleotide sequence of the invention is that encoding SEQ ID NO:1. In one embodiment, the nucleotide sequence is that depicted in SEQ ID NO:7.

In another embodiment, a polynucleotide sequence of the invention is that encoding SEQ ID NO:2. In one embodiment, the nucleotide sequence is that depicted in SEQ ID NO:8.

In one embodiment, a polynucleotide sequence of the invention is that encoding SEQ ID NO:3. In one embodiment, the nucleotide sequence is that depicted in SEQ ID NO:9.

In another embodiment, a polynucleotide sequence of the invention is that encoding SEQ ID NO:4. In one embodiment, the nucleotide sequence is that depicted in SEQ ID NO:10.

In one embodiment, a polynucleotide sequence of the invention is that encoding SEQ ID NO:5. In one embodiment, the nucleotide sequence is that depicted in SEQ ID NO:11.

In another embodiment, a polynucleotide sequence of the invention is that encoding SEQ ID NO:6. In one embodiment, the nucleotide sequence is that depicted in SEQ ID NO:12.

In another embodiment, a polynucleotide sequence of the invention is that encoding SEQ ID NO:27. In one embodiment, the nucleotide sequence is that depicted in SEQ ID NO:28.

In another embodiment, a polynucleotide sequence of the invention is that encoding SEQ ID NO:29. In one embodiment, the nucleotide sequence is that depicted in SEQ ID NO:30.

In another embodiment, a polynucleotide sequence of the invention is that encoding SEQ ID NO:31. In one embodiment, the nucleotide sequence is that depicted in SEQ ID NO:33.

In another embodiment, a polynucleotide sequence of the invention is that encoding SEQ ID NO:32. In one embodiment, the nucleotide sequence is that depicted in SEQ ID NO:34.

The term "antibody" as used herein should be understood to encompass a polypeptide ligand substantially encoded by an immunoglobulin gene or immunoglobulin genes, or fragments thereof, which specifically bind and recognize an epitope (e.g., an antigen).

The antibody can be provided as, e.g., an intact immunoglobulin or as a fragment, e.g., a fragment produced by digestion with various peptidases. This includes, e.g. Fab' and F(ab)'$_2$ Fv fragments (defined as a genetically engineered fragment containing the variable region of the light chain and the variable region of the heavy chain expressed as two chains) and single chain antibodies ("SCAs"), genetically engineered molecules containing the variable region of the light chain and the variable region of the heavy chain, linked by a suitable polypeptide linker as a genetically fused single chain molecule.

The term "antibody," as used herein, also includes antibody fragments produced e.g. by modification of whole antibodies or synthesized de novo using recombinant DNA methodologies.

The term "antibody" includes, but is not limited to, polyclonal antibodies, monoclonal antibodies, chimeric antibodies, humanized antibodies, or single chain antibodies. In one embodiment, an antibody of the invention is a monoclonal antibody.

"Fc" portion of an antibody refers to that portion of an immunoglobulin heavy chain that comprises one or more heavy chain constant region domains, CH1, CH2 and CH3, but does not include the heavy chain variable region.

An antibody of the invention may be conjugated or coupled to e.g. a detectable label, a radioactive label, an enzyme, a fluorescent label, a luminescent label, a bioluminescent label, a therapeutic agent and so forth.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments may be prepared by proteolytic hydrolysis of the antibody or by expression in e.g. *E. coli* or mammalian cells (e.g. Chinese hamster ovary cell culture or other protein expression systems) of DNA encoding the fragment. Antibody fragments can be obtained by pepsin or papain digestion of whole antibodies by conventional methods.

The antibody may e.g. correspond to a single complementary-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, *Larrick and Fry Methods,* 2: 106-10 (1991).

Humanized forms of non-human (e.g., murine) antibodies may be chimeric molecules of immunoglobulins, or immunoglobulin chains or fragments thereof (such as Fv, Fab, Fab', F(ab') or other antigen-binding subsequences of antibodies) which contain a short sequence, typically of about 20-50 amino acids, derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues which are found neither in the recipient antibody nor in the imported CDR or framework (FR) sequences. In general, the humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be performed by, for example, substituting rodent CDRs or other CDR sequences for the corresponding sequences of a human antibody. Accordingly, such humanized antibodies are chimeric antibodies (see e.g. U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in e.g. rodent antibodies.

Human antibodies can also be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al. and Boerner et al. are also available for the preparation of human monoclonal antibodies (Cole et al., *Monoclonal Antibodies and Cancer Therapy,* Alan R. Liss, p. 77 (1985) and Boerner et al., *J. Immunol.,* 147(1):86-95 (1991)]. Similarly, human antibodies can be prepared by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in Marks et al., *Bio/Technology* 10: 779-783 (1992); Lonberg et al., *Nature* 368: 856-859 (1994); Morrison, *Nature* 368 812-13 (1994); Fishwild et al., *Nature Biotechnology* 14, 845-51 (1996); Neuberger, *Nature Biotechnology* 14: 826 (1996); and Lonberg and Huszar, *Intern. Rev. Immunol.* 13, 65-93 (1995).

An antibody of the invention binds specifically (or selectively) to a peptide of the invention. The term "specifically (or selectively) binds" to an antibody or the term "specifically (or selectively) immunoreactive with," when referring to a protein or peptide, refers to a binding reaction that is determinative of the presence of the peptide in a heterogeneous population of peptide and other biologics. Thus, under designated immunoassay conditions, the specified antibodies bind to a particular peptide at least twice the background and do not substantially bind in a significant amount to other proteins or peptides present in the sample. Specific binding to an antibody under such conditions may require an antibody that is selected for its specificity to a particular peptide. A variety of immunoassay formats may be used to select antibodies specifically immunoreactive with a particular peptide. For example, solid-phase ELISA immunoassays are routinely used to select antibodies specifically immunoreactive with a protein or a peptide (see, e.g., Harlow & Lane, Antibodies, A Laboratory Manual (1988)).

Typically a specific or selective reaction will be at least twice the background signal or noise and more typically more than 10 to 100 times background.

The terms "conjugate" and "fusion protein" and any lingual derivatives thereof are interchangeably used herein.

The subject invention further provides a peptide of the present invention conjugated or fused to another peptide or to a polypeptide. Such conjugates/fusion proteins may be prepared by any methodology known in the art such as, but not limited to the preparation of conjugates/fusion proteins using chemical synthesis or using recombinant technology.

Examples of peptides or polypeptides which may be conjugated/fused to a peptide of the invention are multiple antigenic peptides (MAP), Fc chains of immunoglobulins and signal sequences.

In one embodiment, a peptide or a polypeptide which may be conjugated to a peptide of the invention is an immunoglobulin sequence (e.g., an IgG sequence). Non-limiting examples of immunoreactive ligands (which may e.g. serve as a targeting moiety) are an antigen-recognizing immunoglobulin (also referred to herein as "antibody") and an antigen-recognizing fragment thereof, e.g., immunoglobulins that can recognize a tumor-associated antigen.

As used herein, "immunoglobulin" should be understood to refer to any recognized class or subclass of immunoglobulins such as IgG, IgA, IgM, IgD, or IgE. In one embodiment, the immunoglobulin is within the IgG class of immunoglobulins. The immunoglobulin may be derived from any species, such as, but not limited to human, murine, or rabbit origin. In addition, the immunoglobulin may be polyclonal or monoclonal. In one embodiment, the immunoglobulin is monoclonal.

A conjugate/fusion protein may be prepared from a peptide according to the present invention by fusion with e.g. a portion of an immunoglobulin comprising a constant region of an immunoglobulin. In one embodiment, the portion of the immunoglobulin comprises a heavy chain constant region. In another embodiment, the heavy chain constant region comprises a human heavy chain constant region. In yet another embodiment, the heavy chain constant region is an IgG heavy chain constant region. In yet another embodiment, the heavy chain constant region is an Fc chain. In yet another embodiment, the Fc chain is an IgG Fc fragment that comprises CH2 and CH3 domains. In yet another embodiment, the IgG Fc fragment is of the IgG1 subtype. The Fc chain may be a known or "wild type" Fc chain, or may be mutated. Non-limiting, illustrative, exemplary types of mutations are described in US Patent Application No. 20060034852, hereby incorporated by reference as if fully set forth herein.

The term "Fc chain" as used herein should be understood to encompass any type of Fc fragment. Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific modifications may result e.g. in glycosylation and/or other desired modifications to the Fc chain. It is envisaged that modifications may be made to e.g. block a function of Fc which is considered to be undesirable, such as an undesirable immune system effect Thus, conjugates of the invention (which comprise a peptide of the invention) may comprise an antigen-recognizing immunoglobulin fragment and/or Fc chain. Such immunoglobulin fragments may comprise, for example, the Fab', F(ab') 2, Fv or Fab fragments, or other antigen-recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See Parham, *J. Immunology*, 131, 2895, 1983; Lamoyi et al., *J. Immunological Methods*, 56, 235, 1983.

The following abbreviations should be understood as follows:

Amino Acid Abbreviation IUPAC Symbol:

A=Ala=Alanine
C=Cys=Cysteine
D=Asp=Aspartic Acid
E=Glu=Glutamic Acid
F=Phe=PhenylAlanine
G=Gly=Glycine
H=His=Histidine
I=Ile=Isoleucine
L=Lys=Lysine
M=Met=Methionine
N=Asn=Asparagine
P=Pro=Proline
Q=Gln=Glutamine
R=Arg=Arginine
S=Ser=Serine
T=Thr=Threonine
V=Val=Valine
W=Trp=Tryptophan
Y=Tyr=Tyrosine The following abbreviations shall be employed for nucleotide bases: A for adenine; G for guanine; T for thymine; U for uracil; and C for cytosine.

The invention is further described in the following examples, which are not in any way intended to limit the scope of the inventions as claimed.

EXAMPLES

Example 1

Synthesis of Peptides of the Invention

The peptides were synthesized by solid-phase peptide synthesis using Fmoc-chemistry at Pepscan Systems (http://www.pepscan.nl). The peptides were amidated at their C-terminus, and acetylated at their N-terminus. CGEN-GP1 [SEQ ID NO: 1] has a molecular weight of 4505.6, CGEN-GP2 [SEQ ID NO: 2] has a molecular weight of 4136.1; CGEN-GP3 [SEQ ID NO: 3] has a molecular weight of 3789.1; CGEN-GP4 [SEQ ID NO: 27] has a molecular weight of 3765.6 and CGEN-GP5 [SEQ ID NO: 29] has a molecular weight of 4363.2. The CGEN-GP1 [SEQ ID NO: 25] partner helix has a molecular weight of 4272.

Example 2

Analysis of Activity of Peptides of the Invention on LPS-Induced Cytokine Release from Human Peripheral Blood Mononuclear Cells (PBMCs)

CGEN-GP1, CGEN-GP2 and CGEN-GP3, as synthesized in Example 1, were analyzed for their ability to inhibit LPS-induced cytokine secretion from human PBMCs. Peptides were assayed at two concentrations (3 and 30 ug/mL) in duplicates. Cryopreserved PBMCs were drip-thaw and seeded at $2\times10^5$ cells/well in 140 µl of media per well. Cells were incubated for 1 hour at 37° C. at 5% CO2 and a peptide of the invention or Dexamethasone (Dex) as a positive control, were added in 20 µl of medium. Cells were incubated for 30 minutes and LPS (50 pg/ml) was added at the appropriate concentration in 40 µl of medium. Plates were incubated for 24 hours, spinned at 1200 rpm for 10 minutes and supernatants were collected and stored at −80° C. The concentration of the cytokines was measured using a Luminex analyzer (IS100, Luminex Corporation) and bead-based reagents (Upstate Biotechnology).

FIG. 1 demonstrates the effect of CGEN-GP1, CGEN-GP2 and CGEN-GP3 on the secretion of the cytokines IL-1b, IL-6, IL-8, MIP-1α and TNFα from PBMCs treated with LPS. Following LPS treatment, CGEN-GP1 decreased the secretion of all cytokines tested by 80% to 90%. CGEN-GP2 and CGEN-GP3 had moderate effects on IL-1β, IL-6, MIP-1α and TNF-α secretion (~10-30%). CGEN-GP2 had no effect on IL-8 release.

Example 3

Analysis of Activity of Peptides of the Invention on Anti-CD3-Induced Cytokine Release from Human PBMCs CGEN-GP1, CGEN-GP2 and CGEN-GP3 as synthesized in Example 1, were analyzed for their ability to inhibit anti-CD3-induced cytokine secretion from PBMCs. Peptides were assayed at two concentrations (3 and 30 ug/mL) in duplicates. Cryopreserved PBMCs were drip-thaw and seeded at $1\times10^4$ cells/well in 140 µl of media per well. Cells were incubated for 1 hour at 37° C. at 5% CO2 and a peptide of the invention or Dexamethasone as a control, were added in 20 µl of medium. Cells were incubated for 30 minutes and anti-CD3 antibody (1 µg/ml) was added at the appropriate concentration in 40 µl of medium. Plates were incubated for 48 hours, spinned at 1200 rpm for 10 minutes and supernatants were collected and stored at −80° C. Cytokines' concentration was measured using a Luminex analyzer (IS100, Luminex Corporation) and bead-based reagents (Upstate Biotechnology).

Figure 2:
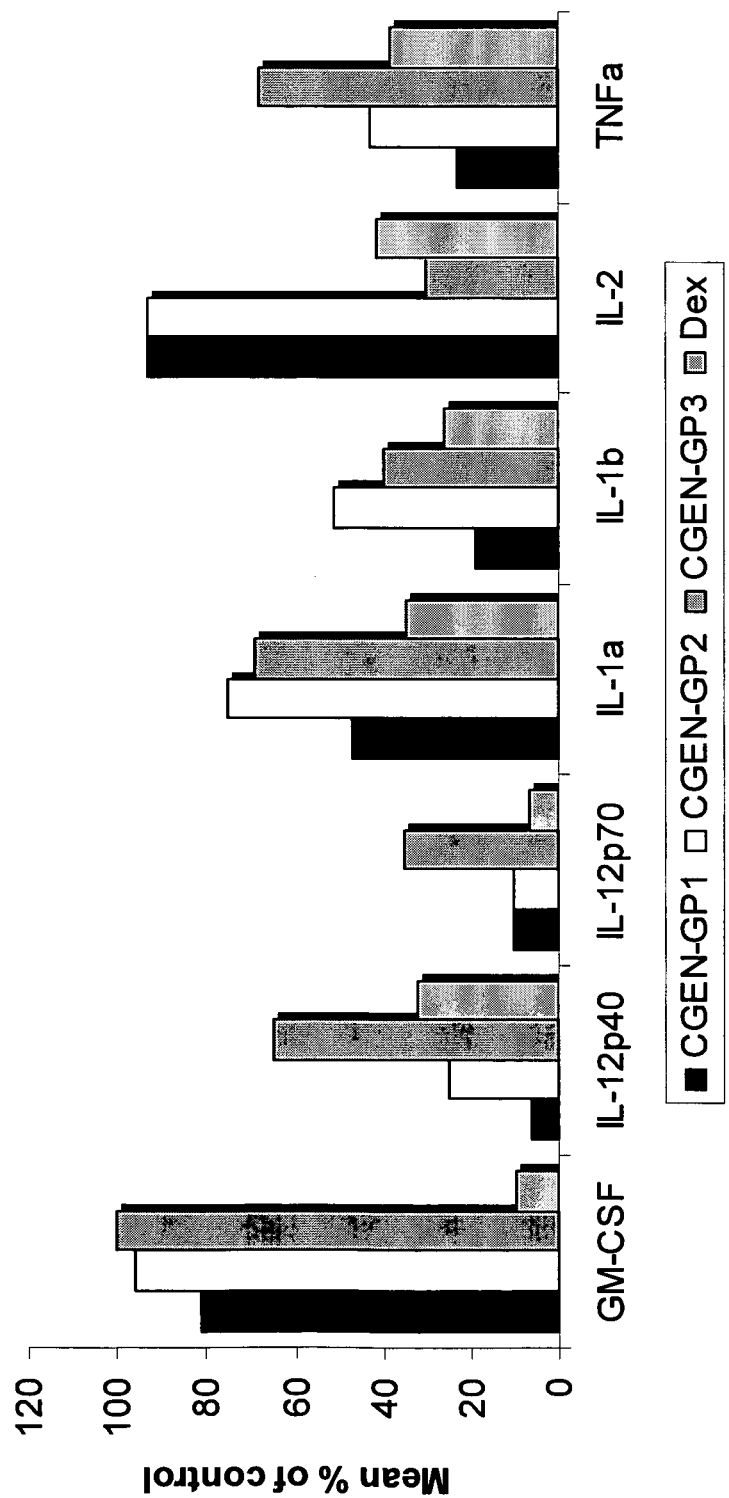
FIG. 2: presents the effect of CGEN-GP1 (SEQ ID NO:1), CGEN-GP2 (SEQ ID NO:2) and CGEN-GP3 (SEQ ID NO:3) (30 µg/ml=6 µM) on the release of LPS-induced cytokines GM-CSF, IL-12p40, IL-12p70, IL-1a, IL-1b, IL2 and TNFα from peripheral blood mononuclear cells (PBMCs). The concentration of the cytokines was measured using Luminex and Upstate Bead kit assay.

FIG. 2 demonstrates the effect of CGEN-GP1, CGEN-GP2 and CGEN-GP3 on the secretion of the cytokines GM-CSF, IL-12p40, IL-12p70, IL-1a, IL-1b, IL-2 and TNFα from PBMCs treated with anti-CD3 antibody. Following anti CD3 treatment, CGEN-GP1 decreased IL-12p40 by more than 90%, IL-12p70 by 90%, IL-1β and TNFα by approximately 80% and IL-1α by 50%. CGEN-GP1 had only 20% inhibition on GM-CSF release and no effect on IL-2 release. CGEN-GP2 decreased IL-12p40 by 75%, IL-12p70 by 90%, IL-1β and TNFα by approximately 50% and IL-1α by 25%. CGEN-GP2 had no effect on GM-CSF and IL-2 release. CGEN-GP3 decreased IL-12p40 by 40%, IL-12p70 and IL-2 by 70%, IL-1β by 60%, TNFα by approximately 30% and IL-1α by 30%. CGEN-GP3 had no effect on GM-CSF release.

Example 4

Analysis of Activity of Peptides of the Invention on the Release of Cytokines from Human Peripheral Blood Mononuclear Cells (PBMCs) Treated with LPS or *Staphylococcus epidermidis*

CGEN-GP1 (SEQ ID NO:1) as synthesized in Example 1, was analyzed for its ability to inhibit LPS-induced cytokine secretion from human PBMCs. Peptides were assayed at three concentrations (30, 60 and 120 ug/mL) in duplicates. Fresh hPBMCs were seeded at $2\times10^5$ cells/well in 140 µl of media per well. Cells were incubated for 1 hour at 37° C. at 5% CO2 and the CGEN-GP1 peptide was added. Cells were incubated for 30 minutes and LPS or *Staphylococcus epidermidis* were added at the appropriate concentration. Plates were incubated for 24 hours, spinned at 1200 rpm for 10 minutes and supernatants were collected and stored at −80° C. The concentrations of the cytokines tested were measured using ELISA kits (R&D Systems, Quantikine ELISA kits, Human IL-beta, Cat number DLB50, Human TNF-alpha, Cat # STA00C).

Figure 3:
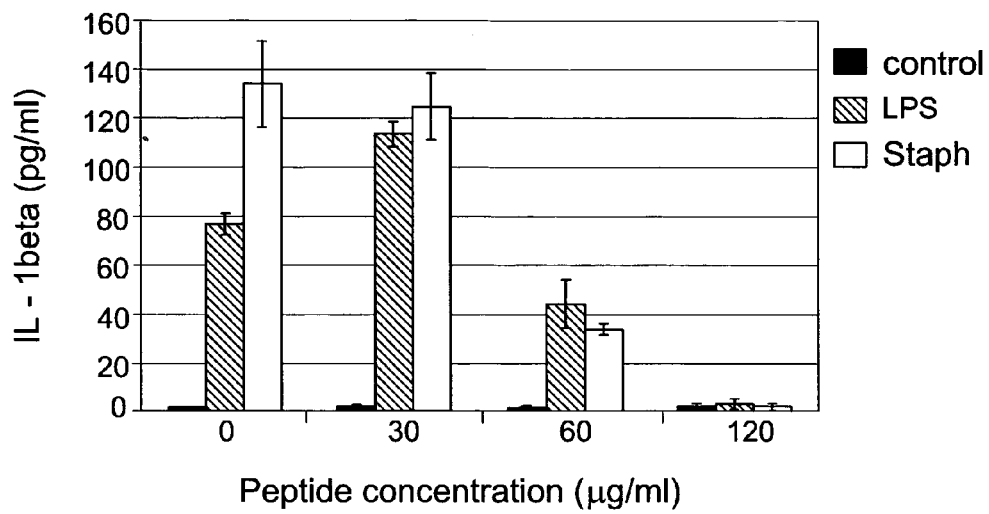
FIG. 3: presents the effect of CGEN-GP1 (SEQ ID NO:1), (30, 60 or 120 µg/ml) on the release of the cytokine IL-1 beta from untreated human peripheral blood mononuclear cells (PBMCs) (control), from PBMCs treated with LPS, and from PBMCs treated with *Staphylococcus epidermidis*. The concentration of IL-1 beta was measured using ELISA kits specific to human IL-1beta (R&D Systems, Quantikine ELISA kit, Cat number DLB50).

FIG. 3 demonstrates the effect of CGEN-GP1 (SEQ ID NO:1), (30, 60 or 120 µg/ml) on the secretion of the cytokine IL-1 beta from untreated human PBMCs or PBMCs treated with LPS or *Staphylococcus epidermidis*. Following both treatments, 120 µg/ml of CGEN-GP1 abolished the secretion of IL-1beta.

Figure 4:
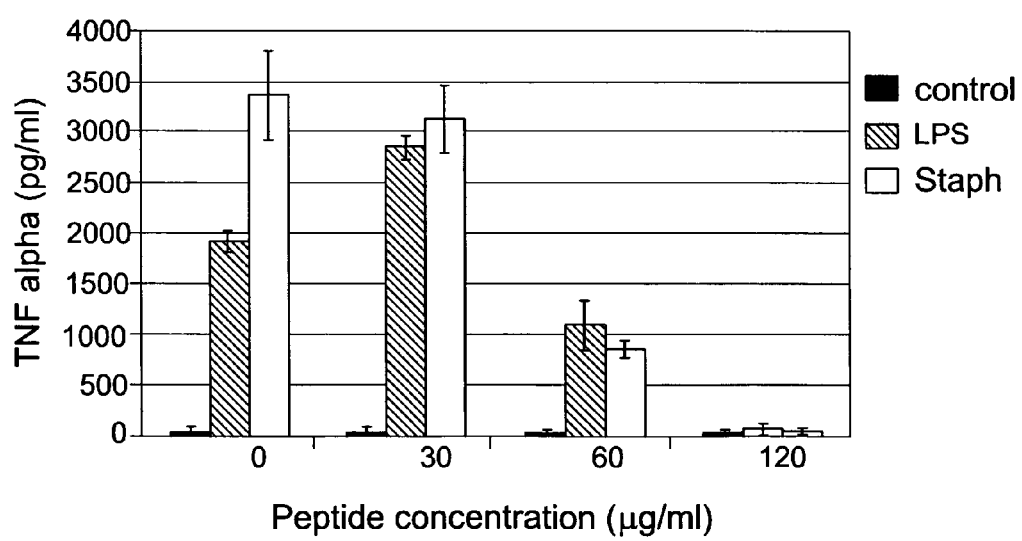
FIG. 4: presents the effect of CGEN-GP1 (SEQ ID NO:1), (30, 60 or 120 µg/ml) on the release of the cytokine TNF-alpha from untreated human peripheral blood mononuclear cells (PBMCs) (control), from PBMCs treated with LPS, and from PBMCs treated with *Staphylococcus epidermidis*. The concentration of TNF-alpha was measured using ELISA kits specific to human TNF-alpha (R&D Systems, Human TNF-alpha Quantikine ELISA Kit, Cat # STA00C).

FIG. 4 demonstrates the effect of CGEN-GP1 (SEQ ID NO:1), (30, 60 or 120 µg/ml) on the secretion of the cytokine TNF-alpha from untreated human PBMCs, or PBMCs treated with LPS or *Staphylococcus epidermidis*. Following both treatments, CGEN-GP1 decreased the secretion of TNF-alpha in a dose-dependent manner, while 120 µg/ml of CGEN-GP1 abolished the secretion of TNF-alpha.

Example 5

Analysis of Activity of Peptides of the Invention on the Release of Cytokines from Human Peripheral Blood Mononuclear Cells (PBMCs) Treated with IL-12 plus IL-18

CGEN-GP1 (SEQ ID NO:1), was analyzed for its ability to inhibit IL-12 and IL-18-induced secretion of IFN-gamma from human PBMCs. The peptide was assayed at two concentrations (30 and 60 µg/mL) in duplicates. Fresh hPBMCs were seeded at $2\times10^5$ cells/well in 140 µl of media per well. Cells were incubated for 1 hour at 37° C. at 5% CO2 and the CGEN-GP1 peptide was added. Cells were incubated for 30 minutes and IL-12 plus IL-18 were added at the appropriate concentrations. Plates were incubated for 48 hours, spinned at 1200 rpm for 10 minutes and supernatants were collected. The concentration of IFN-gamma was measured using ELISA kit (R&D Systems, Human IFN-gamma Quantikine ELISA kit, Cat number DIF50).

Figure 5:
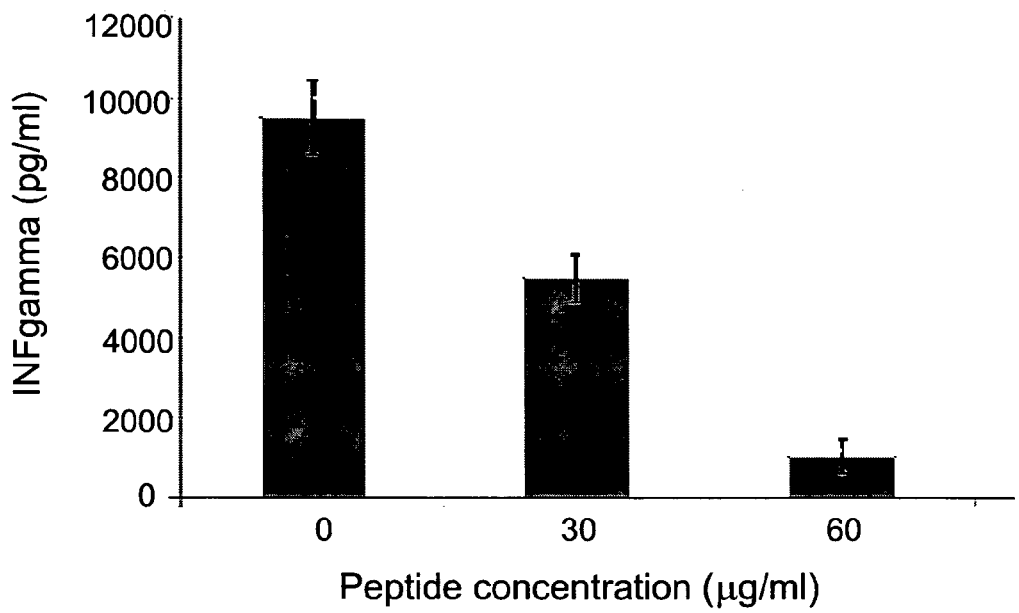
FIG. 5: presents the effect of CGEN-GP1 (SEQ ID NO:1), (30 or 60 µg/ml) on the release of the cytokine IFN-gamma from PBMCs treated with the cytokines IL-12 plus IL-18. The concentration of IFN-gamma was measured using ELISA kits specific to human IFN-gamma (R&D Systems, Human IFN-gamma Quantikine ELISA kit, Cat number DIF50)

FIG. 5 demonstrates the effect of CGEN-GP1 (SEQ ID NO:1), (30 or 60 µg/ml) on the secretion of the cytokine IFN-gamma from PBMCs treated with IL-12 plus IL-18.

Following that treatment, CGEN-GP1 decreased the secretion of IFN-gamma in a dose-dependent manner, while 60 µg/ml of CGEN-GP1 decreased the secretion of TNF-alpha by 90%.

Example 6

Analysis of Activity of a Peptide of the Invention in Inhibiting TNF-α Secretion from a Human Monocyte-Derived Cell Line CGEN-GP1, as synthesized in Example 1, was analyzed for its ability to inhibit LPS-induced TNF-α secretion from THP-1 cells (Human acute monocytic leukemia, monocytes, TIB-202, ATCC). THP-1 cells were seeded at $2\times10^5$ cells/ml in 100 µl of media (RPMI-1640 medium+10% FBS) in a 96 well plates. The reconstituted peptide at final concentrations of 20, 60, 180, 540, 1620, 4860 or 14580 nM were added to the relevant wells in a volume of 100 µl and LPS at a final concentration of 100 ng/ml (Sigma, Cat # L-6529, Lot #054K4022, stock concentration of 1 mg/ml) was added to the wells in a volume of 100 µl. Plates were incubated for 4 hours and then centrifuged 5 minutes at 4000 rpm. Conditioned medium (200 µl) was transferred to new plates and kept at −20° C. The concentration of TNF-α was measured using TNF-α ELISA (R&D Systems, Human TNF-alpha Quantikine ELISA Kit, Cat # STA00C).

Figure 6:
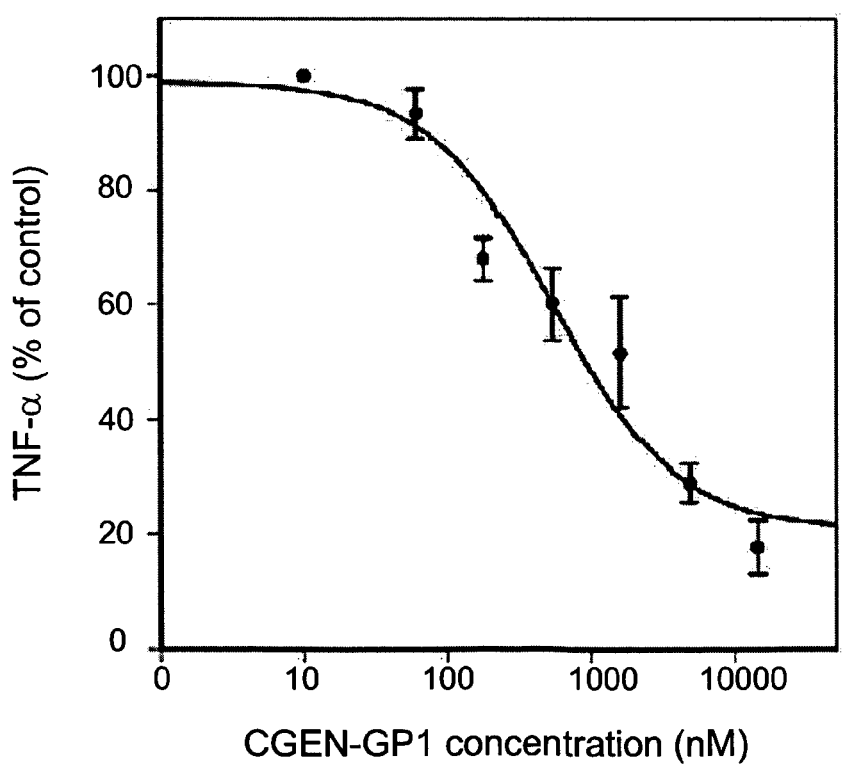
FIG. 6: presents the effect of CGEN-GP1 (SEQ ID NO:1) (20, 60, 180, 540, 1620, 4860 or 14580 nM) on LPS-induced TNFα release from THP-1 cells (Monocytes, Acute monocytic leukemia, TIB-202, ATCC). The concentration of TNFα was measured using TNF-α ELISA (R&D Systems, Human TNF-alpha Quantikine ELISA Kit, Cat # STA00C).

FIG. 6 demonstrates that 14580 nM of CGEN-GP1 inhibits more than 80% of LPS-induced TNF-α secretion from THP-1 cells.

Example 7

Analysis of Activity of Peptides of the Invention in Inhibiting TNF-α Secretion from a Human Monocyte-Derived Cell Line CGEN-GP4 (SEQ ID NO:27) and CGEN-GP5 (SEQ ID NO:29) were analyzed for their ability to inhibit LPS-induced TNF-α secretion from THP-1 cells (Human acute monocytic leukemia, monocytes, TIB-202, ATCC). THP-1 cells were seeded at $2\times10^5$ cells/ml in 100 µl of media (RPMI-1640 medium+10% FBS) in 96 well plates. The reconstituted peptide at final concentrations of 0.3, 1, 10, 30 or 60 µg/ml were added to the relevant wells in a volume of 100 µl and LPS at a final concentration of 100 ng/ml (Sigma, Cat # L-6529, Lot #054K4022, stock concentration of 1 mg/ml) was added to the wells in a volume of 100 Plates were incubated for 4 hours and then centrifuged 5 minutes at 4000 rpm. Conditioned medium (200 µl) was transferred to new plates and kept at −20° C. The concentration of TNF-α was measured using TNF-α ELISA (R&D Systems, Human TNF-alpha Quantikine ELISA Kit, Cat # STA00C). The results are shown in FIG. 7.

Figure 7:
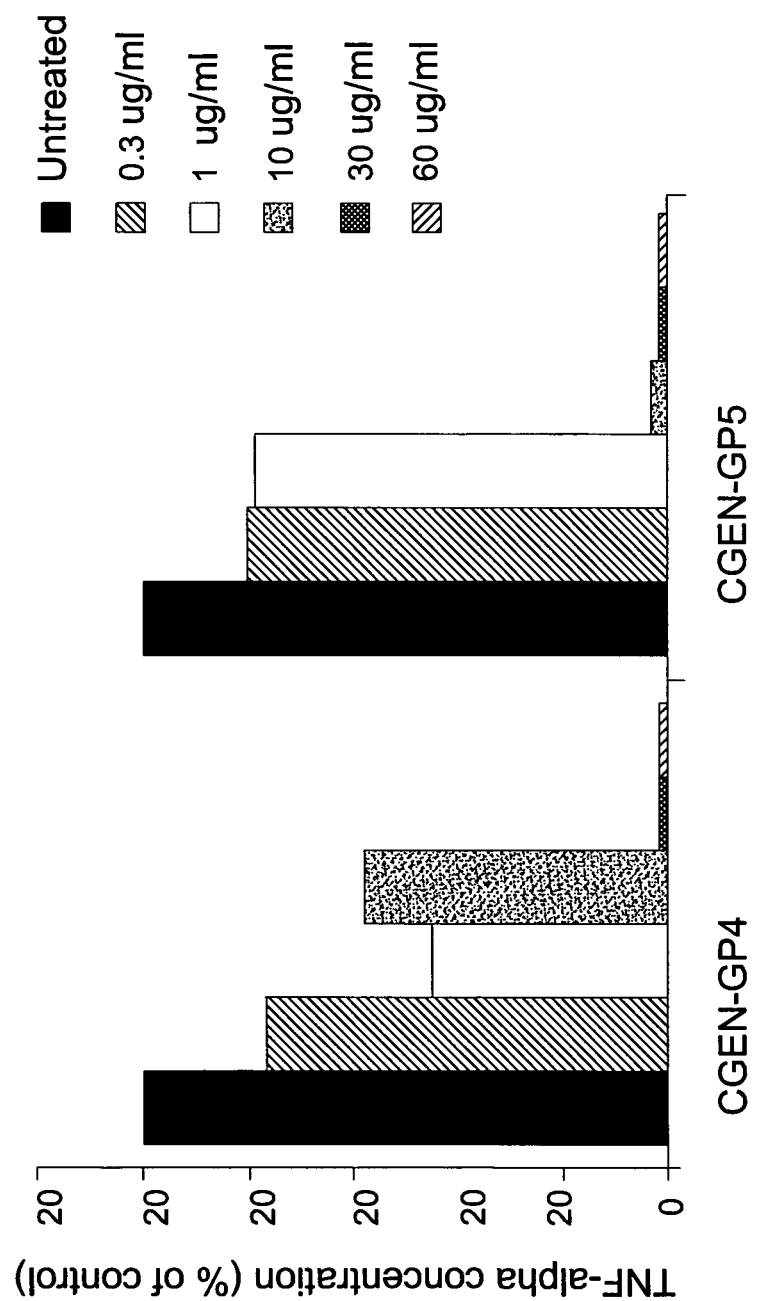
FIG. 7: presents the effect of CGEN-GP4 (SEQ ID NO: 27) and CGEN-GP5 (SEQ ID NO:29) (0.3, 1, 10, 30 or 60 µg/ml) on LPS-induced TNFα release from THP-1 cells (Monocytes, Acute monocytic leukemia, TIB-202, ATCC). The concentration of TNFα was measured using TNF-α ELISA (R&D Systems, Human TNF-alpha Quantikine ELISA Kit, Cat # STA00C).

FIG. 7 demonstrates that 30 µg/ml of CGEN-GP4 inhibits 100% of LPS-induced TNF-α secretion, while 10 µg/ml of CGEN-GP5 inhibits 100% of LPS-induced TNF-α secretion from THP-1 cells.

Example 8

Analysis of Activity of Peptides of the Invention in Inhibiting the Proliferation of Human Lung Carcinoma Cells CGEN-GP1 (SEQ ID NO:1), CGEN-GP4 (SEQ ID NO:27) and CGEN-GP5 (SEQ ID NO:29) were analyzed for their ability to inhibit the proliferation of A549 cells (Human lung carcinoma, CCL-185, ATCC). A549 cells were seeded at 6000 cells/well in 200 µA of media (DMEM medium+5% FBS) in a 96 well plate and incubated over-night (O.N). Cells were starved in 100 µl of serum free medium (SFM) containing 0.1% FBS, O.N. All lyophilized peptides were dissolved in H2O (prewarmed to 50° C.) and hand-stirred, giving a final concentration of 1 mg/ml. Reconstituted peptides were added in concentrations of 0.3, 1, 3, 10, 30 or 90 µg/ml and the cells were incubated for 48 hours.

Cell proliferation was measured using MTT assay as follows: 20 µl of MTT solution ((3-[4,5-Dimethyl-2-thiazolyl]-2,5-diphenyl-2H-tetrazolium bromide, Sigma Cat#M5655, lot#085k5322, 1 gr was dissolved in 200 ml $H_2O$ and filtered, giving a final concentration of 5 mg/ml) were added to each well for 4 hrs, after which the medium was vacuumed and 100 µl of DMSO were added to each well. Absorbance was measured in an ELISA reader at 492 nm. The results are shown in FIG. 8, and depicted in percent relative to untreated cells (which was defined as 100).

Figure 8:
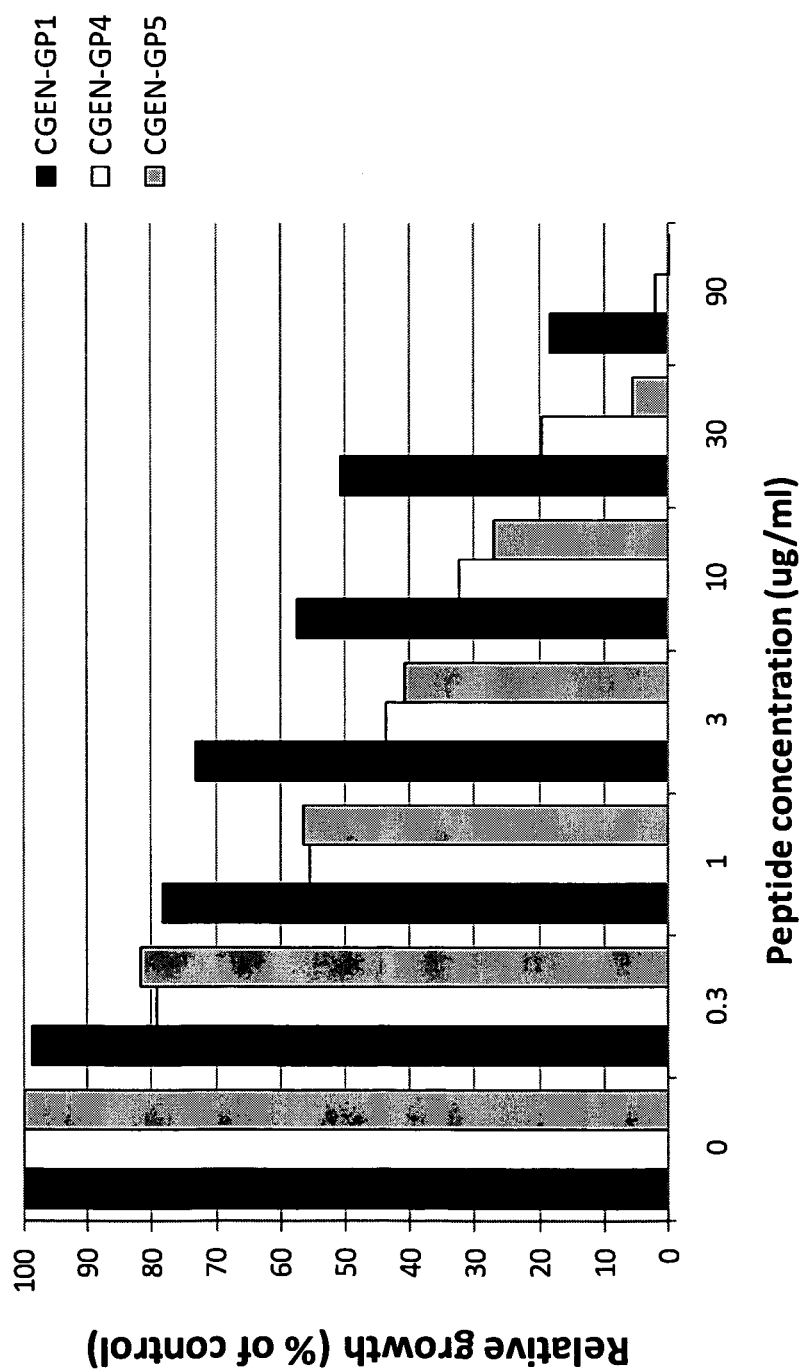
FIG. 8: presents the effect of CGEN-GP1 (SEQ ID NO:1), CGEN-GP4 (SEQ ID NO: 27) and CGEN-GP5 (SEQ ID NO: 29) (0.3, 1, 3, 10, 30 or 90 µg/ml) on the proliferation of A549 cells (Human lung carcinoma, CCL-185, ATCC). Cell proliferation was measured using MTT assay.
Figure 9A:
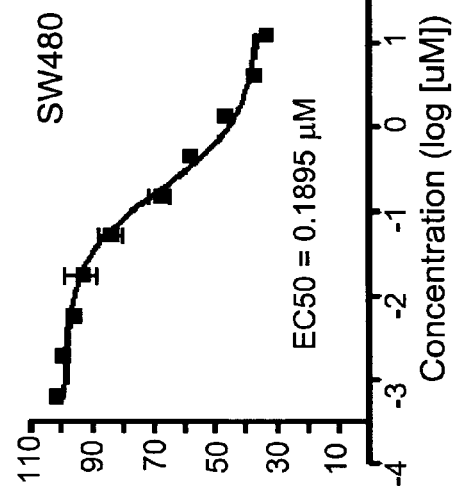
FIG. 9: presents the effect of CGEN-GP1 (SEQ ID NO:1) (0.003, 0.009, 0.028, 0.084, 0.25, 0.76, 2.28, 6.66, 20 and 60 µg/ml) on the proliferation of the cell lines HCT116 (Human colorectal carcinoma, CCL-247, ATCC) (FIG. 9A), SW480 (Human colorectal adenocarcinoma, CCL-228, ATCC) (FIG. 9B), HT29 (Human colorectal adenocarcinoma, HTB-38, ATCC) (FIG. 9C) and MCF7 (Human, mammary gland adenocarcinoma, HTB-22, ATCC) (FIG. 9D). Cell proliferation was measured using MTT assay.
Figure 9B:
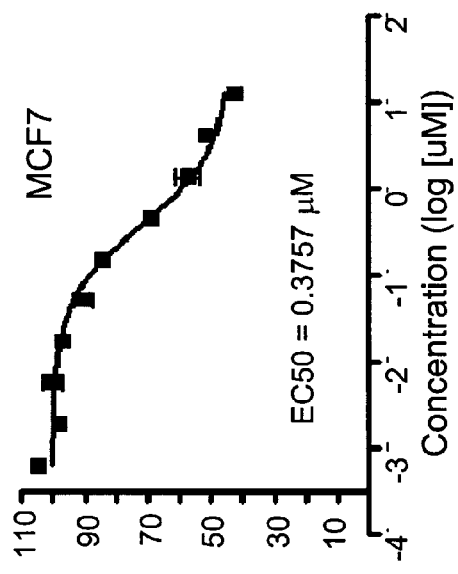
Figure 9C:
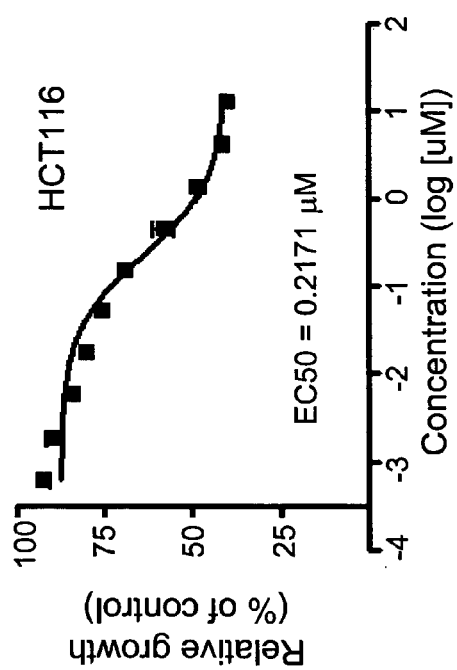
Figure 9D:
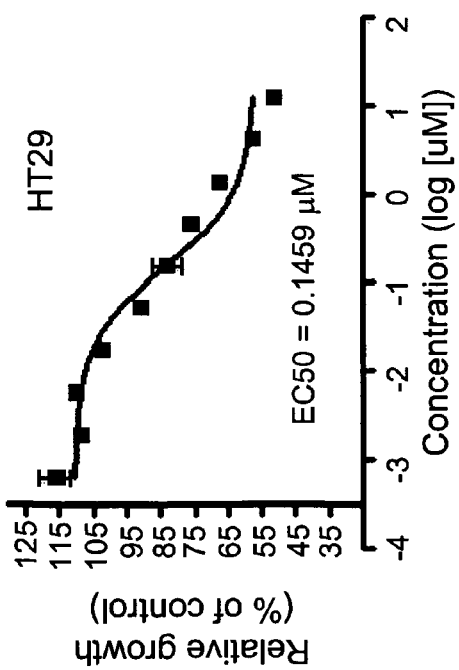
Figure 10B:
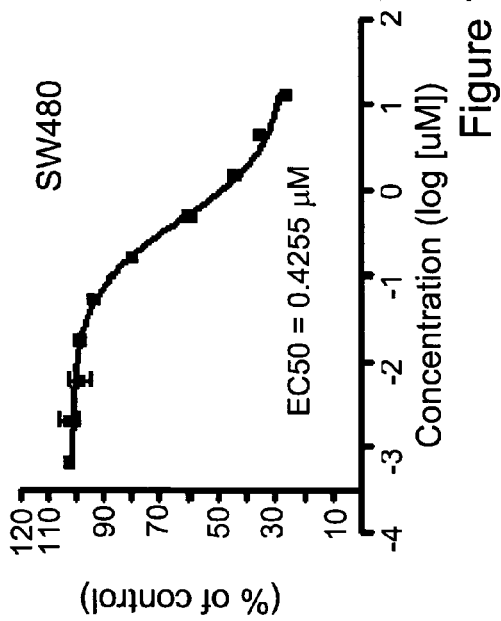
FIG. 10: presents the effect of CGEN-GP5 (SEQ ID NO:29) (0.003, 0.009, 0.028, 0.084, 0.25, 0.76, 2.28, 6.66, 20 and 60 µg/ml) on the proliferation of the cell lines HCT116 (Human colorectal carcinoma, CCL-247, ATCC) HT29 (Human colorectal adenocarcinoma, HTB-38, ATCC) (FIG. 10A); SW480 (Human colorectal adenocarcinoma, CCL- 228, ATCC) (FIG. 10B), HT29 (Human colorectal adenocarcinoma, HTB-38, ATCC) (FIG. 10C) and MCF7 (Human, mammary gland adenocarcinoma, HTB-22, ATCC) (FIG. 10D). Cell proliferation was measured using MTT assay.
Figure 10D:
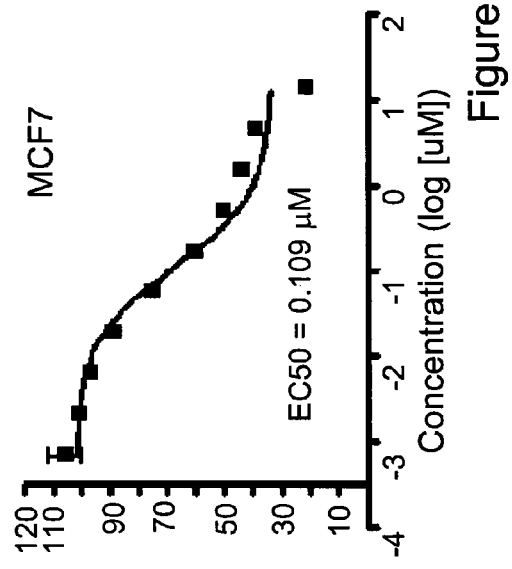
Figure 10A:
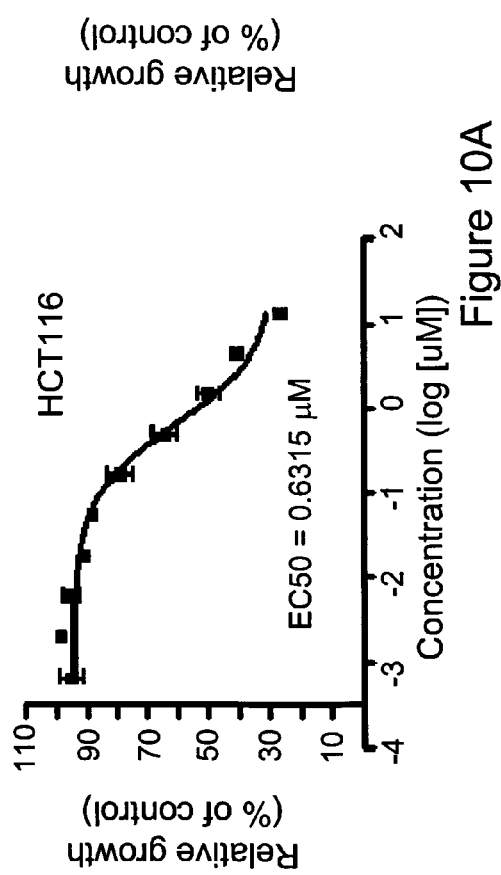
Figure 10C:
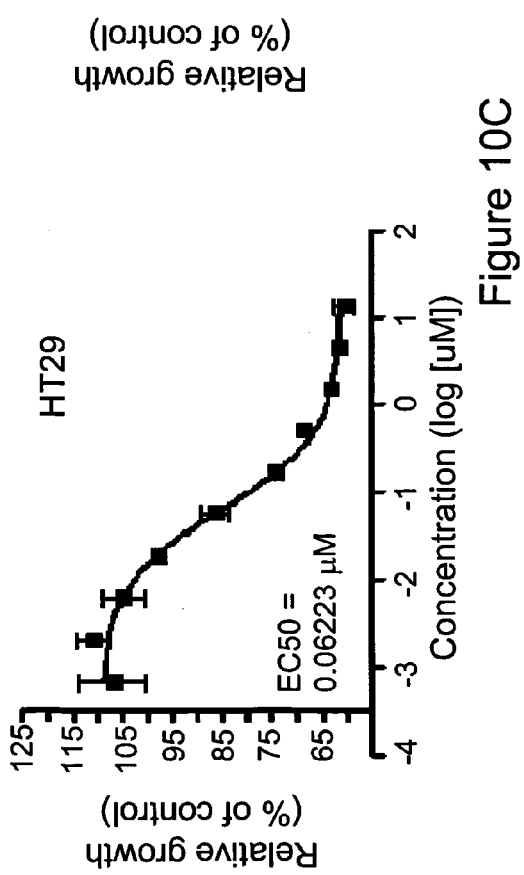

FIG. 8 demonstrates that the three different peptides inhibit the proliferation of A549 cells in a dose-dependent manner. CGEN-GP1, CGEN-GP4 and CGEN-GP5, at a concentration of 90 µg/ml, inhibit 80%, 98% and 100% of cell growth, respectively.

Example 9

Analysis of Activity of Peptides of the Invention in Inhibiting the Proliferation of Human Colorectal or Mammary Gland Carcinoma Cells CGEN-GP1 (SEQ ID NO:1) and CGEN-GP5 (SEQ ID NO:29) were analyzed for their ability to inhibit the proliferation of the cell lines HCT116 (Human colorectal carcinoma, CCL-247, ATCC), SW480 (Human colorectal adenocarcinoma, CCL-228, ATCC), MCF7 (Human, mammary gland adenocarcinoma, HTB-22, ATCC) and HT29 (Human colorectal adenocarcinoma, HTB-38, ATCC). Cells were seeded at 5000 cells/well in 200 µl of media (DMEM medium+5% FBS) in a 96 well plate and incubated over-night (O.N). Cells were starved in 100 µl of serum free medium (SFM) containing 0.1% FBS, O.N. All lyophilized peptides were dissolved in H2O (prewarmed to 50° C.) and hand-stirred, giving a final concentration of 1 mg/ml. Reconstituted peptides were added in concentrations of 0.003, 0.009, 0.028, 0.084, 0.25, 0.76, 2.28, 6.66, 20 and 60 µg/ml and the cells were incubated for 48 hours.

Cell proliferation was measured using MTT assay: 20 µl of MTT solution ((3-[4,5-Dimethyl-2-thiazolyl]-2,5-diphenyl-2H-tetrazolium bromide, Sigma Cat#M5655, lot#085k5322, 1 gr was dissolved in 200 ml $H_2O$ and filtered, giving a final concentration of 5 mg/ml) were added to each well for 4 hrs, after which the medium was vacuumed and 100 µl of DMSO were added to each well. Absorbance was measured in an ELISA reader at 492 nm.

The results demonstrating the effect of CGEN-GP1 (SEQ ID NO:1) (0.003, 0.009, 0.028, 0.084, 0.25, 0.76, 2.28, 6.66, 20 and 60 µg/ml) on the proliferation of the cell lines HCT116 (Human colorectal carcinoma, CCL-247, ATCC), SW480 (Human colorectal adenocarcinoma, CCL-228, ATCC), HT29 (Human colorectal adenocarcinoma, HTB-38, ATCC) and MCF7 (Human, mammary gland adenocarcinoma, HTB-22, ATCC) are shown in FIGS. 9A, 9B, 9C and 9D, respectively.

The results demonstrating the effect of CGEN-GP5 (SEQ ID NO:29) (0.003, 0.009, 0.028, 0.084, 0.25, 0.76, 2.28, 6.66, 20 and 60 µg/ml) on the proliferation of the cell lines HCT116 (Human colorectal carcinoma, CCL-247, ATCC), SW480 (Human colorectal adenocarcinoma, CCL-228, ATCC), HT29 (Human colorectal adenocarcinoma, HTB-38, ATCC) and MCF7 (Human, mammary gland adenocarcinoma, HTB-22, ATCC) are shown in FIGS. 10A, 10B, 10C and 10D, respectively. The results are presented as percent relative to untreated cells (which was defined as 100).

FIGS. 9 (A, B, C, D) and FIGS. 10 (A, B, C, D) demonstrate that the CGEN-GP1 (SEQ ID NO:1) and the CGEN-GP5 (SEQ ID NO:29) peptides inhibit the proliferation of all cell lines tested in a dose-dependent manner.

Example 10

Analysis of Activity of a Peptide of the Invention in Inhibiting the Production of IFNγ from Isolated Mouse Spleen Cells Treated with IL-18 Plus IL-12

In order to analyze the activity of the bioactive peptides of the invention in inhibiting the production of IFNγ from isolated mouse spleen cells treated with IL-18 plus IL-12, spleen was isolated from two C57black/6 mice and the splenocytes were incubated at a concentration of 2.5 millions per milliliter in medium containing 5% FCS. The cells were stimulated for 24 hours with murine IL-18 (20 ng/mL) plus murine IL-12 (10 ng/mL) with or without CGEN-GP1. In addition, the effect of CGEN-GP1 alone on INFγ secretion from isolated Splenocytes was tested as well. Supernatants were collected and assayed for murine IFNγ using a murine INFγ ELISA kit. (R&D Systems, Human INFγ Quantikine ELISA Kit, Cat # MIF00).

Figure 11:
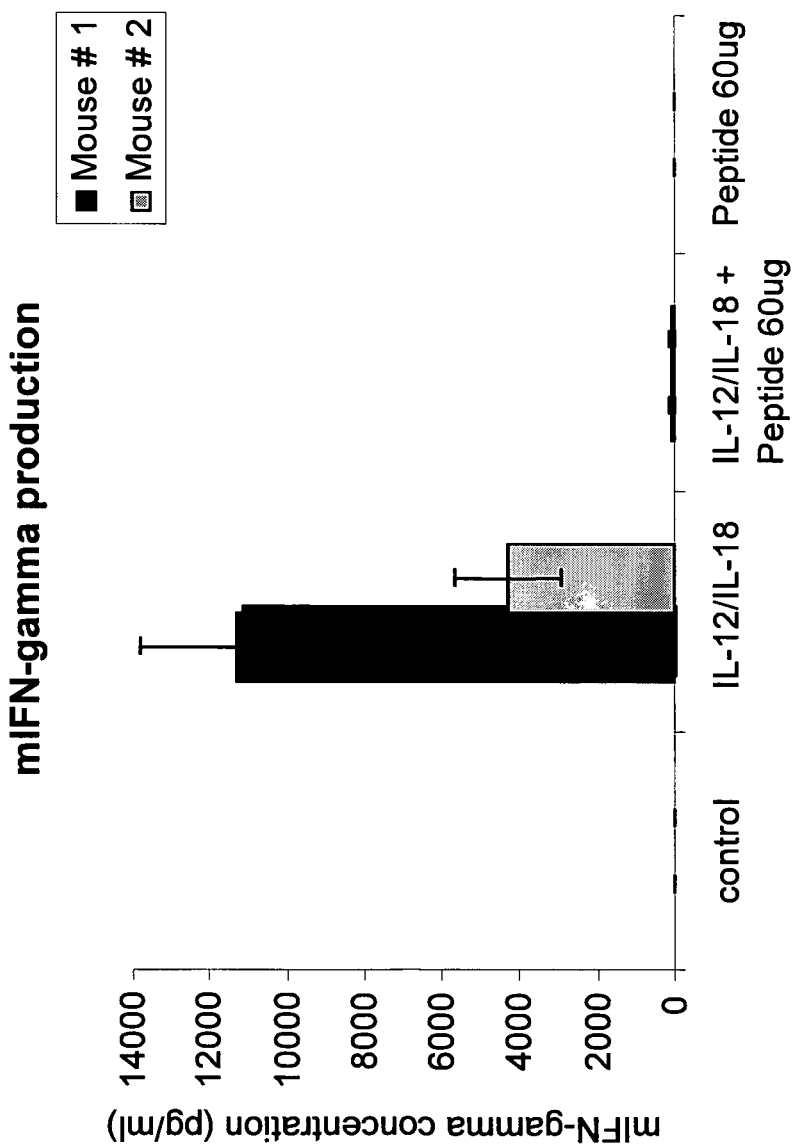
FIG. 11: presents the effect of CGEN-GP1 (SEQ ID NO:1) on the production of IFNγ in isolated mouse (C57Black 6) spleen cells treated with IL-18 plus IL-12. The concentration of IFNγ was measured 24 hours after treatment using mouse IFNγ ELISA (R&D Systems, mouse IFNγ Quantikine ELISA Kit).

FIG. 11 demonstrates that 60 µg/ml or CGEN-GP1 abolishes the secretion of IFNγ from mice Splenocytes following treatment with IL-12 plus IL-18.

Example 11

Analysis of Activity of a Peptide of the Invention in Inhibiting the Secretion of Cytokines in Serum of LPS-Treated Mice CGEN-GP1 (SEQ ID NO:1), as synthesized in Example 1, was analyzed for its ability to inhibit LPS-induced Tumor necrosis factor-α (TNF-α), IL-6, Interferon-gamma (IFN-γ), MIP-2 and MIP-1α secretion into the serum of LPS-treated mice. C57Black/6 mice were injected intraperitoneally (ip) with three doses of CGEN-GP1 (SEQ ID NO:1) (10, 30 or 60 µg per mouse) or saline as a control (5 mice in each group, a total of 25 mice) followed immediately by another ip injection of *E. coli* LPS (10 mg/kg). 90 minutes after treatment with LPS, mice were bled from the orbital plexus and cytokines and chemokines' concentrations were measured using ELISA kits specific to murine TNF-α, IFNγ, MIP-2 or MIP-1α (R&D Systems, ELISA kits, Cat numbers MTA00, MIF00, MM200 and MMA00, respectively). After 6 hours mice were sacrificed and the serum was used to measure TNF-α, IFNγ, IL-6 and MIP-2 using suitable ELISA kits for the murine molecules (R&D Systems, ELISA kits, Cat numbers MTA00, MIF00, M6000B and MM200, respectively).

Figure 12:
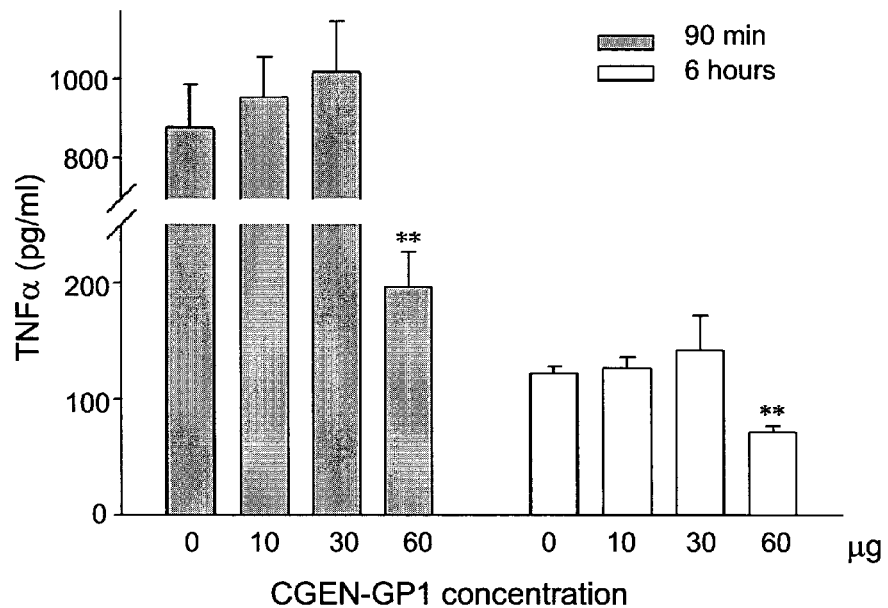
FIG. 12: presents the effect of CGEN-GP1 (SEQ ID NO:1) on LPS-induced TNF-α production in C57Black/6 mice injected intraperitoneal (ip) with LPS together with three doses of the CGEN-GP1 peptide (10, 30 or 60 µg per mouse) or saline as control. The concentration of TNF-α in the serum was measured 90 minutes and 6 hours after LPS challenge using TNF-α ELISA (R&D Systems, mouse TNF-alpha Quantikine ELISA Kit).

FIG. 12 demonstrates that 60 µg of CGEN-GP1 (SEQ ID NO:1) injected i.p to mice inhibited more than 70% of LPS-induced TNF-α secretion in mice serum.

Figure 13:
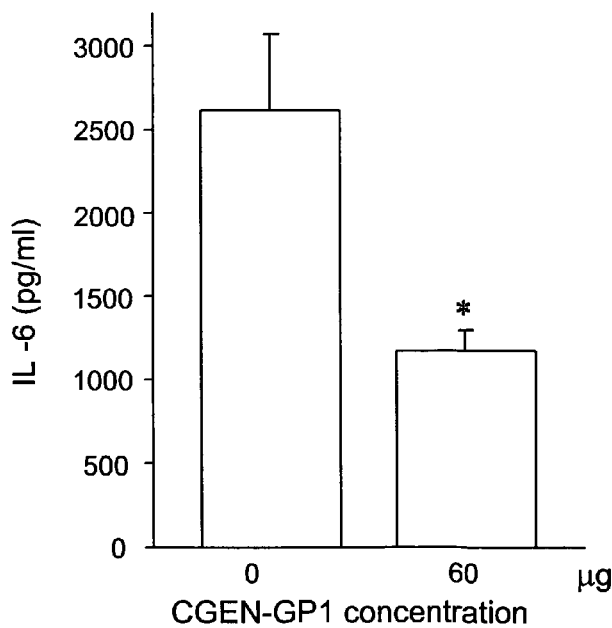
FIG. 13: presents the effect of CGEN-GP1 (SEQ ID NO:1) on LPS-induced IL-6 production in C57Black/6 mice injected intraperitoneally (ip) with LPS together with one dose of the CGEN-GP1 peptide (60 µg per mouse) or saline as control. The concentration of IL-6 in the serum was measured 6 hours after LPS challenge using mouse IL-6 ELISA (R&D Systems, mouse IL-6 Quantikine ELISA Kit).

FIG. 13 demonstrates that 60 µg of CGEN-GP1 (SEQ ID NO:1) injected i.p to mice inhibited 50% of LPS-induced IL-6 secretion in mice serum.

Figure 14:
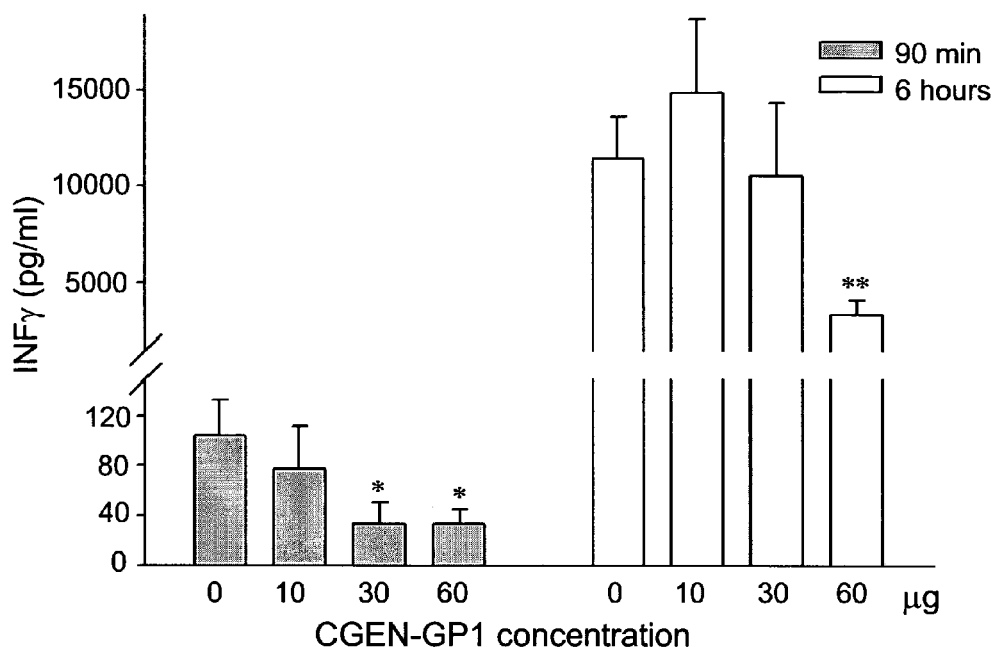
FIG. 14: presents the effect of CGEN-GP1 (SEQ ID NO:1) on LPS-induced IFN-γ production in C57Black 6 mice injected intraperitoneal (ip) with LPS together with three doses of the CGEN-GP1 peptide 10, 30 or 60 µg per mouse) or injected with saline as a control. The concentration of IFN-γ in the serum was measured 90 min and 6 hours after LPS challenge using mouse IFN-γ ELISA (R&D Systems, mouse IFN-γ Quantikine ELISA Kit).

FIG. 14 demonstrates that 60 µg of CGEN-GP1 (SEQ ID NO:1) injected i.p to mice inhibited LPS-induced IFN-γ secretion in mice serum by more than 60%.

Figure 15:
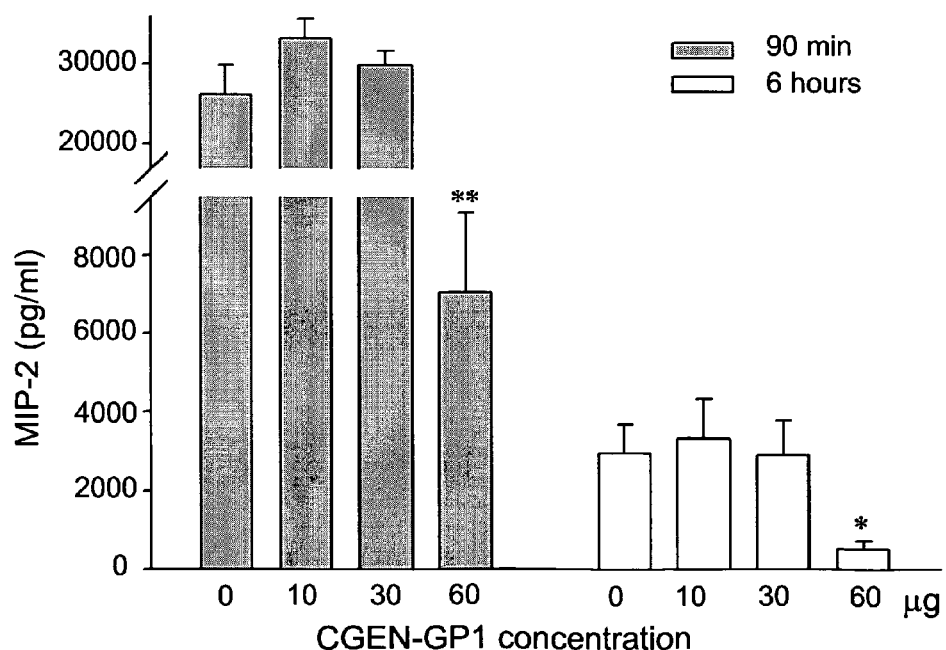
FIG. 15: presents the effect of CGEN-GP1 (SEQ ID NO:1) on LPS-induced MIP-2 production in C57Black/6 mice injected intraperitoneal (ip) with LPS together with three doses of the CGEN-GP1 peptide (10, 30 or 60 µg per mouse) or injected with saline as a control. The concentration of MIP-2 in the serum was measured 90 min and 6 hours after LPS challenge using mouse MIP-2 ELISA (R&D Systems, mouse MIP-2 Quantikine ELISA Kit).

FIG. 15 demonstrates that 60 µg of CGEN-GP1 (SEQ ID NO:1) injected i.p to mice inhibited LPS-induced MIP-2 secretion in mice serum by more than 70%.

Figure 16:
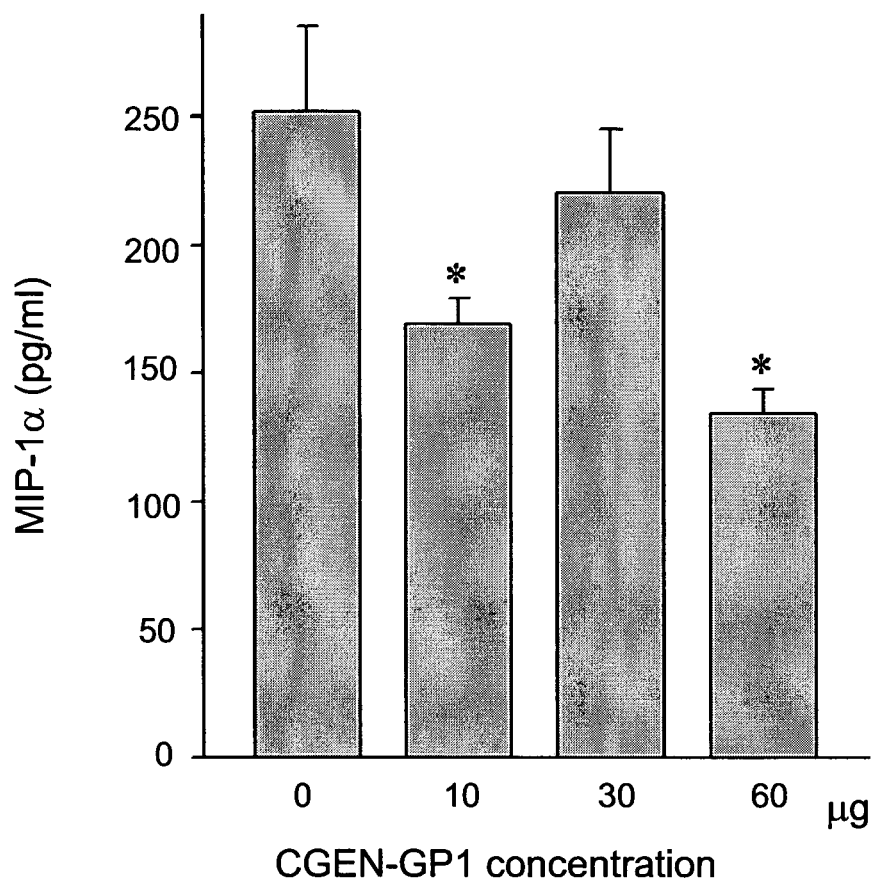
FIG. 16: presents the effect of CGEN-GP1 (SEQ ID NO:1) on LPS-induced MIP-1α production in C57Black/6 mice injected intraperitoneal (ip) with LPS together with three doses of the CGEN-GP1 peptide 10, 30 or 60 µg per mouse) or injected with saline as a control. The concentration of MIP-1α in the serum was measured 90 min after LPS challenge using mouse MIP-1α ELISA (R&D Systems, mouse MIP-1α Quantikine ELISA Kit).

FIG. 16 demonstrates that 60 µg of CGEN-GP1 injected i.p to mice inhibited LPS-induced MIP-1α secretion in mice serum by more than 50%.

Example 12

Design of Conformational Change Blockers of gp96

Conformational changes in proteins play a major role in activity regulation. Natural and synthetic molecules that modulate such changes are of considerable biological importance. Such molecules include allosteric effectors that alter the rapidity of enzyme-catalyzed reactions (J. Monod, et al., *J Mol Biol* 12, 88 (1965)), molecules that shift the oligomerization equilibrium of proteins (Z. Hayouka et al., *Proc Natl Acad Sci USA* 104, 8316 (2007)), and molecules that interfere with transmembrane helix-helix associations (H Yin et al., *Science* 315, 1817 (2007)).

Conformational change modulators of gp96 were designed. The designed peptides were identified using a unique computerized method to interfere with conformational changes involving helix-helix interactions.

A computational approach for sequence-based identification of intra-molecular helix-helix interactions was able to detect interactions that ordinarily difficult to observe experimentally. The computational approach was based on the analysis of correlated mutations in the sequences of a target protein and its homologs (FIG. 17 and FIG. 18).

Such analysis aims at identifying intra-molecular interactions between pairs of amino acid residues (S. S. Choi, et al., *Nat Genet* 37, 1367 (2005); G. B. Gloor, et al., *Biochemistry* 44, 7156 (2005); U Gobel, et al., *Proteins* 18, 309 (1994); S. W. Lockless, et al., *Science* 286, 295 (1999); L. C. Martin, et al., *Bioinformatics* 21, 4116 (2005); F. Pazos, et al., *Comput Appl Biosci* 13, 319 (1997)) facilitated by the introduction of a new category of residue-residue contact prediction into the Critical Assessment of techniques for protein Structure Prediction (CASP) competition (J. M Izarzugaza, et al., *Proteins* 69 Suppl 8, 152 (2007)). Nevertheless, despite these algorithmic advances and the growing availability of sequence data, the signal to noise ratio of correlated mutation analysis remains relatively low, and does not currently allow ab initio structure prediction.

Figure 17A:
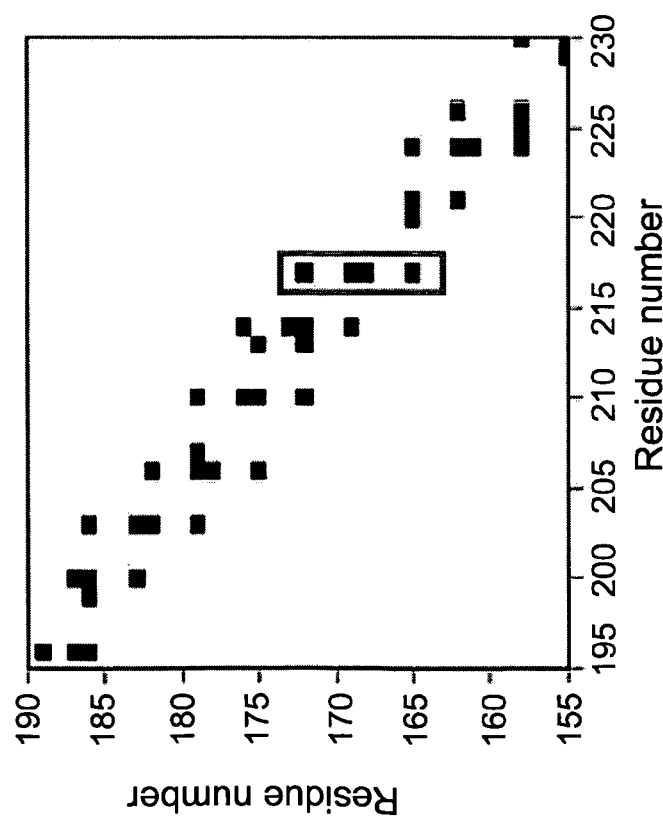
FIGS. 17A and 17B demonstrate an example for a known protein (BAG-1, Protein Data Bank ID 1hx1 (chain B)) that comprises two helices that interact with each other in an anti-parallel manner.
Figure 17B:
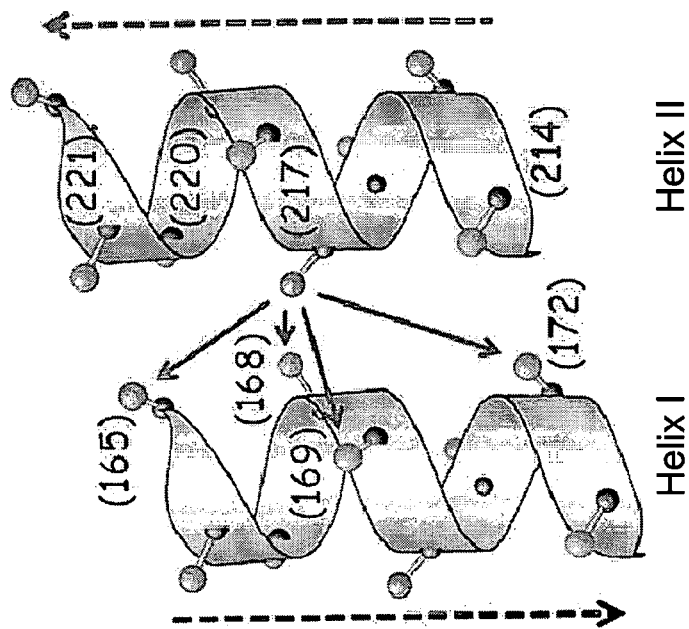
Figures 17C, 17D:
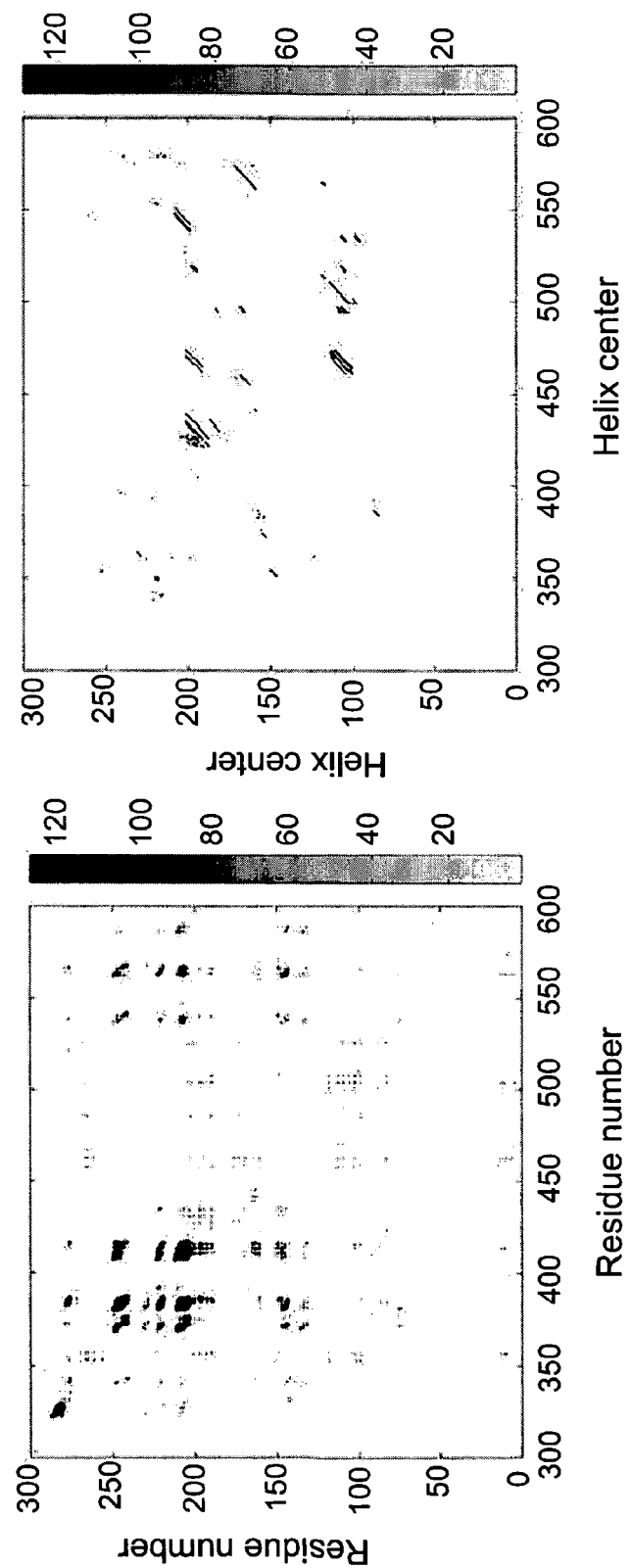
FIG. 17C demonstrates a subset of the residue-residue contact map for gp96 (residues 1-300×300-600) as identified by SVMcon (J. Cheng, P. Baldi, BMC Bioinformatics 8, 113 (2007)
FIG. 17D shows a map of scores based on the Fourier transform of the correlated mutation signal of gp96.
Figure 17E:
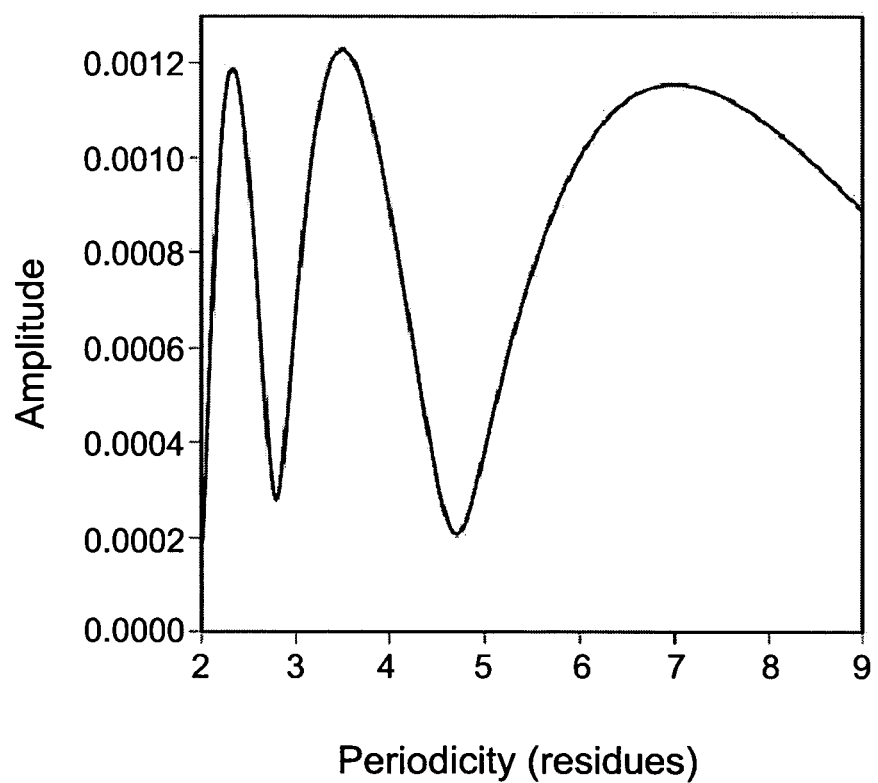
FIG. 17E shows a typical Fourier transform corresponding to the sum of columns in the 21 by 21 matrix that represents the parallel interaction between the segments centered on residues 110 and 470 of gp96.

The detection of interacting segments through correlated mutation analysis is hindered by the thus low signal to noise ratio, when applied naively, e.g., averaging over a sliding window approach. The conceptual new ingredient of the unique in silico approach used herein for identification of peptides capable of acting as conformational change blockers of gp96, was the exploitation of the periodic nature of the correlated mutation data for helix-helix interactions, for which the corresponding periodicity should be around 3.6 amino acids (FIGS. 17A-B). Technically, this was achieved using an appropriate application of the Fourier transform. An interaction was detected by a peak in the absolute value of the Fourier transform of the correlated mutations signal around the typical periodicity (FIG. 17E). Although the transform is one dimensional, it analyses the two dimensional matrix of correlated mutation scores, detecting the periodicity manifested in both interacting segments (FIGS. 17C-D). In this unique technology, used for computerized detection of peptides capable of acting as conformational change blockers of gp96, Fourier transform was introduced to correlated mutations analysis, substantially improving the signal to noise ratio (FIG. 17C vs. FIG. 17D), as well as a "two dimensional" Fourier analysis was employed in protein structure determination.

This newly-developed tool was applied to gp96, and resulted in detection of remarkable peak of the absolute values of the Fourier transform around the expected periodicity.

Using this approach, an interaction between CGEN-GP1 (SEQ ID NO:1) and a helix peptide corresponding to residues 100-137 in gp96 (partner helix) was computationally identified [SEQ ID NO:25].

FIG. 17 shows the identification using the unique computerized method for prediction of helix-helix interactions. FIG. 17A demonstrates residue-residue contact map of two antiparallel helices taken from the solved structure of BAG-1 (PDB id: 1HX1 Chain B) calculated using CSU (V. Sobolev, A. Sorokine, I Prilusky, E. E. Abola, M Edelman, *Bioinformatics* 15, 327 (1999)). FIG. 17B demonstrates a schematic view of two helices interacting through their adjacent faces. This interaction gives rise to the 3.6-residue periodicity that is the basis of our Fourier transform-based approach. Each residue on one helix may interact with 3-4 residues on the other helix spanning a region of 8-9 residues (see rectangle in FIG. 17A). FIG. 17C demonstrates the residue-residue contact map for gp96 as predicted by SVMcon (J. Cheng, et al., *BMC Bioinformatics* 8, 113 (2007)). Typically, in these methods (S. S. Choi, *Nat Genet* 37, 1367 (2005); G. B. Gloor, *Biochemistry* 44, 7156 (2005); U Gobel, et al., *Proteins* 18, 309 (1994); L. C. Martin, et al., *Bioinformatics* 21, 4116 (2005); F. Pazos, et al., *Comput Appl Biosci* 13, 319 (1997); J. Cheng, et al., *BMC Bioinformatics* 8, 113 (2007); S. D. Dunn, et al., *Bioinformatics* 24, 333 (2008); G. Shackelford, et al., *Proteins* 69 Suppl 8, 159 (2007)) the sequences of the protein of interest and its homologs are used for constructing a multiple sequence alignment (MSA). Correlations between columns in the MSA (correlated mutations) point to predicted residue-residue interactions. Until today however, known contact map prediction technologies suffered from low recall and low precision. These drawbacks in helix-helix interactions identification have now been solved by the unique in silico approach used herein for identification of peptides capable of acting as conformational change blockers of gp96. FIG. 17D shows a map of scores based on the Fourier transform of the correlated mutation signal of gp96. In order to detect helix-helix interactions, for each pair of 21-residue long segments two vectors of sums of the predicted residue-residue scores were calculated: one for the rows and one for the columns of the corresponding 21 by 21 matrix. For the detection of parallel helix-helix interactions only the principal (i.e. major) diagonal and its 4 neighboring diagonals from each side were summed. For anti-parallel interactions, the minor diagonal was similarly utilized. The two vectors are then Fourier transformed. A joint score was calculated that is non-zero only if a significant peak representing a periodicity of about 3.6 residues exists in the Fourier Transform of both the 'rows' and the 'column' vectors. FIGS. 17C and 17D demonstrate how the Fourier Transform enhances the signal to noise ratio and enables reliable predictions of parallel helix-helix interaction in gp96. FIG. 17E shows a typical Fourier transform corresponding to the sum of columns in the 21 by 21 matrix that represents the parallel interaction between the segments centered on residues 110 and 470 of gp96.

Figures 18A, 18B:
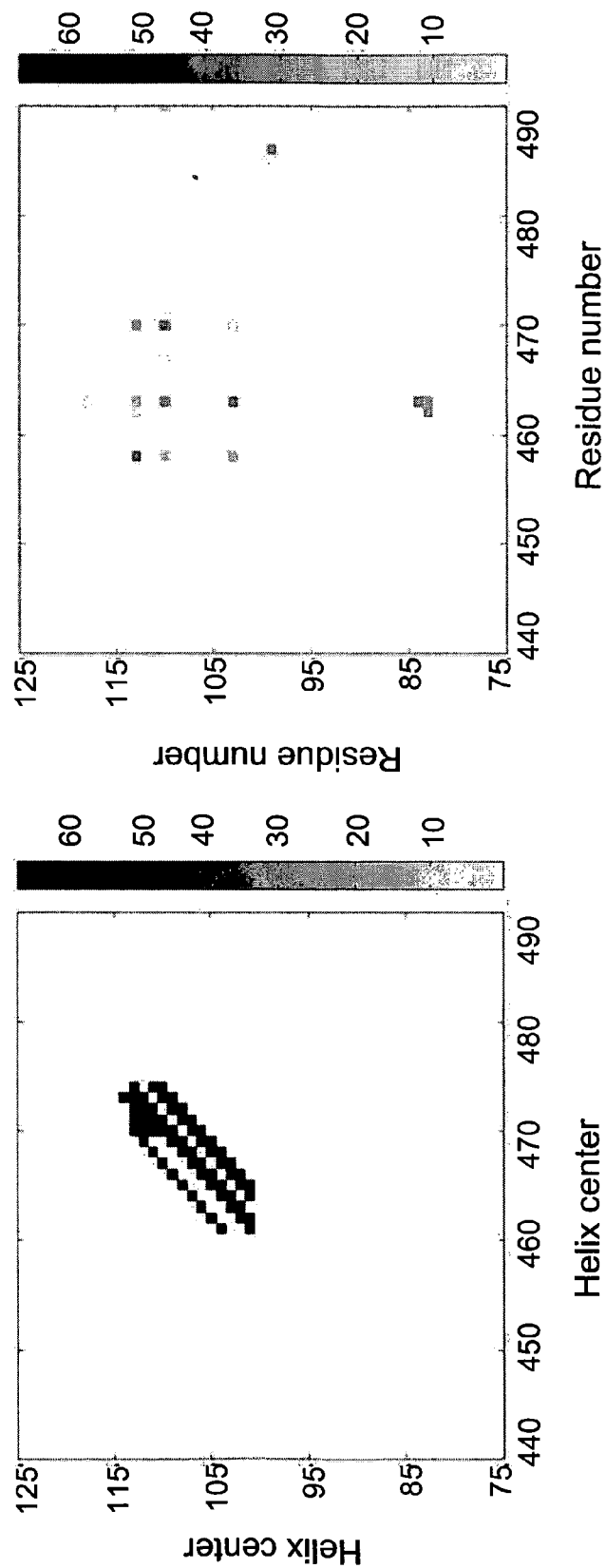
FIG. 18A presents zoomed in view of the most prominent parallel helix-helix signal of gp96, as shown in FIG. 17D.
FIG. 18B presents zoomed in view of its corresponding residue-residue contact map, as shown in FIG. 17C.

FIG. 18 presents In Silico detection of a helix-helix interaction in gp96. FIG. 18A presents zoomed in view of the most prominent parallel helix-helix signal of gp96, which appeared in FIG. 17D. FIG. 18B presents zoomed in view of its corresponding residue-residue contact map, which appeared in FIG. 17C.

Example 13

Analysis of CGEN-GP1 Binding to Recombinant gp96 Protein

The capability of CGEN-GP1 peptide (SEQ ID NO:1) to specifically bind to recombinant gp96 protein was investigated using the BIACORE technology, measuring protein-protein interaction and binding affinity. The technology is based on surface plasmon resonance (SPR), an optical phenomenon that enables detection of unlabeled interactants in real time. The SPR-based biosensors can be used in determination of active concentration, screening and characterization in terms of both affinity and kinetics.

Peptide-protein interaction was analyzed using surface plasmon resonance. Analysis of the interaction between CGEN-GP1 peptide (SEQ ID NO: 1) and recombinant, canine gp96 protein (Cat # G3057-41, lot # L7042464, USbiological, Swampscott, Mass.) was conducted using the BIAcore biosensor (Pharmacia Biosensor, Uppsala, Sweden). Gp96 was immobilized directly to a CM5 sensor chip (2000 resonance units (RU)). Solution containing five different concentrations of CGEN-GP1 peptide (156, 312, 625, 1250 and 2500 nM) was injected into the sample chamber of the BIACORE device and the interaction was monitored for 5 minutes using surface plasmon resonance. As a background, the solutions were also injected onto an empty flow cell with no immobilized ligand and the binding levels achieved were subtracted. Data was analyzed using BIAevaluation software.

Figure 19:
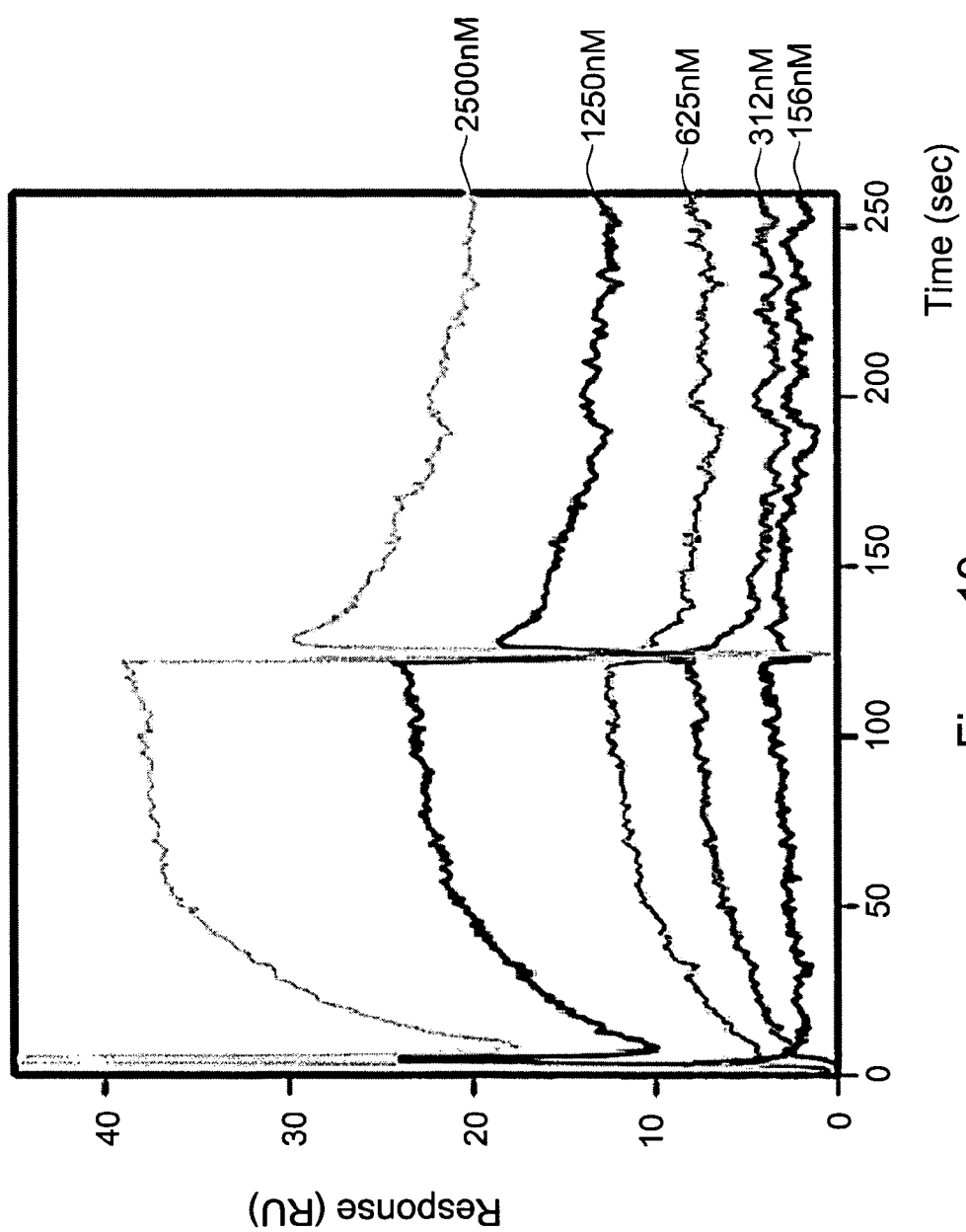
FIG. 19 shows the results of the analysis of CGEN-GP1 (SEQ ID NO:1) interaction with its parent protein GP96 (SEQ ID NO:13).
Figure 21:
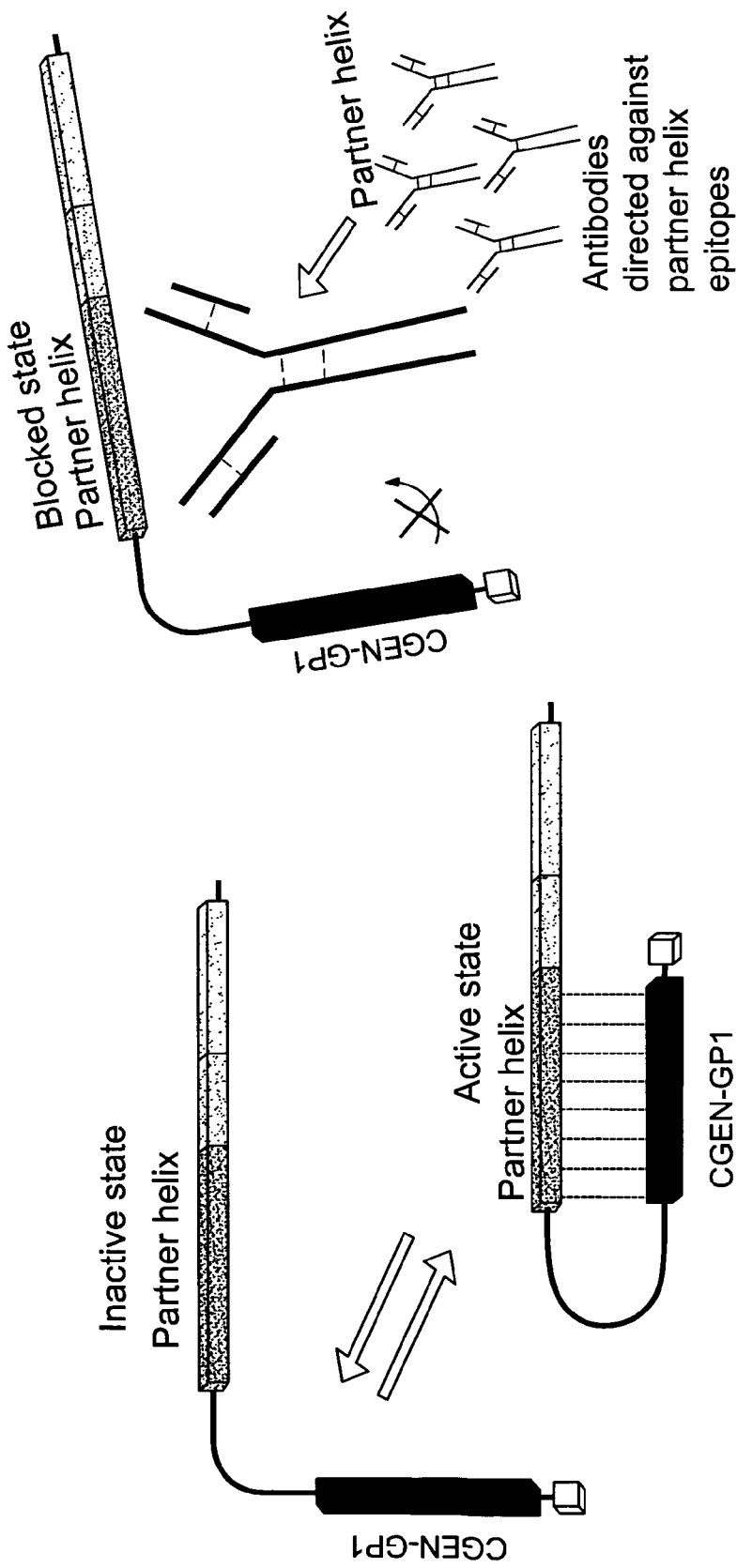
FIG. 21 shows a schematic drawing demonstrating that antibodies aimed against epitopes derived from a helix partner have the capability to block the helix-helix interaction within the gp96 protein and thereby cause a biological effect resembling the biological activity achieved by a bioactive peptide of the invention.

FIG. 19 shows the results of the analysis of CGEN-GP1 interaction with its parent protein gp96 and shows that CGEN-GP1 binds to its parent protein gp96 in a dose dependent manner. Significant binding is detected from 0.3 to 2.5 μM. The affinity constant of the interaction between CGEN-GP1 and gp96 was determined by direct kinetic analysis. The 1:1 Langmuir binding model was used to fit kinetic data giving $k_a=3.99*10^3 M^{-1}*sec^{-1}$, and $k_d=8.45*10^{-4} sec^{-1}$, thus $K_D=2.12*10^{-7}M$.

Example 14

Biological Confirmation for the Computationally Identified Interaction Between CGEN-GP1 (SEQ ID NO: 1) and its Helix Partner (SEQ ID NO: 25)

In order to evaluate whether the two predicted α-helices (CGEN-GP1 (SEQ ID NO: 1) and its helix partner (SEQ ID NO: 25)) bind to each other in the GP96 protein, a co-incubation of the two peptides was analyzed for its ability to eliminate the biological activity of CGEN-GP1.

Pre-incubation for 30 minutes of 666 nM CGEN-GP1 peptide (SEQ ID NO:1) with an equimolar concentration of the helix partner (SEQ ID NO:25) was carried out at room temperature. The effect of CGEN-GP1 peptide (SEQ ID NO:1) alone, or the helix partner (SEQ ID NO:25) alone or the pre-incubated CGEN-GP1 peptide (SEQ ID NO:1) with helix partner (SEQ ID NO:25) on LPS-induced TNFα secretion from THP1 cells was tested as described in Example 4 herein.

FIG. 20 presents proposed potential mechanism of action of CGEN-GP1. FIG. 20A presents schematic diagram of a conformational change in a protein, and FIG. 20B shows the blockage of the conformational change in a protein by a peptide corresponding to one of the helices. FIG. 20C demonstrates that according to this potential mechanism of action, pre-incubation of the bioactive peptide (SEQ ID NO: 1) with a peptide corresponding to its counterpart helix (SEQ ID NO:25) abolishes the inhibitory effect of SEQ ID NO: 1.

The experimental data were consistent with the computationally predicted mode of action, in which the biological inhibitory activity of the peptides takes place upon their binding to the segment corresponding to the counterpart helix within the parent protein (FIG. 20D). Indeed, these results support the existence of both an active ("close") conformation, in which the two segments interact with each other, and an inactive ("open") conformation, in which the two segments do not interact (FIG. 20D).

FIG. 20D presents the results of pre-incubation of 333 nM CGEN-GP1 peptide (SEQ ID NO:1) with an equimolar concentration of a peptide corresponding to its counterpart helix (SEQ ID NO:25), leading to attenuated the activity of CGEN-GP1.

As shown in FIG. 20D, the biological effect of CGEN-GP1 (SEQ ID NO:1) bioactive peptide, that was demonstrated herein in FIG. 6 was abolished in the presence of partner helix peptide (SEQ ID NO:25).

Example 15

Antibodies

Reagents other than peptides are also used to inhibit the formation of the helix-helix interactions between the segment corresponding to residues 444-480 and the segment corresponding to residues 100-137 of gp96. Antibodies that specifically bind to an epitope in partner helix peptides of CGEN-GP1 (SEQ ID NO: 25-26), or an epitope in the segment corresponding to CGEN-GP1 (SEQ ID NO: 1) itself are highly effective to inhibit the formation of the helix-helix interactions between the segment corresponding to residues 444-480 and the segment corresponding to residues 100-137, and thereby to act as antagonists of gp96.

FIG. 21 shows a schematic drawing demonstrating that antibodies aimed against an epitope derived from the helix partner have the capability to block the helix-helix interaction within the gp96 protein and thereby cause a biological effect resembling the biological activity achieved by CGEN-GP1.

Thus, antibodies that specifically bind to an epitope in a helix partner peptide of CGEN-GP1 or an epitope in the segment corresponding to CGEN-GP1 or homologs or fragments thereof are used for treating wide range of conditions, disorders and diseases, selected from but not limited to autoimmune diseases, sepsis, chronic and acute inflammatory diseases, gastrointestinal inflammatory diseases, gastrointestinal malignancies, diseases involving inflammation of the respiratory tract, autoinflammatory diseases, ischemia-reperfusion injury related disorders, cardiovascular diseases, heavy metal induced diseases, kidney diseases, infections diseases, cancer, preterm birth, complications of surgery and surgical interventions related to presence of endotoxin and bacterial infections, and acute allograft rejection after organ transplantation.

Example 16

Orthologs

The sequences of the CGEN-GP1 (SEQ ID NO: 1), CGEN-GP4 (SEQ ID NO: 27), and CGEN-GP5 (SEQ ID NO: 29), corresponding to amino acid residues 444-480, 450-480, and 454-488, respectively, in the human gp96 protein sequence (GenBank Accession number: gi|4507677) (SEQ ID NO: 13), are highly conserved throughout other species and orthologs, as can be seen from FIGS. 22, 23 and 24, respectively.

FIG. 22 shows a multiple alignment comparison of the sequence of CGEN-GP1 (SEQ ID NO:1) and the homologous sequences derived from >gi|15233740_0|[*Arabidopsis thaliana*], >gi|27807263_0|[*Bos taurus*], >gi|544242_0|[*Hordeum vulgare*], >gi|462013_0|[*Catharanthus roseus*], >gi|17865698_0|[*Sus scrofa*], >gi|45383562_0|[*Gallus gallus*], >gi|6015101_0|[*Oryctolagus cuniculus*], >gi|109098491_0|[*Macaca fascicularis*], >gi|6755863_0|[*Mus musculus*], >gi|75070529_0|[*Pongo pygmaeus*], >gi|50979166_0|[*Canis familiaris*], corresponding to SEQ ID NOs: 14-24.

FIG. 23 shows a multiple alignment comparison of the sequence of CGEN-GP4 (SEQ ID NO:27) and the orthologous sequences derived >gi:90076963 (*Macaca fascicularis*), >gi:37805386 (*Xenopus laevis*), >gi:403496 (*Canis familiaris*), >gi:74190331 (*Mus musculus*), >gi:39645914 (*Danio rerio*), >gi:210032364 (*Rattus norvegicus*) and >gi:75775555 (*Bos Taurus*), corresponding to SEQ ID NOs: 35-41.

FIG. 24 shows a multiple alignment comparison of the sequence of CGEN-GP5 (SEQ ID NO:29) and the orthologous sequences derived from >gi:114646591_*Pan troglodytes*, >gi:109098490_*Macaca mulatta*, >gi:67970925_*Macaca fascicularis*, >gi:55731899_*Pongo abelii*, >gi:74190331_*Mus musculus*, >gi:210032364_*Rattus norvegicus*, >gi:75775555_*Bos taurus*, >gi:2239252_*Sus scrofa*, >gi:149742973_*Equus caballus*, >gi:403496_*Canis familiaris* and >gi:194220333_*Gallus gallus*, corresponding to SEQ ID NOs: 42-52.

The invention claimed is:

1. An isolated peptide consisting of the amino acid sequence of SEQ ID NO:1.

2. A homolog of the isolated peptide of claim 1, consisting of:
an amino acid sequence selected from the group consisting of the amino acid sequence of SEQ ID NO:4, the amino acid sequence of SEQ ID NO:14, the amino acid sequence of SEQ ID NO:15, the amino acid sequence of SEQ ID NO:16, the amino acid sequence of SEQ ID NO:17, the amino acid sequence of SEQ ID NO:18, the amino acid sequence of SEQ ID NO:19, the amino acid sequence of SEQ ID NO:20, the amino acid sequence of SEQ ID NO:21, the amino acid sequence of SEQ ID NO:22, the amino acid sequence of SEQ ID NO:23, the amino acid sequence of SEQ ID NO:24, the amino acid sequence of SEQ ID NO:35, the amino acid sequence of SEQ ID NO:36, the amino acid sequence of SEQ ID NO:37, the amino acid sequence of SEQ ID NO:38, the amino acid sequence of SEQ ID NO:39, the amino acid sequence of SEQ ID NO:40, the amino acid sequence of SEQ ID NO:41, the amino acid sequence of SEQ ID NO:42, the amino acid sequence of SEQ ID NO:43, the amino acid sequence of SEQ ID NO:44, the amino acid sequence of SEQ ID NO:45, the amino acid sequence of SEQ ID NO:46, the amino acid sequence of SEQ ID NO:47, the amino acid sequence of SEQ ID NO:48, the amino acid sequence of SEQ ID NO:49, the amino acid sequence of SEQ ID NO:50, the amino acid sequence of SEQ ID NO:51, and the amino acid sequence of SEQ ID NO:52.

3. A fusion protein comprising the peptide of claim 1.

4. A pharmaceutical composition comprising the peptide of claim 1 and a pharmaceutically acceptable carrier.

* * * * *

SEQUENCE LISTING

```
<160> NUMBER OF SEQ ID NOS: 52

<210> SEQ ID NO 1
<211> LENGTH: 37
<212> TYPE: PRT
<213> ORGANISM: Artificial
<220> FEATURE:
<223> OTHER INFORMATION: Synthetic polypeptide

<400> SEQUENCE: 1

Leu Asn Val Ser Arg Glu Thr Leu Gln Gln His Lys Leu Leu Lys Val
1               5                   10                  15
```

```
Ile Arg Lys Lys Leu Val Arg Lys Thr Leu Asp Met Ile Lys Lys Ile
            20                  25                  30

Ala Asp Asp Lys Tyr
        35
```

<210> SEQ ID NO 2
<211> LENGTH: 35
<212> TYPE: PRT
<213> ORGANISM: Artificial
<220> FEATURE:
<223> OTHER INFORMATION: Synthetic polypeptide

<400> SEQUENCE: 2

```
Met Met Lys Leu Ile Ile Asn Ser Leu Tyr Lys Asn Lys Glu Ile Phe
1               5                   10                  15

Leu Arg Glu Leu Ile Ser Asn Ala Ser Asp Ala Leu Asp Lys Ile Arg
            20                  25                  30

Leu Ile Ser
        35
```

<210> SEQ ID NO 3
<211> LENGTH: 32
<212> TYPE: PRT
<213> ORGANISM: Artificial
<220> FEATURE:
<223> OTHER INFORMATION: Synthetic polypeptide

<400> SEQUENCE: 3

```
Ile Tyr Val Trp Ser Ser Lys Thr Glu Thr Val Glu Glu Pro Met Glu
1               5                   10                  15

Glu Glu Glu Ala Ala Lys Glu Glu Lys Glu Glu Ser Asp Asp Glu Ala
            20                  25                  30
```

<210> SEQ ID NO 4
<211> LENGTH: 57
<212> TYPE: PRT
<213> ORGANISM: Artificial
<220> FEATURE:
<223> OTHER INFORMATION: Synthetic polypeptide

<400> SEQUENCE: 4

```
Lys Gly Val Val Asp Ser Asp Asp Leu Pro Leu Asn Val Ser Arg Glu
1               5                   10                  15

Thr Leu Gln Gln His Lys Leu Leu Lys Val Ile Arg Lys Lys Leu Val
            20                  25                  30

Arg Lys Thr Leu Asp Met Ile Lys Ile Ala Asp Lys Tyr Asn
            35                  40                  45

Asp Thr Phe Trp Lys Glu Phe Gly Thr
        50                  55
```

<210> SEQ ID NO 5
<211> LENGTH: 55
<212> TYPE: PRT
<213> ORGANISM: Artificial
<220> FEATURE:
<223> OTHER INFORMATION: Synthetic polypeptide

<400> SEQUENCE: 5

```
Lys Phe Ala Phe Gln Ala Glu Val Asn Arg Met Met Lys Leu Ile Ile
1               5                   10                  15

Asn Ser Leu Tyr Lys Asn Lys Glu Ile Phe Leu Arg Glu Leu Ile Ser
            20                  25                  30

Asn Ala Ser Asp Ala Leu Asp Lys Ile Arg Leu Ile Ser Leu Thr Asp
```

```
                    35                  40                  45

Glu Asn Ala Leu Ser Gly Asn
         50                  55

<210> SEQ ID NO 6
<211> LENGTH: 52
<212> TYPE: PRT
<213> ORGANISM: Artificial
<220> FEATURE:
<223> OTHER INFORMATION: Synthetic polypeptide

<400> SEQUENCE: 6

Lys Lys Tyr Ser Gln Phe Ile Asn Phe Pro Ile Tyr Val Trp Ser Ser
1               5                   10                  15

Lys Thr Glu Thr Val Glu Glu Pro Met Glu Glu Glu Ala Ala Lys
            20                  25                  30

Glu Glu Lys Glu Glu Ser Asp Asp Glu Ala Ala Val Glu Glu Glu Glu
        35                  40                  45

Glu Glu Lys Lys
    50

<210> SEQ ID NO 7
<211> LENGTH: 111
<212> TYPE: DNA
<213> ORGANISM: Artificial
<220> FEATURE:
<223> OTHER INFORMATION: Synthetic polynucleotide

<400> SEQUENCE: 7
ttgaatgttt cccgcgagac tcttcagcaa cataaactgc ttaaggtgat taggaagaag      60
cttgttcgta aaacgctgga catgatcaag aagattgctg atgataaata c              111

<210> SEQ ID NO 8
<211> LENGTH: 105
<212> TYPE: DNA
<213> ORGANISM: Artificial
<220> FEATURE:
<223> OTHER INFORMATION: Synthetic polynucleotide

<400> SEQUENCE: 8
atgatgaaac ttatcatcaa ttcattgtat aaaaataaag agattttcct gagagaactg      60
atttcaaatg cttctgatgc tttagataag ataaggctaa tatca                     105

<210> SEQ ID NO 9
<211> LENGTH: 96
<212> TYPE: DNA
<213> ORGANISM: Artificial
<220> FEATURE:
<223> OTHER INFORMATION: Synthetic polynucleotide

<400> SEQUENCE: 9
atttatgtat ggagcagcaa gactgaaact gttgaggagc ccatggagga agaagaagca      60
gccaaagaag agaaagaaga atctgatgat gaagct                                96

<210> SEQ ID NO 10
<211> LENGTH: 171
<212> TYPE: DNA
<213> ORGANISM: Artificial
<220> FEATURE:
<223> OTHER INFORMATION: Synthetic polynucleotide

<400> SEQUENCE: 10
aagggtgtgg tggactcaga tgatctcccc ttgaatgttt cccgcgagac tcttcagcaa      60
```

```
cataaactgc ttaaggtgat taggaagaag cttgttcgta aaacgctgga catgatcaag    120
aagattgctg atgataaata caatgatact ttttggaaag aatttggtac c             171

<210> SEQ ID NO 11
<211> LENGTH: 165
<212> TYPE: DNA
<213> ORGANISM: Artificial
<220> FEATURE:
<223> OTHER INFORMATION: Synthetic polynucleotide

<400> SEQUENCE: 11
aagtttgcct tccaagccga agttaacaga atgatgaaac ttatcatcaa ttcattgtat    60
aaaaataaag agattttcct gagagaactg atttcaaatg cttctgatgc tttagataag   120
ataaggctaa tatcactgac tgatgaaaat gctctttctg aaat                    165

<210> SEQ ID NO 12
<211> LENGTH: 156
<212> TYPE: DNA
<213> ORGANISM: Artificial
<220> FEATURE:
<223> OTHER INFORMATION: Synthetic polynucleotide

<400> SEQUENCE: 12
aaaaaatatt cacagttcat aaactttcct atttatgtat ggagcagcaa gactgaaact    60
gttgaggagc ccatggagga agaagaagca gccaaagaag agaaagaaga atctgatgat   120
gaagctgcag tagaggaaga agaagaagaa aagaaa                             156

<210> SEQ ID NO 13
<211> LENGTH: 803
<212> TYPE: PRT
<213> ORGANISM: Homo sapiens

<400> SEQUENCE: 13

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190
```

```
Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
        210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
        290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
                340                 345                 350

Asp Glu Tyr Lys Ala Phe Tyr Lys Ser Phe Ser Lys Glu Ser Asp Asp
            355                 360                 365

Pro Met Ala Tyr Ile His Phe Thr Ala Glu Gly Glu Val Thr Phe Lys
370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
                420                 425                 430

Val Lys Gly Val Val Asp Ser Asp Asp Leu Pro Leu Asn Val Ser Arg
            435                 440                 445

Glu Thr Leu Gln Gln His Lys Leu Leu Lys Val Ile Arg Lys Lys Leu
        450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
        530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
```

```
                610                 615                 620
Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
                660                 665                 670

Ile Ser Thr Asn Tyr Tyr Ala Ser Gln Lys Lys Thr Phe Glu Ile Asn
                675                 680                 685

Pro Arg His Pro Leu Ile Arg Asp Met Leu Arg Arg Ile Lys Glu Asp
                690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
                740                 745                 750

Ala Lys Val Glu Glu Pro Glu Glu Pro Glu Glu Thr Ala Glu
            755                 760                 765

Asp Thr Thr Glu Asp Thr Gln Asp Glu Glu Met Asp Val
770                 775                 780

Gly Thr Asp Glu Glu Glu Thr Ala Lys Ser Thr Ala Glu Lys
785                 790                 795                 800

Asp Glu Leu

<210> SEQ ID NO 14
<211> LENGTH: 37
<212> TYPE: PRT
<213> ORGANISM: Artificial
<220> FEATURE:
<223> OTHER INFORMATION: Synthetic polypeptide

<400> SEQUENCE: 14

Leu Asn Val Ser Arg Glu Met Leu Gln Gln His Ser Ser Leu Lys Thr
1               5                   10                  15

Ile Lys Lys Lys Leu Ile Arg Lys Ala Leu Asp Met Ile Arg Lys Leu
            20                  25                  30

Ala Glu Glu Asp Pro
        35

<210> SEQ ID NO 15
<211> LENGTH: 37
<212> TYPE: PRT
<213> ORGANISM: Artificial
<220> FEATURE:
<223> OTHER INFORMATION: Synthetic polypeptide

<400> SEQUENCE: 15

Leu Asn Val Ser Arg Glu Thr Leu Gln Gln His Lys Leu Leu Lys Val
1               5                   10                  15

Ile Arg Lys Lys Leu Val Arg Lys Thr Leu Asp Met Ile Lys Lys Ile
            20                  25                  30

Ala Asp Glu Lys Tyr
        35

<210> SEQ ID NO 16
<211> LENGTH: 37
<212> TYPE: PRT
<213> ORGANISM: Artificial
```

```
<220> FEATURE:
<223> OTHER INFORMATION: Synthetic polypeptide

<400> SEQUENCE: 16

Leu Asn Val Ser Arg Glu Met Leu Gln Gln His Ser Ser Leu Lys Thr
1               5                   10                  15

Ile Lys Lys Lys Leu Ile Arg Lys Ala Leu Asp Met Ile Arg Lys Leu
                20                  25                  30

Ala Glu Glu Asp Pro
            35

<210> SEQ ID NO 17
<211> LENGTH: 37
<212> TYPE: PRT
<213> ORGANISM: Artificial
<220> FEATURE:
<223> OTHER INFORMATION: Synthetic polypeptide

<400> SEQUENCE: 17

Leu Asn Val Ser Arg Glu Met Leu Gln Gln His Ser Ser Leu Lys Thr
1               5                   10                  15

Ile Lys Lys Lys Leu Ile Arg Lys Ala Leu Asp Met Ile Arg Lys Ile
                20                  25                  30

Ala Asp Glu Asp Pro
            35

<210> SEQ ID NO 18
<211> LENGTH: 37
<212> TYPE: PRT
<213> ORGANISM: Artificial
<220> FEATURE:
<223> OTHER INFORMATION: Synthetic polypeptide

<400> SEQUENCE: 18

Leu Asn Val Ser Arg Glu Thr Leu Gln Gln His Lys Leu Leu Lys Val
1               5                   10                  15

Ile Arg Lys Lys Leu Val Arg Lys Thr Leu Asp Met Ile Lys Lys Ile
                20                  25                  30

Ala Asp Glu Lys Tyr
            35

<210> SEQ ID NO 19
<211> LENGTH: 37
<212> TYPE: PRT
<213> ORGANISM: Artificial
<220> FEATURE:
<223> OTHER INFORMATION: Synthetic polypeptide

<400> SEQUENCE: 19

Leu Asn Val Ser Arg Glu Thr Leu Gln Gln His Lys Leu Leu Lys Val
1               5                   10                  15

Ile Arg Lys Lys Leu Val Arg Lys Thr Leu Asp Met Ile Lys Lys Ile
                20                  25                  30

Ala Glu Glu Lys Tyr
            35

<210> SEQ ID NO 20
<211> LENGTH: 37
<212> TYPE: PRT
<213> ORGANISM: Artificial
<220> FEATURE:
<223> OTHER INFORMATION: Synthetic polypeptide

<400> SEQUENCE: 20
```

```
Leu Asn Val Ser Arg Glu Thr Leu Gln Gln His Lys Leu Leu Lys Val
1               5                   10                  15

Ile Arg Lys Lys Leu Val Arg Lys Thr Leu Asp Met Ile Lys Lys Ile
            20                  25                  30

Ala Asp Glu Lys Tyr
        35

<210> SEQ ID NO 21
<211> LENGTH: 37
<212> TYPE: PRT
<213> ORGANISM: Artificial
<220> FEATURE:
<223> OTHER INFORMATION: Synthetic polypeptide

<400> SEQUENCE: 21

Leu Asn Val Ser Arg Glu Thr Leu Gln Gln His Lys Leu Leu Lys Val
1               5                   10                  15

Ile Arg Lys Lys Leu Val Arg Lys Thr Leu Asp Met Ile Lys Lys Ile
            20                  25                  30

Ala Asp Asp Lys Tyr
        35

<210> SEQ ID NO 22
<211> LENGTH: 37
<212> TYPE: PRT
<213> ORGANISM: Artificial
<220> FEATURE:
<223> OTHER INFORMATION: Synthetic polypeptide

<400> SEQUENCE: 22

Leu Asn Val Ser Arg Glu Thr Leu Gln Gln His Lys Leu Leu Lys Val
1               5                   10                  15

Ile Arg Lys Lys Leu Val Arg Lys Thr Leu Asp Met Ile Lys Lys Ile
            20                  25                  30

Ala Asp Glu Lys Tyr
        35

<210> SEQ ID NO 23
<211> LENGTH: 37
<212> TYPE: PRT
<213> ORGANISM: Artificial
<220> FEATURE:
<223> OTHER INFORMATION: Synthetic polypeptide

<400> SEQUENCE: 23

Leu Asn Val Ser Arg Glu Thr Leu Gln Gln His Lys Leu Leu Lys Val
1               5                   10                  15

Ile Arg Lys Lys Leu Val Arg Lys Thr Leu Asp Met Ile Lys Lys Ile
            20                  25                  30

Ala Asp Asp Lys Tyr
        35

<210> SEQ ID NO 24
<211> LENGTH: 37
<212> TYPE: PRT
<213> ORGANISM: Artificial
<220> FEATURE:
<223> OTHER INFORMATION: Synthetic polypeptide

<400> SEQUENCE: 24

Leu Asn Val Ser Arg Glu Thr Leu Gln Gln His Lys Leu Leu Lys Val
1               5                   10                  15
```

```
Ile Arg Lys Lys Leu Val Arg Lys Thr Leu Asp Met Ile Lys Lys Ile
            20                  25                  30

Ala Asp Glu Lys Tyr
        35

<210> SEQ ID NO 25
<211> LENGTH: 38
<212> TYPE: PRT
<213> ORGANISM: Artificial
<220> FEATURE:
<223> OTHER INFORMATION: Synthetic polypeptide

<400> SEQUENCE: 25

Phe Leu Arg Glu Leu Ile Ser Asn Ala Ser Asp Ala Leu Asp Lys Ile
1               5                   10                  15

Arg Leu Ile Ser Leu Thr Asp Glu Asn Ala Leu Ser Gly Asn Glu Glu
            20                  25                  30

Leu Thr Val Lys Ile Lys
        35

<210> SEQ ID NO 26
<211> LENGTH: 58
<212> TYPE: PRT
<213> ORGANISM: Artificial
<220> FEATURE:
<223> OTHER INFORMATION: Synthetic polypeptide

<400> SEQUENCE: 26

Ile Asn Ser Leu Tyr Lys Asn Lys Glu Ile Phe Leu Arg Glu Leu Ile
1               5                   10                  15

Ser Asn Ala Ser Asp Ala Leu Asp Lys Ile Arg Leu Ile Ser Leu Thr
            20                  25                  30

Asp Glu Asn Ala Leu Ser Gly Asn Glu Glu Leu Thr Val Lys Ile Lys
        35                  40                  45

Cys Asp Lys Glu Lys Asn Leu Leu His Val
    50                  55

<210> SEQ ID NO 27
<211> LENGTH: 31
<212> TYPE: PRT
<213> ORGANISM: Artificial
<220> FEATURE:
<223> OTHER INFORMATION: Synthetic polypeptide

<400> SEQUENCE: 27

Thr Leu Gln Gln His Lys Leu Leu Lys Val Ile Arg Lys Lys Leu Val
1               5                   10                  15

Arg Lys Thr Leu Asp Met Ile Lys Ile Ala Asp Asp Lys Tyr
            20                  25                  30

<210> SEQ ID NO 28
<211> LENGTH: 93
<212> TYPE: DNA
<213> ORGANISM: Artificial
<220> FEATURE:
<223> OTHER INFORMATION: Synthetic polynucleotide

<400> SEQUENCE: 28
actcttcagc aacataaact gcttaaggtg attaggaaga agcttgttcg taaaacgctg     60
gacatgatca agaagattgc tgatgataaa tac                                  93

<210> SEQ ID NO 29
<211> LENGTH: 35
```

```
<212> TYPE: PRT
<213> ORGANISM: Artificial
<220> FEATURE:
<223> OTHER INFORMATION: Synthetic polypeptide

<400> SEQUENCE: 29

His Lys Leu Leu Lys Val Ile Arg Lys Lys Leu Val Arg Lys Thr Leu
1               5                   10                  15

Asp Met Ile Lys Lys Ile Ala Asp Asp Lys Tyr Asn Asp Thr Phe Trp
            20                  25                  30

Lys Glu Phe
        35

<210> SEQ ID NO 30
<211> LENGTH: 105
<212> TYPE: DNA
<213> ORGANISM: Artificial
<220> FEATURE:
<223> OTHER INFORMATION: Synthetic polynucleotide

<400> SEQUENCE: 30
cataaactgc ttaaggtgat taggaagaag cttgttcgta aaacgctgga catgatcaag     60
aagattgctg atgataaata caatgatact ttttggaaag aattt                   105

<210> SEQ ID NO 31
<211> LENGTH: 51
<212> TYPE: PRT
<213> ORGANISM: Artificial
<220> FEATURE:
<223> OTHER INFORMATION: Synthetic polypeptide

<400> SEQUENCE: 31

Asp Asp Leu Pro Leu Asn Val Ser Arg Glu Thr Leu Gln Gln His Lys
1               5                   10                  15

Leu Leu Lys Val Ile Arg Lys Lys Leu Val Arg Lys Thr Leu Asp Met
            20                  25                  30

Ile Lys Lys Ile Ala Asp Asp Lys Tyr Asn Asp Thr Phe Trp Lys Glu
        35                  40                  45

Phe Gly Thr
    50

<210> SEQ ID NO 32
<211> LENGTH: 55
<212> TYPE: PRT
<213> ORGANISM: Artificial
<220> FEATURE:
<223> OTHER INFORMATION: Synthetic polypeptide

<400> SEQUENCE: 32

Leu Asn Val Ser Arg Glu Thr Leu Gln Gln His Lys Leu Leu Lys Val
1               5                   10                  15

Ile Arg Lys Lys Leu Val Arg Lys Thr Leu Asp Met Ile Lys Lys Ile
            20                  25                  30

Ala Asp Asp Lys Tyr Asn Asp Thr Phe Trp Lys Glu Phe Gly Thr Asn
        35                  40                  45

Ile Lys Leu Gly Val Ile Glu
    50                  55

<210> SEQ ID NO 33
<211> LENGTH: 153
<212> TYPE: DNA
<213> ORGANISM: Artificial
<220> FEATURE:
```

-continued

<223> OTHER INFORMATION: Synthetic polynucleotide

<400> SEQUENCE: 33

```
gatgatctcc ccttgaatgt ttcccgcgag actcttcagc aacataaact gcttaaggtg    60
attaggaaga agcttgttcg taaaacgctg gacatgatca agaagattgc tgatgataaa    120
tacaatgata cttttggaa agaatttggt acc                                  153
```

<210> SEQ ID NO 34
<211> LENGTH: 165
<212> TYPE: DNA
<213> ORGANISM: Artificial
<220> FEATURE:
<223> OTHER INFORMATION: Synthetic polynucleotide

<400> SEQUENCE: 34

```
ttgaatgttt cccgcgagac tcttcagcaa cataaactgc ttaaggtgat taggaagaag    60
cttgttcgta aaacgctgga catgatcaag aagattgctg atgataaata caatgatact    120
ttttggaaag aatttggtac caacatcaag cttggtgtga ttgaa                    165
```

<210> SEQ ID NO 35
<211> LENGTH: 31
<212> TYPE: PRT
<213> ORGANISM: Artificial
<220> FEATURE:
<223> OTHER INFORMATION: Synthetic polypeptide

<400> SEQUENCE: 35

```
Thr Leu Gln Gln His Lys Leu Leu Lys Val Ile Arg Lys Lys Leu Val
1               5                   10                  15
Arg Lys Thr Leu Asp Met Ile Lys Lys Ile Ala Asp Asp Lys Tyr
            20                  25                  30
```

<210> SEQ ID NO 36
<211> LENGTH: 31
<212> TYPE: PRT
<213> ORGANISM: Artificial
<220> FEATURE:
<223> OTHER INFORMATION: Synthetic polypeptides

<400> SEQUENCE: 36

```
Thr Leu Gln Gln His Lys Leu Leu Lys Val Ile Arg Lys Lys Leu Val
1               5                   10                  15
Arg Lys Thr Leu Asp Met Ile Lys Lys Ile Ala Glu Asp Lys Tyr
            20                  25                  30
```

<210> SEQ ID NO 37
<211> LENGTH: 31
<212> TYPE: PRT
<213> ORGANISM: Artificial
<220> FEATURE:
<223> OTHER INFORMATION: Synthetic polypeptide

<400> SEQUENCE: 37

```
Thr Leu Gln Gln His Lys Leu Leu Lys Val Ile Arg Lys Lys Leu Val
1               5                   10                  15
Arg Lys Thr Leu Asp Met Ile Lys Lys Ile Ala Asp Glu Lys Tyr
            20                  25                  30
```

<210> SEQ ID NO 38
<211> LENGTH: 31
<212> TYPE: PRT
<213> ORGANISM: Artificial
<220> FEATURE:

-continued

<223> OTHER INFORMATION: Synthetic polypeptide

<400> SEQUENCE: 38

Thr Leu Gln Gln His Lys Leu Leu Lys Val Ile Arg Lys Lys Leu Val
1               5                   10                  15
Arg Lys Thr Leu Asp Met Ile Lys Lys Ile Ala Asp Glu Lys Tyr
            20                  25                  30

<210> SEQ ID NO 39
<211> LENGTH: 31
<212> TYPE: PRT
<213> ORGANISM: Artificial
<220> FEATURE:
<223> OTHER INFORMATION: Synthetic polypeptide

<400> SEQUENCE: 39

Thr Leu Gln Gln His Lys Leu Leu Lys Val Ile Arg Lys Lys Leu Val
1               5                   10                  15
Arg Lys Thr Leu Asp Met Ile Lys Lys Ile Ala Asp Glu Lys Tyr
            20                  25                  30

<210> SEQ ID NO 40
<211> LENGTH: 31
<212> TYPE: PRT
<213> ORGANISM: Artificial
<220> FEATURE:
<223> OTHER INFORMATION: Synthetic polypeptide

<400> SEQUENCE: 40

Thr Leu Gln Gln His Lys Leu Leu Lys Val Ile Arg Lys Lys Leu Val
1               5                   10                  15
Arg Lys Thr Leu Asp Met Ile Lys Lys Ile Ala Asp Glu Lys Tyr
            20                  25                  30

<210> SEQ ID NO 41
<211> LENGTH: 31
<212> TYPE: PRT
<213> ORGANISM: Artificial
<220> FEATURE:
<223> OTHER INFORMATION: Synthetic polypeptide

<400> SEQUENCE: 41

Thr Leu Gln Gln His Lys Leu Leu Lys Val Ile Arg Lys Lys Leu Val
1               5                   10                  15
Arg Lys Thr Leu Asp Met Ile Lys Lys Ile Ala Glu Glu Gln Tyr
            20                  25                  30

<210> SEQ ID NO 42
<211> LENGTH: 35
<212> TYPE: PRT
<213> ORGANISM: Artificial
<220> FEATURE:
<223> OTHER INFORMATION: Synthetic polypeptide

<400> SEQUENCE: 42

His Lys Leu Leu Lys Val Ile Arg Lys Lys Leu Val Arg Lys Thr Leu
1               5                   10                  15
Asp Met Ile Lys Lys Ile Ala Asp Glu Lys Tyr Asn Asp Thr Phe Trp
            20                  25                  30
Lys Glu Phe
        35

<210> SEQ ID NO 43
<211> LENGTH: 35

```
<212> TYPE: PRT
<213> ORGANISM: Artificial
<220> FEATURE:
<223> OTHER INFORMATION: Synthetic polypeptide

<400> SEQUENCE: 43

His Lys Leu Leu Lys Val Ile Arg Lys Lys Leu Val Arg Lys Thr Leu
1               5                   10                  15

Asp Met Ile Lys Lys Ile Ala Glu Glu Lys Tyr Asn Asp Thr Phe Trp
            20                  25                  30

Lys Glu Phe
        35

<210> SEQ ID NO 44
<211> LENGTH: 35
<212> TYPE: PRT
<213> ORGANISM: Artificial
<220> FEATURE:
<223> OTHER INFORMATION: Synthetic polypeptide

<400> SEQUENCE: 44

His Lys Leu Leu Lys Val Ile Arg Lys Lys Leu Val Arg Lys Thr Leu
1               5                   10                  15

Asp Met Ile Lys Lys Ile Ala Asp Asp Lys Tyr Asn Asp Thr Phe Trp
            20                  25                  30

Lys Glu Phe
        35

<210> SEQ ID NO 45
<211> LENGTH: 35
<212> TYPE: PRT
<213> ORGANISM: Artificial
<220> FEATURE:
<223> OTHER INFORMATION: Synthetic polypeptide

<400> SEQUENCE: 45

His Lys Leu Leu Lys Val Ile Arg Lys Lys Leu Val Arg Lys Thr Leu
1               5                   10                  15

Asp Met Ile Lys Lys Ile Ala Asp Asp Lys Tyr Asn Asp Thr Phe Trp
            20                  25                  30

Lys Glu Phe
        35

<210> SEQ ID NO 46
<211> LENGTH: 35
<212> TYPE: PRT
<213> ORGANISM: Artificial
<220> FEATURE:
<223> OTHER INFORMATION: Synthetic polypeptide

<400> SEQUENCE: 46

His Lys Leu Leu Lys Val Ile Arg Lys Lys Leu Val Arg Lys Thr Leu
1               5                   10                  15

Asp Met Ile Lys Lys Ile Ala Asp Asp Lys Tyr Asn Asp Thr Phe Trp
            20                  25                  30

Lys Glu Phe
        35

<210> SEQ ID NO 47
<211> LENGTH: 35
<212> TYPE: PRT
<213> ORGANISM: Artificial
<220> FEATURE:
<223> OTHER INFORMATION: Synthetic polypeptide
```

```
<400> SEQUENCE: 47

His Lys Leu Leu Lys Val Ile Arg Lys Lys Leu Val Arg Lys Thr Leu
1               5                   10                  15

Asp Met Ile Lys Lys Ile Ala Asp Asp Lys Tyr Asn Asp Thr Phe Trp
            20                  25                  30

Lys Glu Phe
        35

<210> SEQ ID NO 48
<211> LENGTH: 35
<212> TYPE: PRT
<213> ORGANISM: Artificial
<220> FEATURE:
<223> OTHER INFORMATION: Synthetic polypeptide

<400> SEQUENCE: 48

His Lys Leu Leu Lys Val Ile Arg Lys Lys Leu Val Arg Lys Thr Leu
1               5                   10                  15

Asp Met Ile Lys Lys Ile Ala Asp Glu Lys Tyr Asn Asp Thr Phe Trp
            20                  25                  30

Lys Glu Phe
        35

<210> SEQ ID NO 49
<211> LENGTH: 35
<212> TYPE: PRT
<213> ORGANISM: Artificial
<220> FEATURE:
<223> OTHER INFORMATION: Synthetic polypeptide

<400> SEQUENCE: 49

His Lys Leu Leu Lys Val Ile Arg Lys Lys Leu Val Arg Lys Thr Leu
1               5                   10                  15

Asp Met Ile Lys Lys Ile Ala Asp Glu Lys Tyr Asn Asp Thr Phe Trp
            20                  25                  30

Lys Glu Phe
        35

<210> SEQ ID NO 50
<211> LENGTH: 35
<212> TYPE: PRT
<213> ORGANISM: Artificial
<220> FEATURE:
<223> OTHER INFORMATION: Synthetic polypeptide

<400> SEQUENCE: 50

His Lys Leu Leu Lys Val Ile Arg Lys Lys Leu Val Arg Lys Thr Leu
1               5                   10                  15

Asp Met Ile Lys Lys Ile Ala Asp Glu Lys Tyr Asn Asp Thr Phe Trp
            20                  25                  30

Lys Glu Phe
        35

<210> SEQ ID NO 51
<211> LENGTH: 35
<212> TYPE: PRT
<213> ORGANISM: Artificial
<220> FEATURE:
<223> OTHER INFORMATION: Synthetic polypeptide

<400> SEQUENCE: 51

His Lys Leu Leu Lys Val Ile Arg Lys Lys Leu Val Arg Lys Thr Leu
```

```
                1               5              10               15
Asp Met Ile Lys Lys Ile Ala Asp Glu Lys Tyr Asn Asp Thr Phe Trp
                       20              25              30

Lys Glu Phe
        35

<210> SEQ ID NO 52
<211> LENGTH: 35
<212> TYPE: PRT
<213> ORGANISM: Artificial
<220> FEATURE:
<223> OTHER INFORMATION: Synthetic polypeptide

<400> SEQUENCE: 52

His Lys Leu Leu Lys Val Ile Arg Lys Lys Leu Val Arg Lys Thr Leu
 1               5              10               15

Asp Met Ile Lys Lys Ile Ala Asp Glu Lys Tyr Asn Asp Thr Phe Trp
                       20              25              30

Lys Glu Phe
        35
```